(12) United States Patent
Xiang et al.

(10) Patent No.: US 9,655,815 B2
(45) Date of Patent: May 23, 2017

(54) DNA VACCINES AGAINST TUMOR GROWTH AND METHODS OF USE THEREOF

(71) Applicant: The Scripps Research Institute, La Jolla, CA (US)

(72) Inventors: Rong Xiang, San Diego, CA (US); He Zhou, San Diego, CA (US); Ralph A Reisfeld, La Jolla, CA (US)

(73) Assignee: The Scripps Research Institute, La Jolla, CA (US)

( * ) Notice: Subject to any disclaimer, the term of this patent is extended or adjusted under 35 U.S.C. 154(b) by 219 days.

(21) Appl. No.: 14/269,998

(22) Filed: May 5, 2014

(65) Prior Publication Data

US 2014/0322249 A1    Oct. 30, 2014

Related U.S. Application Data

(62) Division of application No. 10/807,897, filed on Mar. 24, 2004, now Pat. No. 8,716,254.

(60) Provisional application No. 60/457,009, filed on Mar. 24, 2003.

(51) Int. Cl.
| | | |
|---|---|---|
| *A61J 1/05* | (2006.01) | |
| *A61K 39/00* | (2006.01) | |
| *A61K 6/00* | (2006.01) | |

(52) U.S. Cl.
CPC ...... *A61J 1/05* (2013.01); *A61K 6/00* (2013.01); *A61K 39/0011* (2013.01); *A61K 2039/523* (2013.01); *A61K 2039/53* (2013.01); *A61K 2039/55516* (2013.01); *A61K 2039/55522* (2013.01)

(58) Field of Classification Search
CPC .................. A61K 39/0011; A61K 6/00; A61K 2039/523; A61K 2039/55522; A61K 2039/55516; A61K 2039/53; A61J 1/05
See application file for complete search history.

(56) References Cited

U.S. PATENT DOCUMENTS

| | | | | |
|---|---|---|---|---|
| 3,993,223 A * | 11/1976 | Welker, III | ............ | B65D 1/095 206/528 |
| 5,733,760 A | 3/1998 | Lu et al. | | |
| 6,190,657 B1 | 2/2001 | Pawelek et al. | | |
| 6,335,194 B1 | 1/2002 | Bennett et al. | | |
| 2003/0008840 A1 * | 1/2003 | Vicari | ............ | A61K 47/48423 514/44 R |
| 2003/0100525 A1 * | 5/2003 | Altieri | ............ | C07K 14/4747 514/44 R |
| 2004/0224408 A1 | 11/2004 | Girard et al. | | |
| 2008/0159957 A1 * | 7/2008 | Kavanaugh | ........ | A61K 39/0011 424/9.2 |

FOREIGN PATENT DOCUMENTS

| | | | |
|---|---|---|---|
| WO | WO0003693 A1 * | 1/2000 | |
| WO | WO03031569 A3 * | 12/2004 | |

OTHER PUBLICATIONS

Eo et al."Immunopotentiation of DNA vaccine against herpes simplex virus via co-delivery of plasmid DNA expressing CCR7 ligands." Vaccine. Sep. 14, 2001;19(32):4685-93.*
Kavanaugh et al."U.S. Appl No. 60/414,649" Priority Document. Filed Oct. 1, 2002.*
Li et al., Control of apoptosis and mitotic spindle checkpoint by survivin, Nature 396:580-584, 1998.
Li et al., Pleiotropic cell-division defects and apoptosis induced by interference with survivin function, Nature Cell Biol 1:461-466, 1999.
Lens et al., Survivin is required for a sustained spindle checkpoint arrest in response to lack of tension, EMBO J 22:2934-2947, 2003.
Uren et al., Cloning and expression of apoptosis inhibitory protein homologs that function to inhibit apoptosis and/or bind tumor necrosis factor receptor-associated factors. Proc Natl Acad Sci USA 93(10): 4974-8, 1996.
Ambrosini et al., Induction of apoptosis and inhibition of cell proliferation by survivin gene targeting. J Biol Chem. 273(18):11177-82, 1998.
Rovero et al., Insertion of the DNA for the 163-171 peptide of IL 1beta enables a DNA vaccine encoding p185(neu) to inhibit mammary carcinogenesis in Her-2/neu transgenic BALB/c mice. Gene Ther. 8(6): 447-52, 2001.
Altieri, Validating survivin as a cancer therapeutic target. Nat Rev Cancer. 3(1): 46-54, 2003.
Luther, Differing activities of homeostatic chemokines CCL19. CCL21, and CXCL12 in lymphocyte and dendritic cell recruitment and lymphoid neogenesis. J Immunol. 169(1): 424-33, 2002.
Cui et al., Cytokine genetic adjuvant facilitates prophylactic intravascular DNA vaccine against acute and latent herpes simplex virus infection in mice. Gene Ther. 12(2): 160-8, 2005.
Dieu et al., Selective recruitment of immature and mature dendritic cells by distinct chemokines expressed in different anatomic sites. J Exp Med., 188(2): 373-86, 1998.

(Continued)

*Primary Examiner* — Thaian N Ton
*Assistant Examiner* — Titilayo Moloye
(74) *Attorney, Agent, or Firm* — Olson & Cepuritis, Ltd.

(57) ABSTRACT

A DNA vaccine suitable for eliciting an immune response against cancer cells comprises a DNA construct operably encoding a cancer-associated Inhibitor of Apoptosis-family protein and an immunoactive gene product, such as a cytokine or a ligand for a natural killer cell surface receptor, in a pharmaceutically acceptable carrier. A preferred cytokine is CCL21. Preferred ligands for a natural killer cell surface receptor include human MICA, human MICB, human ULBP1, human ULBP2, and human ULBP3. The cancer-associated Inhibitor of Apoptosis (IAP)-family protein is preferably a survivin protein or livin protein. Method of inhibiting tumor growth by administering the vaccine of the invention to a mammal is also described.

2 Claims, 45 Drawing Sheets

(56) References Cited

OTHER PUBLICATIONS

Nagira et al., A lymphocyte-specific CC chemokine, secondary lymphoid tissue chemokin (SLC), is a highly efficient chemoattractant for B cells and activated T cells. Eur J Immunol. 28(5):1516-23, 1998.
Gordan et al., Universal tumor antigens as targets for immunotherapy, Cytotherapy, 4(4):317-27, 2002.
Haupt et al., The potential of DNA vaccination against tumor-associated antigens for antitumor therapy, Exp Biol Med (Maywood), 227(4):227-37, 2002.
Andersen et al., Spontaneous cytotoxic T-cell responses against survivin-derived MHC class I-restricted T-cell epitopes in situ as well as ex vivo in cancer patients, Cancer Res. 61(16):5964-8, 2001.
Xiang et al., Protective immunity against human carcinoembryonic antigen (CEA) induced by an oral DNA vaccine in CEA-transgenic mice, Clin Cancer Res. 7(3 Suppl):856s-864s, 2001.
Dueger et al., *Salmonella* DNA adenine methylase mutants elicit protective immune responses to homologous and heterologous serovars in chickens, Infect. Immun. 69(12):7950-4, 2001.
Tanabe et al., Direct submission, submitted to Genetics Institute, 87 Cambridge Park Drive, Cambridge, MA 02140, USA, on Jun. 3, 1997, direct submission of DNA sequences of CCL21.

\* cited by examiner

```
   1 agatttgaat cgcgggaccc gttggcagag gtggcggcgg cggcatggt gcccgacgt
  61 tgccccctgc ctggcagccc tttctcaagg accaccgcat ctctacattc aagaactgc
 121 ccttcttgga gggctgcgcc tgcaccccgg agcggatggc cgaggctggc ttcatccact
 181 gccccactga gaacgagcca gacttggccc agtgtttctt ctgcttcaag gagctgaag
 241 gctggagcc agatgacgac cccatagagg aacataaaaa gcattcgtcc ggttgcgctt
 301 tcctttctgt caagaagcag tttgaagaat taacccttgg tgaattttg aaactggaca
 361 gagaaagagc caagaacaaa attgcaaagg aaaccaacaa taagaagaaa gaatttgag
 421 aaactgcgaa cgtgccatcg agcagctggc tgccatggat tgaggcctct
 481 ggccgagct gaaagtgcgc agagtggctg caccacttcc agggtttatt ccctgtgcc
 541 accagccttc gctggtccc cttagcaatg tcttaggaaa ggagatcaac attttcaaat
 601 tagatgtttc aactgtgctc ttgttttgtc ttgaaagtgg caccagagt gcttctgcct
 661 gtgcagcggg tgctgctggt aacagtggct gcttctctct ctctctctct ttttggg
 721 ctcattttg ctgtttttgat tcccgggctt accaggtgag aagtgaggga ggaagaagc
 781 agtgtccctt ttgctagagc tgacagcttt gttcgcgtgg gcagagcctt ccacagtgaa
 841 tgtgtctgga cctcatgttg ttgaggctgt cacagtcctg agtgtggact tgcaggtgc
 901 ctgttgaatc tgagctgcag gttccttatc tgtcacacct gtgcctcctc agaggacagt
 961 tttttgttg tgttttttt tttttttt ctcctctact gtttaacaac tgacttgt gtgatgagag
1021 aatggagaca gagtcccgg gcacagaat gttaacaac acaattaaaa ctaagcacaa agccattcta
1081 gaattgttaa ttcacagaat agcacaaact acaattaaaa tggatgagga gacagaatag agtgatagga
1141 agtcattggg gaaacggggt gaacttcagg tggatgagga gacagaatag agtgatagga
1201 agcgtctggc agatactcct tttgccactg ctgtgtgatt agacaggccc agtgagccgc
1261 gggcacatg ctgccgctc ctccctcaga aaaaggcagt ggcctaaatc ctttttaaat
1321 gacttgctc gatgctgtgg gggactggct gggctgctgc agccgtgtg tctgtcagcc
1381 caaccttcac atctgtcacg ttctccacac ggggagaga cgcagtccgc ccaggtcccc
1441 gctttctttg gaggcagcag ctcccgcagg gctgaagtct ggcgtaagat gatggattg
1501 attcgccctc ctccctgtca tagagctgca gggtggattg ttacagcttc gctggaaacc
1561 tctggggtc atctcggctg ttcctgagaa ataaaaagcc tgtcatttca aataaaaaaa
1621 aaaaaaaaaa aaaaaaaaaa aaa      (SEQ ID NO: 1)HUMAN SURVIVIN
```

FIG. 1

MGAPTLPPAWQPFLKDHRISTFKNWPFLEGCACTPERMAEAGFIHCPTENE
PDLAQCFFCFKELEGWEPDDDPIEEHKKHSSGCAFLSVKKQFEELTLGEFL
KLDRERAKNKIAKETNNKKKEFEETAKKVRRAIEQLAAMD (SEQ ID NO: 2)

HUMAN SURVIVIN

FIG. 2

```
  1 ggcacgaggg ggccggggct ctcccggcat gctctgcggc gcgcctccgc ccgcgcgatt
 61 tgaatcctgc gtttgagtcg tcttggcgga ggttgtggtg acgcatcat gggagctccg
121 gcgctgcccc agatctggca gctgtacctc aagaactacc gcatcgccac cttcaagaac
181 tggcccttcc tggaggactg cgcctgcacc ccagagcgaa tggcggagc tggcttcatc
241 cactgcccta ccgagaacga gcctgatttg gcccagtgtt tttctgctt taaggaattg
301 gaaggctggg aacccgatga gaggagcata gaaagcactc ccctggctgc
361 gccttcctca ctgtcaagaa gcagatggaa gaactaaccg tcagtgaatt cttgaaactg
421 gacagacaga gagccaagaa caaaattgca aaggagacca acaacaagca aaaagagttt
481 gaagagactg caaagactac ccgtcagtca attgagcagc tggctgccta atgctgagcc
541 tttgctgaga taacttggac ctgagtgaca tgccacatct aagccacgca tcccagcttt
601 tccagccagg gcctcctagc aggatcttag agaaggagac agtggtatt tgaaactgga
661 tatcaaatat tttggttttt gcttaaagt ggctacctct ctttggtttt gtggctttgc
721 tctattgtga cgtggactta agcaataagg gggacagtgt tctctgacag
781 gacctgtggg ggtcggggtg cctgtgcaag aagtgcaag tcttggttc tgattgtgat atttccatac
841 agggctgcta atgcagccca tgggtaagtg tggttatatg tgtttgtgct gataattttg
901 tcctgatgag ttttcctacc acggggtaac ggaataaaat cacttgaaaa agtgg
(SEQ ID NO: 3)

(MURINE TIAP)
```

FIG. 3

MGAPALPQIWQLYLKNYRIATFKNWPFLEDCACTPERMAEAGFIHCPTENE
PDLAQCFFCFKELEGWEPDDNPIEEHRKHSPGCAFLTVKKQMEELTVSEFL
KLDRQRAKNKIAKETNNKQKEFEETAKTTRQSIEQLAA (SEQ ID NO: 4)

(MURINE TIAP)

FIG. 4

```
                        10         20         30         40         50         60
                         |          |          |          |          |          |
mTIAP.      MGAPALPQLYLKNYRIATFKNWPFLEDCACTPERMAEAGFIHCPTENEPDLAQCFFC
hSurvivin.  MGAPTLPPAWQPFLKDHRISTFKNWPFLEGCACTPERMAEAGFIHCPTENEPDLAQCFFC 70         80         90        100        110        120
                         |          |          |          |          |          |
mTIAP.      FKELEGWEPDDNPIEEHRKHSPGCAFLTVKKQMEELTVSEFLKLDRQRAKNKIAKETNNK
hSurvivin.  FKELEGWEPDDDPIEEHKKHSSGCAFLSVKKQFEELTLGEFLKLDRERAKNKIAKETNNK 130        140
                         |          |
mTIAP.      QKEFEETAKTTRQSIEQLAA--    (SEQ ID NO: 4)
hSurvivin.  KKEFEETAKKVRRAIEQLAAMD    (SEQ ID NO: 2)
```

FIG. 5

```
  1 cttgcagctg cccacctcac cctcagctct ggcctcttac tcaccctcta ccacagacat
 61 ggctcagtca ctggctctga gcctcctta gcctttctg cctttggca tccccaggac
121 ccaaggcagt gatggagggg ctcaggactg ttgcctcaag tacagccaaa ggaagattcc
181 cgccaaggtt gtccgcagct accggaagca ggaaccaagc ttagctgct ccatcccagc
241 tatcctgttc ttgccccgca agcgctctca ggcagagcta tgtgcagacc caaaggagct
301 ctgggtgcag cagctgatgc agcatctgga caagacacca tccccacaga aaccagccca
361 gggctgcagg aagacaggg gggcctccaa gactggcaag aaagaaaagg gctccaaagg
421 ctgcaagagg actgagcggt cacagacccc taaagggcca tagcccagtg agcagcctgg
481 agccctggag accccaccag cctcaccaac gcttgaagcc tgaaccaag atgcaagaag
541 gaggctatgc tcaggggccc tggagcagcc accccatgct ggccttgcca cactctttct
601 cctgctttaa ccaccccatc tgcattccca gctctaccct gcatggctga gctgcccaca
661 gcaggccagg tccagagaga ccgaggaggg agagtctccc agggagcatg agaggaggca
721 gcaggactgt cccccttgaag gagaatcatc aggaccctgg acctgatacg gctcccagt
781 acaccccacc tcttccttgt aaatatgatt tatacctaac tgaataaaaa gctgttctgt
841 cttcccaccc gc        (SEQ ID NO: 5)
```

(HUMAN SLC)

FIG. 6

MAQSLALSLLILVLAFGIPRTQGSDGGAQDCCLKYSQRKIPAKVVRSYRKQ
EPSLGCSIPAILFLPRKRSQAELCADPKELWVQQLMQHLDKTPSPQKPAQG
CRKDRGASKTGKKGKGSKGCKRTERSQTPKGP (SEQ ID NO: 6)

(HUMAN SLC)

FIG. 7

```
  1 gaattcgcgcc aaagaggcct acggccaaag agggctaaaac ttgcggctgt ccatctcacc
 61 tacagctctg gtctcatcct caactcaacc acaatcatgg ctcagatgat gactctgagc
121 ctccttagcc tggtcctggc tctctgcatc ccctgaccc aaggcagtga tggaggggt
181 caggactgct gccttaagta cagccagaag aaaattcct acagtattgt ccgaggctat
241 aggaagcaag aaccaagttt aggctgtccc atcccggcaa tcctgttctc accccggaag
301 cactctaagc ctgagctatg tgcaaaccct gaggaaggct gggtgcagaa cctgatgcgc
361 cgcctggacc agcctccagc cccagggaaa caaagccccg gctgcaggaa gaaccggga
421 acctctaagt ctggaaagaa aggaaagggc tccaagggct gcaagagaac tgaacagaca
481 cagccctcaa gaggatagcc cagtagcccg cctggagccc aggagatccc ccacgaactt
541 caagctgggt ggttcacggt ccaactcaca ggcaaagagg gagctagaaa acagactcag
601 gagccgctag tcgag  (MURINE SLC CCL21b)

(SEQ ID NO: 7)
```

FIG. 8

MAQMMTLSLLSLVLALCIPWTQGSDGGGQDCCLKYSQKKIPYSIVRGYRKQ
EPSLGCPIPAILFSPRKHSKPELCANPEEGWVQNLMRRLDQPPAPGKQSPG
CRKNRGTSKSGKKGKGSKGCKRTEQTQPSRG (SEQ ID NO: 8)

(MURINE SLC CCL21b)

FIG. 9

```
       10          20          30          40          50          60
        |           |           |           |           |           |
hSLC  MAQSLALSLLILVLAFGIPRTQGSDGGAQDCCLKYSQRKIPAKVRSYRKQEPSLGCSIP
mSLC  MAQMMTLSLLSLVLALCIPWMTQGSDGGGQDCCLKYSQKKIPYSIVRGYRKQEPSLGCPIP 70          80          90         100         110         120         130
        |           |           |           |           |           |           |
hSLC  AILFLPRKRSQAELCADPKELWVQQLMQHLDKIPSPQKPAQGCRKDRGASKTGKKKGKGSK
mSLC  AILFSPRKHSKPELCANPEGWVQNLMRRLDQPAPGKQSPGCRKNRGTSKSGKKGKGSK

140
       |
hSLC  GCKRTERSQTPKGP     (SEQ ID NO: 6)
mSLC  GCKRTEQTQPSRG-     (SEQ ID NO: 8)
```

FIG. 10

Murine minor histocompatibility antigen H60 (partial)

```
  1 tgagggaaga ccatggcaaa gggagccacc agcaagagca accattgcct gattctgagc
 61 cttttcattc tgctgagcta tctggggacc atactggcag atggtacaga ctctctaagt
121 tgtgaattaa cttcaacta tcgtaatcta catggacagt gctcagtgaa tggaaagact
181 ctccttgatt ttggtgataa aaaacatgag gaaaatgcta ctaagatgtg tgctgatttg
241 tcccaaaacc tgagagagat ttcagaagag atgtggaagt tacaatcagg taatgatacc
301 ttgaatgtca caacacaatc tcagtataat caaggaaaat tcattgatgg attctgggcc
361 atcaacactg atgaacagca tagcatctac tttatccac ttaatatgac ctggagagaa
421 agtcattctg ataacagcag tgccatggag cagtgggaaga acaagaacct agagaaagat
481 atgaggaatt tcctcatcac atatttcagt cactgcctca acaaatcgtc atcacactt
541 agagaaatgc caaatcaac attaaaggtg ccggatacca cccaacgtac aaatgccact
601 cagattcatc ctacagtgaa taacttccga cataattctg acaaccaggg tctgagtgtc
661 acctggattg tgattatatg tataggagga ttagtgtctt tcatggcatt catggtattc
721 gcttggtgta tgctgaagaa aaaaaa (SEQ ID NO: 9)
```

FIG. 11

MINOR histocompatibility antigen H60 (partial)

MAKGATSKSNHCLILSLFILLSYLGTILADGTDSLSCELTFNYR
NLHGQCSVNGKTLLDFGDKKHEENATKMCADLSQNLREISEEMWKLQSGNDTLNVTTQ
SQYNQGKFIDGFWAINTDEQHSIYFYPLNMTWRESHSDNSSAMEQWKNKNLEKDMRNF
LITYFSHCLNKSSSHFREMPKSTLKVPDTTQRTNATQIHPTVNNFRHNSDNQGLSVTW
IVIICIGGLVSFMAFMVFAWCMLKKK (SEQ ID NO: 10)

FIG. 12

Expression constructs for SLC and TIAP in a pBudCE4.1 vector

Production of intracellular IFN-γ by DNA vaccine

```
  1 atcccagccc acgcacagac cccaacttg cagctgccca cctcaccctc agctctggcc
 61 tcttactcac cctctaccac agacatggct cagtcactgg ctctgagcct ccttatcctg
121 gttctggcct ttggcatccc caggacccca ggcagtgatg gggggctca ggactgttgc
181 ctcaagtaca gccaaaggaa gattcccgcc aaggtttgtcc gcagctaccg gaagcaggaa
241 ccaagcttag gctgctccat cccagctatc ctgttcttgc cccgcaagcg ctcctcaggca
301 gagctatgtg cagacccaaa ggagctctgg gtgcagcagc tgatgcagca tctggacaag
361 acaccatccc cacagaaacc agcccaggc tgcaggaagg acaggggggc ctccaagact
421 ggcaagaaag gaaagggctc caaaggctgc aagaggactg agcggtcaca gaccctaaa
481 gggccatagc ccagtgagca gcctggagcc ctggagaccc caccagcctc accagcgctt
541 gaagcctgaa cccaagatgc aagaaggagg ctatgctcag gggccctgga gcagccaccc
601 catgctggcc ttgccacact ctttctccctg ctttaaccac cctttaaccac ttcccagctc
661 taccctgcat ggctgagctg cccacagcag gccaggtcca gagagaccga ggggagag
721 tctcccaggg agcatgagag gaggcagcag gactgtcccc ttgaaggaga atcatcagga
781 ccctgaccct gatacggctc cccagtacac cccacctctt ccttgtaaat atgatttata
841 cctaactgaa taaaaagctg ttctgtcttc ccacccaa       (MURINE SLC CCl21a)

(SEQ ID NO: 11)
```

FIG. 25

MAQSLALSLLILVLAFGIPRTQGSDGGAQDCCLKYSQRKIPAKVVRSYRKQ
EPSLGCSIPAILFLPRKRSQAELCADPKELWVQQLMQHLDKTPSPQKPAQG
CRKDRGASKTGKKGKGSKGCKRTERSQTPKGP    (SEQ ID NO: 12)

(MURINE SLC CCL21a)

FIG. 26

Human MICA

```
   1 atgggctgg gcccgtctt cctgcttctg gctggcatct tcccttttgc acctccgga
  61 gctgctgctg agccccacag tcttcgttat aacctcacgg tgctgtcctg ggatggatct
 121 gtgcagtcag ggtttctcac tgaggtacat ctggatggtc agcccttcct gcgctgtgac
 181 aggcagaaat gcaggcaaa gccccaggga cagtgggcag aagatgtcct gggaaataag
 241 acatgggaca gagagaccag agacttgaca gggaacggaa aggacctcag gatgacctg
 301 gctcatatca aggaccagaa agaaggcttg cattccctcc aggagattag ggtctgtgag
 361 atccatgaag acaacagcac caggagctcc cagcatttct actacgatgg ggagctcttc
 421 ctctcccaaa acctggagac taaggaatgg acaatgcccc agtcctccag agctcagacc
 481 ttggccatga acgtcaggaa tttcttgaag gaagatgcca tgaagaccaa gacacactat
 541 cacgctatgc atgcagactg cctgcaggaa ctacggcgat atctaaaatc cggcgtagtc
 601 ctgaggagaa cagtgccccc catggtgaat gtcaccccgca gcgaggcctc agaggcaac
 661 attaccgtga catgcagggc ttctgcttc tatccctgga atatcacact gagctggcgt
 721 caggatgggg tatcttttga ccacgacacc cagcagtggg gggatgtcct gcctgatggg
 781 aatgaacct accagacctg ggtgccacc aggatttgcc aaggagagga gcagaggttc
 841 acctgctaca tggaacacag cggaaatcac agcactcacc ctgtccctc tgggaaagtg
 901 ctggtgcttc agagtcattg gcagacattc catgtttctg ctgttgctgc tgctgctgct
 961 attttttgtta ttattatttt ctatgtccgt tgttgtaaga agaaaacatc agctgcagag
1021 ggtccagagc tcgtgagcct gcaggtcctg gatcaacacc cagttgggac gagtgaccac
1081 agggatgcca cacagctcgg atttcagcct ctgatgtcag atcttggtc cactggctcc
1141 actgagggcg cctag          (SEQ ID NO: 13)
```

FIG. 27

Human MICA

MGLGPVFLLLAGIFPFAPPGAAAEPHSLRYNLTVLSWDGSVQSGFLTEVHL
DGQPFLRCDRQKCRAKPQGQWAEDVLGNKTWDRETRDLTGNGKDLRMTLAH
IKDQKEGLHSLQEIRVCEIHEDNSTRSSQHFYYDGELFLSQNLETKEWTMP
QSSRAQTLAMNVRNFLKEDAMKTKTHYHAMHADCLQELRRYLKSGVVLRRT
VPPMVNVTRSEASEGNITVTCRASGFYPWNITLSWRQDGVSLSHDTQQWGD
VLPDGNGTYQTWVATRICQGEEQRFTCYMEHSGNHSTHPVPSGKVLVLQSH
WQTFHVSAVAAAAIFVIIFYVRCCKKKTSAAEGPELVSLQVLDQHPVGT
SDHRDATQLGFQPLMSDLGSTGSTEGA (SEQ ID NO: 14)

FIG. 28

Human MICB

```
   1 gggccatggg gctgggccgg gtcctgctgt ttctggccgt cgccttccct tttgcacccc
  61 cggcagccgc cgctgagccc cacagtcttc gttacaacct catggtgctg tcccaggatg
 121 gatctgtgca gtcagggttt ctcgctgagg gacatctgga tggtcagccc ttcctgcgct
 181 atgacaggca gaaacgcagg gcaaagcccc agggacagtg ggcagaagat gtcctgggag
 241 ctgagacctg ggacacagag accgaggact tgacagagaa tgggcaagac ctcaggagga
 301 ccctgactca tatcaaggac cagaaaggag gcttgcattc cctccaggag attagggtct
 361 gtgagatcca tgaagacagc agcaccaggg gctcccggca tttctactac aatgggagc
 421 tcttcctctc ccaaaacctg gagactcaag aatcgacagt gccccagtcc tccagagctc
 481 agacctttgc tatgaacgtc acaaatttct ggaaggaaga tgccatgaag accaagacac
 541 actatcgcgc tatgcaggca gactgcctgc agaaactaca gcgatatctg aaatccgggg
 601 tggccatcag gagaacagtg ccccccatgg tgaatgtcac ctgcagcgag gtctcagagg
 661 gcaacatcac cgtgacatgc cgggcttcca gcttctatcc ccggaatatc acactgacct
 721 ggcgtcagga tggggtatct ttgagccaca acaccagca gtgggggat gtcctgcctg
 781 atgggaatgg aacctaccag acctggttg cacacccagg atcgccaagga gaggagcaga
 841 ggttcacctg ctacatggaa cacagcggga atcacggcac tcaccctgtg ccctctggga
 901 aggcgctggt gctccagagt caacgacag actttccata tgttctgct gctatgccat
 961 gttttgttat tattattatt ctctgtgtcc cttgttgcaa gaagaaaaca tcagcggcag
1021 agggtccaga gcttgtgagc ctgcaggtcc tggatcaaca cccagttggg acaggagacc
1081 acaggatgc agcacagctg ggatttcagc ctctgatgtc agctactggg tccactggtt
1141 ccactgaggg cgcctagact ctacagccag gcggccagga ttcaactccc tgcctgatc
1201 tcaccagcac tttccctctg tttcctgacc tatgaaacag aaaataacat cacttattta
1261 ttgttgttgg atgctgcaaa gtgttagtag gtatgaggtg tttgctgctc tgccacgtag
1321 agagccagca aaggatcat gaccaactca acattccatt ggaggctata tgatcaaaca
```

FIG. 29

```
1381 gcaaattgtt tatcatgaat gcaggatgtg ggcaaactca cgactgctcc tgccaacaga
1441 aggtttgctg agggcattca ctccatggtg ctcattggag ttatctactg ggtcatctag
1501 agcctattgt ttgaggaatg cagtcttaca agcctactct ggaccagca gctgactcct
1561 tcttccaccc ctcttcttgc tatctcctat accaataaat acgaaggct gtggaagatc
1621 agagcccttg ttcacgagaa gcaagaagcc ccctgaccc ttgttccaaa tatactcttt
1681 tgtctttctc tttattccca cgttcgccct ttgttcagtc caatacaggg ttgtggggcc
1741 cttaacagtg ccatattaat tggtatcatt atttctgttg ttttgtttt tgtttttgtt
1801 tttgtttttg agacagagtc tcactctgtc acccaggctg cagttcactg gtgtgatctc
1861 agctcactgc aacctctgcc tcccagttc aagcacttct cgtacctcag actcccgaat
1921 agctggatt acagacaggc accaccacac ccagctaatt tttgtatttt ttgtagagac
1981 ggggtttcgc caagttgacc agcccagttt caaactcctg acctcaggtg atctgcctgc
2041 cttggcatcc caaagtgctg ggattacaag aatgagccac cgtgcctggc ctattttatt
2101 atattgtaat atattttatt atattagcca ccatgcctgt cctattttct tatgttttaa
2161 tatattttaa tatattacat gtgcagtaat tagattatca tgggtgaact ttatgagtga
2221 gtatcttggt gatgactcct cctgaccagc ccaggaccag ctttcttgtc accttgaggt
2281 cccctcgccc cgtcacaccg ttatgcatta tctgtgtct actattatgt gtgcataatt
2341 tataccgtaa atgtttactc tttaaataga aaaaaaaaaa aaaaa (SEQ ID NO: 15)
```

FIG. 29 Cont.

Human MICB    MGLGRVLLFLAVAFPFAPPAAAAEPHSLRYNLMVLSQDGSVQSGFLAEG
HLDGQPFLRYDRQKRRAKPQGQWAEDVLGAETWDTETEDLTENGQDLRR
TLTHIKDQKGGLHSLQEIRVCEIHEDSSTRGSRHFYYNGELFLSQNLET
QESTVPQSSRAQTLAMNVTNFWKEDAMKTKTHYRAMQADCLQKLQRYLK
SGVAIRRTVPPMVNVTCSEVSEGNITVTCRASSFYPRNITLTWRQDGVS
LSHNTQQWGDVLPDGNGTYQTWVATRIRQGEEQRFTCYMEHSGNHGTHP
VPSGKALVLQSQRTDFPYVSAAMPCFVIILCVPCCKKKTSAAEGPEL
VSLQVLDQHPVGTGDHRDAAQLGFQPLMSATGSTGSTEGA (SEQ ID NO: 16)

FIG. 30

Human ULBP1

```
  1 atggcagcgg ccgccagccc cgccttcctt ctgtgcctcc cgcttctgca cctgctgtct
 61 ggctgtccc  gggcaggatg ggtcgacaca cactgtcttt gctatgactt catcatcact
121 cctaagtcca gacctgaacc acagtggtgt gaagttcaag gcctggtgga tgaaaggcct
181 tttcttcact atgactgtgt taaccacaag gccaaagcct ttgcttctct ggggaagaaa
241 gtcaatgtca caaaaacctg ggaagaacaa actgaaacac taagagacgt ggtggatttc
301 cttaaagggc aactgcttga cattcaagtg gagaatttaa tacccattga gcccctcacc
361 ctgcaggcca ggatgtcttg tgagcatgaa gcccatggac acggcagagg atcttggcag
421 ttcctcttca atggacagaa gttcctcctc tttgactcaa acaacagaaa gtggacagca
481 cttcatcctg gagccaagaa gatgacagag aagtgggaga aagtgggaga tgtgaccatg
541 ttcttccaga agatttcact ggggattgt  agatgtggc  ttgaagaatt tttgatgtac
601 tgggaacaaa tgctggatcc aacaaaacca cccctctgg  cccaggcac  aacccaaccc
661 aaggccatgg ccaccaccct cagtcccctg agccttctca tcatcttcct ctgcttcatt
721 ctagctggca gatga       (SEQ ID NO: 17)
```

FIG. 31

Human ULBP1

MAAAASPAFLLCLPLLHLLSGWSRAGWVDTHCLCYDFIITPKSRPEPQWCEV
QGLVDERPFLHYDCVNHKAKAFASLGKKVNVTKTWEEQTETLRDVVDFLKGQ
LLDIQVENLIPIEPLTLQARMSCEHEAHGHGRGSWQFLFNGQKFLLFDSNNR
KWTALHPGAKKMTEKWEKNRDVTMFFQKISLGDCKMWLEEFLMYWEQMLDPT
KPPSLAPGTTQPKAMATTLSPWSLLIIFLCFILAGR (SEQ ID NO: 18)

FIG. 32

Human ULBP2

```
  1 atggcagcag ccgccgctac caagatcctt ctgtgcctcc cgcttctgct cctgctgtcc
 61 ggctggtccc gggctgggcg agccgaccct cactctcttt gctatgacat caccgtcatc
121 cctaagttca gacctggacc acggtggtgt gcggttcaag gccaggtgga tgaaaagact
181 tttcttcact atgactgtgg caacaagaca gtcacacctg tcagtcccct ggggaagaaa
241 ctaaatgtca caacggcctg gaaagcacag aacccagtac tgagagaggt ggtggacata
301 cttacagagc aactgcgtga cattcagctg gagaattaca cacccaagga acccctcacc
361 ctgcaggcaa ggatgtcttg tgagcagaaa gctgaaggac acagcagtgg atcttggcag
421 ttcagtttcg atgggcagat cttcctcctc tttgactcag agaagagaat gtggacaacg
481 gttcatcctg gagccagaaa gatgaaagaa aagtgggaga atgacaaggt tgtggccatg
541 tccttccatt acttctcaat gggagactgt ataggatggc ttgaggactt cttgatgggc
601 atggacagca ccctggagcc aagtgcagga gcaccactcg ccatgtcctc aggcacaacc
661 caactcaggg ccacagccac caccctcatc ctttgctgcc tcctcatcat cctcccctgc
721 ttcatcctcc ctggcattctg a    (SEQ ID NO: 19)
```

FIG. 33

Human ULBP2

MAAAATKILLCLPLLLLLSGWSRAGRADPHSLCYDITVIPKFRPGPRWC
AVQGQVDEKTFLHYDCGNKTVTPVSPLGKKLNVTTAWKAQNPVLREVVDI
LTEQLRDIQLENYTPKEPLTLQARMSCEQKAEGHSSGSWQFSFDGQIFLL
FDSEKRMWTTVHPGARKMKEKWENDKVVAMSFHYFSMGDCIGWLEDFLMG
MDSTLEPSAGAPLAMSSGTTQLRATATTLILCCLLILPCFILPGI
(SEQ ID NO: 20)

FIG. 34

Human ULBP3

```
  1 atggcagcgg ccgccagccc cgcgatcctt ccgcgcctcg cgattcttcc gtacctgcta
 61 ttcgactggt ccgggacggg gcgggccgac gctcactctc tctggtataa cttcaccatc
121 attcatttgc ccagacatgg gcaacagtgg tgtgaggtcc agagccaggt ggatcagaag
181 aattttctct cctatgactg tggcagtgac aaggtcttat ctatgggtca cctagaagag
241 cagctgtatg ccacagatgc ctggggaaaa caactggaaa tgctgagaga ggtggggcag
301 aggctcagac tggaactggc tgacactgag ctggaggatt tcacacccag tggaccctc
361 acgctgcagg tcaggatgtc ttgtgagtgt gaagccgatg gatacatccg tggatcttgg
421 cagttcagct tcgatggacg gaagttcctc ctcttgact caaacaacag aaagtggaca
481 gtggttcacg ctggagccag gcggatgaaa gagaagtggg agaaggatag cggactgacc
541 acctcttca agatggtctc aatgagagac tgcaagagct ggcttaggga cttcctgatg
601 cacaggaaga agaggctgga acccacagca ccaccacca tggcccagg cttagctcaa
661 cccaaagcca tagccaccac cctcagtccc tggagcttcc tcatcatcct ctgcttcatc
721 ctcccctggca tctga    (SEQ ID NO: 21)
```

FIG. 35

Human ULBP3

MAAAASPAILPRLAILPYLLFDWSGTGRADAHSLWYNFTIIHLPRHGQQW
CEVQSQVDQKNFLSYDCGSDKVLSMGHLEEQLYATDAWGKQLEMLREVGQ
RLRLELADTELEDFTPSGPLTLQVRMSCECEADGYIRGSWQFSFDGRKFL
LFDSNNRKWTVVHAGARRMKEKWEKDSGLTTFFKMVSMRDCKSWLRDFLM
HRKKRLEPTAPPTMAPGLAQPKAIATTLSPWSFLILCFILPGI
(SEQ ID NO: 22)

FIG. 36

MGAPTLPPAWQPFLKDHRISTFKNWPFLEGCACTPERMAEAGFIHCPTENE
PDLAQCFFCFKELEGWEPDDDPIGPGTVAYACNTSTLGGRGGRITREEHKK
HSSGCAFLSVKKQFEELTLGEFLKLDRERAKNKIAKETNNKKEFEETAKK
VRRAIEQLAAMD (SEQ ID NO: 23)

HUMAN SURVIVIN-2B splice variant

MGAPTLPPAWQPFLKDHRISTFKNWPFLEGCACTPERMAEAGFIHCPTENE
PDLAQCFFCFKELEGWEPDDDPMQRKPTIRRKNLRKLRRKCAVPSSSWLPWI
EASGRSCLVPEWLHHFQGLFPGATSLPVGPLAMS (SEQ ID NO: 24)

HUMAN SURVIVIN-ΔEx3 splice variant

FIG. 37

```
GENBANK      NP_005922. MHC class I polyp...[gi:5174565]  BLink, Domains, Links
LOCUS        MICB                    383 aa            linear   PRI 13-DEC-2002
DEFINITION   MHC class I polypeptide-related sequence B; MHC class I-like
             molecule PERB11.2-IMX; stress inducible class I homolog; MHC class
             I mic-B antigen; MHC class I chain-related protein B; MHC class I
             molecule [Homo sapiens].
ACCESSION    NP_005922
VERSION      NP_005922.1  GI:5174565
DBSOURCE     REFSEQ: accession NM_005931.2
KEYWORDS     .
SOURCE       Homo sapiens (human)
  ORGANISM   Homo sapiens
             Eukaryota; Metazoa; Chordata; Craniata; Vertebrata; Euteleostomi;
             Mammalia; Eutheria; Primates; Catarrhini; Hominidae; Homo.
REFERENCE    1  (residues 1 to 383)
  AUTHORS    Bahram,S., Bresnahan,M., Geraghty,D.E. and Spies,T.
  TITLE      A second lineage of mammalian major histocompatibility complex
             class I genes
  JOURNAL    Proc. Natl. Acad. Sci. U.S.A. 91 (14), 6259-6263 (1994)
  MEDLINE    94294361
   PUBMED    8022771
REFERENCE    2  (residues 1 to 383)
  AUTHORS    Bahram,S. and Spies,T.
  TITLE      Nucleotide sequence of a human MHC class I MICB cDNA
  JOURNAL    Immunogenetics 43 (4), 230-233 (1996)
  MEDLINE    96163024
   PUBMED    8575823
REFERENCE    3  (residues 1 to 383)
  AUTHORS    Nalabolu,S.R., Shukla,H., Nallur,G., Parimoo,S. and Weissman,S.M.
  TITLE      Genes in a 220-kb region spanning the TNF cluster in human MHC
  JOURNAL    Genomics 31 (2), 215-222 (1996)
  MEDLINE    96422187
   PUBMED    8824804
REFERENCE    4  (residues 1 to 383)
  AUTHORS    Groh,V., Bahram,S., Bauer,S., Herman,A., Beauchamp,M. and Spies,T.
  TITLE      Cell stress-regulated human major histocompatibility complex class
             I gene expressed in gastrointestinal epithelium
  JOURNAL    Proc. Natl. Acad. Sci. U.S.A. 93 (22), 12445-12450 (1996)
  MEDLINE    97057262
   PUBMED    8901601
REFERENCE    5  (residues 1 to 383)
  AUTHORS    Bahram,S., Shiina,T., Oka,A., Tamiya,G. and Inoko,H.
  TITLE      Genomic structure of the human MHC class I MICB gene
  JOURNAL    Immunogenetics 45 (2), 161-162 (1996)
  MEDLINE    97113304
   PUBMED    8952966
REFERENCE    6  (residues 1 to 383)
  AUTHORS    Groh,V., Steinle,A., Bauer,S. and Spies,T.
  TITLE      Recognition of stress-induced MHC molecules by intestinal
             epithelial gammadelta T cells
  JOURNAL    Science 279 (5357), 1737-1740 (1998)
  MEDLINE    98163553
   PUBMED    9497295
REFERENCE    7  (residues 1 to 383)
  AUTHORS    Steinle,A., Groh,V. and Spies,T.
  TITLE      Diversification, expression, and gamma delta T cell recognition of
             evolutionarily distant members of the MIC family of major
             histocompatibility complex class I-related molecules
  JOURNAL    Proc. Natl. Acad. Sci. U.S.A. 95 (21), 12510-12515 (1998)
  MEDLINE    98445401
   PUBMED    9770516
REFERENCE    8  (residues 1 to 383)
  AUTHORS    Braud,V.M., Allan,D.S. and McMichael,A.J.
```

FIG. 38

```
  TITLE      Functions of nonclassical MHC and non-MHC-encoded class I molecules
  JOURNAL    Curr. Opin. Immunol. 11 (1), 100-108 (1999)
  MEDLINE    99158668
   PUBMED    10047540
REFERENCE   9  (residues 1 to 383)
  AUTHORS    Cerwenka,A., Bakker,A.B., McClanahan,T., Wagner,J., Wu,J.,
             Phillips,J.H. and Lanier,L.L.
  TITLE      Retinoic acid early inducible genes define a ligand family for the
             activating NKG2D receptor in mice
  JOURNAL    Immunity 12 (6), 721-727 (2000)
  MEDLINE    20350669
   PUBMED    10894171
REFERENCE   10 (residues 1 to 383)
  AUTHORS    Steinle,A., Li,P., Morris,D.L., Groh,V., Lanier,L.L., Strong,R.K.
             and Spies,T.
  TITLE      Interactions of human NKG2D with its ligands MICA, MICB, and
             homologs of the mouse RAE-1 protein family
  JOURNAL    Immunogenetics 53 (4), 279-287 (2001)
  MEDLINE    21383614
   PUBMED    11491531
REFERENCE   11 (residues 1 to 383)
  AUTHORS    Borrego,F., Kabat,J., Kim,D.K., Lieto,L., Maasho,K., Pena,J.,
             Solana,R. and Coligan,J.E.
  TITLE      Structure and function of major histocompatibility complex (MHC)
             class I specific receptors expressed on human natural killer (NK)
             cells
  JOURNAL    Mol. Immunol. 38 (9), 637-660 (2002)
  MEDLINE    21848355
   PUBMED    11858820
COMMENT      REVIEWED REFSEQ: This record has been curated by NCBI staff. The
             reference sequence was derived from U65416.1 and BU684700.1.
             Summary: This gene encodes a heavily glycosylated protein which is
             a ligand for the NKG2D type II receptor. Binding of the ligand
             activates the cytolytic response of natural killer (NK) cells, CD8
             alphabeta T cells, and gammadelta T cells which express the
             receptor. This protein is stress-induced and is similar to MHC
             class I molecules; however, it does not associate with
             beta-2-microglobulin or bind peptides.
FEATURES             Location/Qualifiers
     source          1..383
                     /organism="Homo sapiens"
                     /db_xref="taxon:9606"
                     /chromosome="6"
                     /map="6p21.3"
     Protein         1..383
                     /product="MHC class I polypeptide-related sequence B"
                     /note="MHC class I-like molecule PERB11.2-IMX; stress
                     inducible class I homolog; MHC class I mic-B antigen; MHC
                     class I chain-related protein B; MHC class I molecule"
     Region          24..198
                     /region_name="Class I Histocompatibility antigen, domains
                     alpha 1 and 2"
                     /note="MHC_I"
                     /db_xref="CDD:pfam00129"
     variation       59
                     /allele="C"
                     /allele="Y"
                     /db_xref="dbSNP:1051786"
     variation       64
                     /allele="R"
                     /allele="C"
                     /db_xref="dbSNP:2240858"
     variation       75
```

FIG. 38 Cont.

```
          variation       /allele="N"
                          /allele="D"
                          /allele="N"
                          /allele="D"
                          /db_xref="dbSNP:3131639"
          variation       80
                          /allele="K"
                          /allele="E"
                          /allele="K"
                          /db_xref="dbSNP:1065075"
          variation       121
                          /allele="M"
                          /allele="I"
                          /allele="M"
                          /db_xref="dbSNP:3134900"
          variation       136
                          /allele="N"
                          /allele="D"
                          /allele="H"
                          /allele="N"
                          /allele="D"
                          /db_xref="dbSNP:1051788"
          variation       148
                          /allele="E"
                          /allele="K"
                          /db_xref="dbSNP:1051791"
          Region          222..292
                          /region_name="Immunoglobulin C-Type"
                          /note="IGc1"
                          /db_xref="CDD:smart00407"
          variation       238
                          /allele="S"
                          /allele="T"
                          /db_xref="dbSNP:1051799"
          variation       383
                          /allele="A"
                          /allele="T"
                          /allele="A"
                          /allele="T"
                          /db_xref="dbSNP:1065076"
          CDS             1..383
                          /gene="MICB"
                          /coded_by="NM_005931.2:6..1157"
                          /db_xref="LocusID:4277"
                          /db_xref="MIM:602436"
ORIGIN
        1 mglgrvllfl avafpfappa aaaephslry nlmvlsqdgs vqsgflaegh ldgqpflryd
       61 rqkrrakpqg qwaedvlgae twdtetedlt engqdlrrtl thikdqkggl hslqeirvce
      121 ihedsstrgs rhfyyngelf lsqnletqes tvpqssraqt lamnvtnfwk edamktkthy
      181 ramqadclqk lqrylksgva irrtvppmvn vtcsevsegn itvtcrassf yprnitltwr
      241 qdgvslshnt qqwgdvlpdg ngtyqtwvat rirqgeeqrf tcymehsgnh gthpvpsgka
      301 lvlqsqrtdf pyvsaampcf viiilcvpc ckkktsaaeg pelvslqvld qhpvgtgdhr
      361 daaqlgfqpl msatgstgst ega
//
```

FIG. 38 Cont.

Human livin alpha splice variant

```
   1 ccctgggata ctcccctccc agggtgtctg gtggcaggcc tgtgcctatc cctgctgtcc
  61 ccagggtggg ccccgggggt caggagctcc agaagggcca gctgggcata ttctgagatt
 121 ggccatcagc ccccatttct gctgcaaacc tggtcagagc cagtgttccc tccatgggac
 181 ctaaagacag tgccaagtgc ctgcaccgtg gaccacagcc gagccactgg gcagccggtg
 241 atggtcccac gcaggagcgc tgtggacccc gctctctggg cagccctgtc ctaggcctgg
 301 acacctgcag agcctgggac cacgtggatg ggcagatcct gggccagctg cggcccctga
 361 cagaggagga agaggaggag ggcgccgggg ccaccttgtc caggggggcct gccttccccg
 421 gcatgggctc tgaggagttg cgtctggcct ccttctatga ctggccgctg actgctgagg
 481 tgccacccga gctgctggct gctgccggct tcttccacac aggccatcag gacaaggtga
 541 ggtgcttctt ctgctatggg ggcctgcaga gctggaagcg cggggacgac ccctggacgg
 601 agcatgccaa gtggttcccc agctgtcagt tcctgctccg gtcaaaagga agagactttg
 661 tccacagtgt gcaggagact cactcccagc tgctgggctc ctgggacccg tgggaagaac
 721 cggaagacgc agcccctgtg gcccctccg tccctgcctc tgggtaccct gagctgccca
 781 cacccaggag agaggtccag tctgaaagtg cccaggagcc aggaggggtc agtccagccg
 841 aggcccagag ggcgtggtgg gttcttgagc ccccaggagc cagggatgtg gaggcgcagc
 901 tgcggcggct gcaggaggag aggacgtgca aggtgtgcct ggaccgcgcc gtgtccatcg
 961 tctttgtgcc gtgcggccac ctggtctgtg ctgagtgtgc ccccggcctg cagctgtgcc
1021 ccatctgcag agccccgtc cgcagccgcg tgcgcacctt cctgtcctag gccaggtgcc
1081 atggccggcc aggtgggctg cagagtgggc tccctgcccc tctctgcctg ttctggactg
1141 tgttctgggc ctgctgagga tggcagagct ggtgtccatc cagcactgac cagccctgat
1201 tccccgacca ccgcccaggg tggagaagga ggcccttgct tggcgtgggg gatggcttaa
1261 ctgtacctgt ttggatgctt ctgaatagaa ataaagtggg ttttccctgg aggtacccag
1321 ca
```

(SEQ ID NO: 26)

FIG. 39

Human livin alpha splice variant

MGPKDSAKCLHRGPQPSHWAAGDGPTQERCGPRSLGSPVLGLDTCRAWD

HVDGQILGQLRPLTEEEEEGAGATLSRGPAFPGMGSEELRLASFYDWP

LTAEVPPELLAAAGFFHTGHQDKVRCFFCYGGLQSWKRGDDPWTEHAKW

FPSCQFLLRSKGRDFVHSVQETHSQLLGSWDPWEEPEDAAPVAPSVPAS

GYPELPTPRREVQSESAQEPGGVSPAEAQRAWWVLEPPGARDVEAQLRR

LQEERTCKVCLDRAVSIVFVPCGHLVCAECAPGLQLCPICRAPVRSRVR

TFLS (SEQ ID NO: 27)

FIG. 40

Human livin beta splice variant

```
   1 ccctgggata ctcccctccc agggtgtctg gtggcaggcc tgtgcctatc cctgctgtcc
  61 ccagggtggg ccccgggggt caggagctcc agaagggcca gctgggcata ttctgagatt
 121 ggccatcagc ccccatttct gctgcaaacc tggtcagagc cagtgttccc tccatgggac
 181 ctaaagacag tgccaagtgc ctgcaccgtg gaccacagcc gagccactgg gcagccggtg
 241 atggtcccac gcaggagcgc tgtggacccc gctctctggg cagccctgtc ctaggcctgg
 301 acacctgcag agcctgggac cacgtggatg ggcagatcct gggccagctg cggcccctga
 361 cagaggagga agaggaggag ggcgccgggg ccaccttgtc caggggcct gccttccccg
 421 gcatgggctc tgaggagttg cgtctggcct ccttctatga ctggccgctg actgctgagg
 481 tgccacccga gctgctggct gctgccggct cttccacac aggccatcag gacaaggtga
 541 ggtgcttctt ctgctatggg ggcctgcaga gctggaagcg cggggacgac ccctggacgg
 601 agcatgccaa gtggttcccc agctgtcagt tcctgctccg gtcaaaagga agagactttg
 661 tccacagtgt gcaggagact cactcccagc tgctgggctc ctgggacccg tgggaagaac
 721 cggaagacgc agcccctgtg gcccctccg tcctgcctc tgggtaccct gagctgccca
 781 cacccaggag agaggtccag tctgaaagtg cccaggagcc aggagccagg gatgtggagg
 841 cgcagctgcg gcggctgcag gaggaggag cgtgcaaggt gtgcctggac cgcgccgtgt
 901 ccatcgtctt tgtgccgtgc ggccacctgg tctgtgctga gtgtgccccc ggcctgcagc
 961 tgtgccccat ctgcagagcc cccgtccgca gccgcgtgcg caccttcctg tcctaggcca
1021 ggtgccatgg ccggccaggt gggctgcaga gtgggctccc tgccctctc tgcctgttct
1081 ggactgtgtt ctgggcctgc tgaggatggc agagctggtg tccatccagc actgaccagc
1141 cctgattccc cgaccaccgc ccagggtgga gaaggaggcc cttgcttggc gtgggggatg
1201 gcttaactgt acctgtttgg atgcttctga atagaaataa agtgggtttt ccctggaggt
1261 acccagca
```

FIG. 41

Human livin beta splice variant

MGPKDSAKCLHRGPQPSHWAAGDGPTQERCGPRSLGSPVLGLDTCRAWD

HVDGQILGQLRPLTEEEEEGAGATLSRGPAFPGMGSEELRLASFYDWP

LTAEVPPELLAAAGFFHTGHQDKVRCFFCYGGLQSWKRGDDPWTEHAKW

FPSCQFLLRSKGRDFVHSVQETHSQLLGSWDPWEEPEDAAPVAPSVPAS

GYPELPTPRREVQSESAQEPGARDVEAQLRRLQEERTCKVCLDRAVSIV

FVPCGHLVCAECAPGLQLCPICRAPVRSRVRTFLS (SEQ ID NO: 29)

FIG. 42

SEQUENCE LISTING

<160> NUMBER OF SEQ ID NOS: 29

<210> SEQ ID NO 1
<211> LENGTH: 1643
<212> TYPE: DNA
<213> ORGANISM: HOMO SAPIENS

<400> SEQUENCE: 1
agatttgaat cgcgggaccc gttggcagag gtggcggcgg cggcatgggt gccccgacgt    60 tgcccctgc ctggcagccc tttctcaagg accaccgcat ctctacattc aagaactggc    120

-continued

```
ccttcttgga gggctgcgcc tgcaccccgg agcggatggc cgaggctggc ttcatccact    180
gccccactga gaacgagcca gacttggccc agtgtttctt ctgcttcaag gagctggaag    240
gctgggagcc agatgacgac cccatagagg aacataaaaa gcattcgtcc ggttgcgctt    300
tcctttctgt caagaagcag tttgaagaat aacccttggt gaattttttg aaactggaca    360
gagaaagagc caagaacaaa attgcaaagg aaaccaacaa taagaagaaa gaatttgagg    420
aaactgcgaa gaaagtgcgc cgtgccatcg agcagctggc tgccatggat tgaggcctct    480
ggccggagct gcctggtccc agagtggctg caccacttcc agggtttatt ccctggtgcc    540
accagccttc ctgtgggccc cttagcaatg tcttaggaaa ggagatcaac attttcaaat    600
tagatgtttc aactgtgctc ttgttttgtc ttgaaagtgg caccagaggt gcttctgcct    660
gtgcagcggg tgctgctggt aacagtggct gcttctctct ctctctctct tttttggggg    720
ctcattttg ctgttttgat tcccgggctt accaggtgag aagtgaggga ggaagaaggc    780
agtgtccctt ttgctagagc tgacagcttt gttcgcgtgg gcagagcctt ccacagtgaa    840
tgtgtctgga cctcatgttg ttgaggctgt cacagtcctg agtgtggact tggcaggtgc    900
ctgttgaatc tgagctgcag gttccttatc tgtcacacct gtgcctcctc agaggacagt    960
ttttttgttg tgttttttt ttttttttt ggtagatgca tgacttgtgt gtgatgagag   1020
aatggagaca gagtccccgg ctcctctact gtttaacaac atggctttct tattttgttt   1080
gaattgttaa ttcacagaat agcacaaact acaattaaaa ctaagcacaa agccattcta   1140
agtcattggg gaaacggggt gaacttcagg tggatgagga gacagaatag agtgatagga   1200
agcgtctggc agatactcct tttgccactg ctgtgtgatt agacaggccc agtgagccgc   1260
ggggcacatg ctggccgctc ctccctcaga aaaaggcagt ggcctaaatc ctttttaaat   1320
gacttggctc gatgctgtgg gggactggct gggctgctgc aggccgtgtg tctgtcagcc   1380
caaccttcac atctgtcacg ttctccacac gggggagaga cgcagtccgc ccaggtcccc   1440
gctttctttg gaggcagcag ctcccgcagg gctgaagtct ggcgtaagat gatggatttg   1500
attcgccctc ctccctgtca tagagctgca gggtggattg ttacagcttc gctggaaacc   1560
tctggaggtc atctcggctg ttcctgagaa ataaaaagcc tgtcatttca aataaaaaaa   1620
aaaaaaaaaa aaaaaaaaaa aaa                                          1643
```

<210> SEQ ID NO 2
<211> LENGTH: 142
<212> TYPE: PRT
<213> ORGANISM: HOMO SAPIENS

<400> SEQUENCE: 2

```
Met Gly Ala Pro Thr Leu Pro Pro Ala Trp Gln Pro Phe Leu Lys Asp
 1               5                  10                  15
His Arg Ile Ser Thr Phe Lys Asn Trp Pro Phe Leu Glu Gly Cys Ala
            20                  25                  30
Cys Thr Pro Glu Arg Met Ala Glu Ala Gly Phe Ile His Cys Pro Thr
        35                  40                  45
Glu Asn Glu Pro Asp Leu Ala Gln Cys Phe Phe Cys Phe Lys Glu Leu
    50                  55                  60
Glu Gly Trp Glu Pro Asp Asp Asp Pro Ile Glu His Lys Lys His
65                  70                  75                  80
Ser Ser Gly Cys Ala Phe Leu Ser Val Lys Lys Gln Phe Glu Glu Leu
                85                  90                  95
Thr Leu Gly Glu Phe Leu Lys Leu Asp Arg Glu Arg Ala Lys Asn Lys
```

```
            100                 105                 110
Ile Ala Lys Glu Thr Asn Asn Lys Lys Lys Glu Phe Glu Glu Thr Ala
            115                 120                 125

Lys Lys Val Arg Arg Ala Ile Glu Gln Leu Ala Ala Met Asp
            130                 135                 140

<210> SEQ ID NO 3
<211> LENGTH: 955
<212> TYPE: DNA
<213> ORGANISM: MUS MUSCULUS

<400> SEQUENCE: 3
ggcacgaggg ggccggggct ctcccggcat gctctgcggc gcgcctccgc ccgcgcgatt      60
tgaatcctgc gtttgagtcg tcttggcgga ggttgtggtg acgccatcat gggagctccg     120
gcgctgcccc agatctggca gctgtacctc aagaactacc gcatcgccac cttcaagaac     180
tggcccttcc tggaggactg cgcctgcacc ccagagcgaa tggcggaggc tggcttcatc     240
cactgcccta ccgagaacga gcctgatttg gcccagtgtt ttttctgctt taaggaattg     300
gaaggctggg aacccgatga caacccgata gaggagcata gaaagcactc ccctggctgc     360
gccttcctca ctgtcaagaa gcagatggaa gaactaaccg tcagtgaatt cttgaaactg     420
gacagacaga gagccaagaa caaaattgca aaggagacca caacaagca aaaagagttt     480 gaagagactg caaagactac ccgtcagtca attgagcagc tggctgccta atgctgagcc     540
tttgctgaga taacttggac ctgagtgaca tgccacatct aagccacgca tcccagcttt     600
tccagccagg gcctcctagc aggatcttag agaaggagac agtggtattt tgaaactgga     660
tatcaaatat ttttggtttt gctttaaagt ggctacctct ctttggtttt gtggctttgc     720
tctattgtga cgtggactta agcaataagg aagtgatgaa gggacagtgt tctctgacag     780
gacctgtggg ggtcggggtg cctgtgcaag gtcttggttc tgattgtgat atttccatac     840
agggctgcta atgcagccca tgggtaagtg tggttatatg tgtttgtgct gataattttg     900
tcctgatgag ttttcctacc acggggtaac ggaataaaat cacttgaaaa agtgg          955

<210> SEQ ID NO 4
<211> LENGTH: 140
<212> TYPE: PRT
<213> ORGANISM: MUS MUSCULUS

<400> SEQUENCE: 4

Met Gly Ala Pro Ala Leu Pro Gln Ile Trp Gln Leu Tyr Leu Lys Asn
  1               5                  10                  15

Tyr Arg Ile Ala Thr Phe Lys Asn Trp Pro Phe Leu Glu Asp Cys Ala
             20                  25                  30

Cys Thr Pro Glu Arg Met Ala Glu Ala Gly Phe Ile His Cys Pro Thr
         35                  40                  45

Glu Asn Glu Pro Asp Leu Ala Gln Cys Phe Phe Cys Phe Lys Glu Leu
     50                  55                  60

Glu Gly Trp Glu Pro Asp Asp Asn Pro Ile Glu Glu His Arg Lys His
 65                  70                  75                  80

Ser Pro Gly Cys Ala Phe Leu Thr Val Lys Lys Gln Met Glu Glu Leu
                 85                  90                  95

Thr Val Ser Glu Phe Leu Lys Leu Asp Arg Gln Arg Ala Lys Asn Lys
            100                 105                 110

Ile Ala Lys Glu Thr Asn Asn Lys Gln Lys Glu Phe Glu Glu Thr Ala
            115                 120                 125
```

```
Lys Thr Thr Arg Gln Ser Ile Glu Gln Leu Ala Ala
    130                 135                 140

<210> SEQ ID NO 5
<211> LENGTH: 852
<212> TYPE: DNA
<213> ORGANISM: HOMO SAPIENS

<400> SEQUENCE: 5
cttgcagctg cccacctcac cctcagctct ggcctcttac tcaccctcta ccacagacat      60
ggctcagtca ctggctctga gcctccttat cctggttctg gcctttggca tccccaggac     120
ccaaggcagt gatggagggg ctcaggactg ttgcctcaag tacagccaaa ggaagattcc     180
cgccaaggtt gtccgcagct accggaagca ggaaccaagc ttaggctgct ccatcccagc     240
tatcctgttc ttgccccgca agcgctctca ggcagagcta tgtgcagacc caaaggagct     300
ctgggtgcag cagctgatgc agcatctgga caagacacca tccccacaga aaccagccca     360
gggctgcagg aaggacaggg gggcctccaa gactggcaag aaaggaaagg gctccaaagg     420
ctgcaagagg actgagcggt cacagacccc taaagggcca tagcccagtg agcagcctgg     480
agccctggag accccaccag cctcaccaac gcttgaagcc tgaacccaag atgcaagaag     540
gaggctatgc tcaggggccc tggagcagcc accccatgct ggccttgcca cactctttct     600
cctgctttaa ccaccccatc tgcattccca gctctaccct gcatggctga gctgcccaca     660
gcaggccagg tccagagaga ccgaggaggg agagtctccc agggagcatg agaggaggca     720
gcaggactgt ccccttgaag gagaatcatc aggaccctgg acctgatacg gctcccagt      780 acacccccacc tcttccttgt aaatatgatt tatacctaac tgaataaaaa gctgttctgt     840
cttcccaccc gc                                                          852

<210> SEQ ID NO 6
<211> LENGTH: 134
<212> TYPE: PRT
<213> ORGANISM: HOMO SAPIENS

<400> SEQUENCE: 6

Met Ala Gln Ser Leu Ala Leu Ser Leu Leu Ile Leu Val Leu Ala Phe
 1               5                   10                  15

Gly Ile Pro Arg Thr Gln Gly Ser Asp Gly Gly Ala Gln Asp Cys Cys
                20                  25                  30

Leu Lys Tyr Ser Gln Arg Lys Ile Pro Ala Lys Val Val Arg Ser Tyr
            35                  40                  45

Arg Lys Gln Glu Pro Ser Leu Gly Cys Ser Ile Pro Ala Ile Leu Phe
    50                  55                  60

Leu Pro Arg Lys Arg Ser Gln Ala Glu Leu Cys Ala Asp Pro Lys Glu
65                  70                  75                  80

Leu Trp Val Gln Gln Leu Met Gln His Leu Asp Lys Thr Pro Ser Pro
                85                  90                  95

Gln Lys Pro Ala Gln Gly Cys Arg Lys Asp Arg Gly Ala Ser Lys Thr
            100                 105                 110

Gly Lys Lys Gly Lys Gly Ser Lys Gly Cys Lys Arg Thr Glu Arg Ser
        115                 120                 125

Gln Thr Pro Lys Gly Pro
    130

<210> SEQ ID NO 7
```

<211> LENGTH: 615
<212> TYPE: DNA
<213> ORGANISM: MUS MUSCULUS

<400> SEQUENCE: 7

```
gaattcggcc aaagaggcct acggccaaag agggctaaac ttgcggctgt ccatctcacc    60
tacagctctg gtctcatcct caactcaacc acaatcatgg ctcagatgat gactctgagc   120
ctccttagcc tggtcctggc tctctgcatc ccctggaccc aaggcagtga tgaggggggt   180
caggactgct gccttaagta cagccagaag aaaattccct acagtattgt ccgaggctat   240
aggaagcaag aaccaagttt aggctgtccc atcccggcaa tcctgttctc accccggaag   300
cactctaagc ctgagctatg tgcaaaccct gaggaaggct gggtgcagaa cctgatgcgc   360
cgcctggacc agcctccagc cccagggaaa caaagccccg gctgcaggaa gaaccgggga   420
acctctaagt ctggaaagaa aggaaagggc tccaagggct gcaagagaac tgaacagaca   480
cagccctcaa gaggatagcc cagtagcccg cctggagccc aggagatccc ccacgaactt   540
caagctgggt ggttcacggt ccaactcaca ggcaaagagg gagctagaaa acagactcag   600
gagccgctag tcgag                                                    615
```

<210> SEQ ID NO 8
<211> LENGTH: 133
<212> TYPE: PRT
<213> ORGANISM: MUS MUSCULUS

<400> SEQUENCE: 8

```
Met Ala Gln Met Met Thr Leu Ser Leu Leu Ser Leu Val Leu Ala Leu
  1               5                  10                  15

Cys Ile Pro Trp Thr Gln Gly Ser Asp Gly Gly Gln Asp Cys Cys
             20                  25                  30

Leu Lys Tyr Ser Gln Lys Lys Ile Pro Tyr Ser Ile Val Arg Gly Tyr
         35                  40                  45

Arg Lys Gln Glu Pro Ser Leu Gly Cys Pro Ile Pro Ala Ile Leu Phe
     50                  55                  60

Ser Pro Arg Lys His Ser Lys Pro Glu Leu Cys Ala Asn Pro Glu Glu
 65                  70                  75                  80

Gly Trp Val Gln Asn Leu Met Arg Arg Leu Asp Gln Pro Pro Ala Pro
                 85                  90                  95

Gly Lys Gln Ser Pro Gly Cys Arg Lys Asn Arg Gly Thr Ser Lys Ser
            100                 105                 110

Gly Lys Lys Gly Lys Gly Ser Lys Gly Cys Lys Arg Thr Glu Gln Thr
        115                 120                 125

Gln Pro Ser Arg Gly
    130
```

<210> SEQ ID NO 9
<211> LENGTH: 746
<212> TYPE: DNA
<213> ORGANISM: MUS MUSCULUS

<400> SEQUENCE: 9

```
tgagggaaga ccatggcaaa gggagccacc agcaagagca accattgcct gattctgagc    60
cttttcattc tgctgagcta tctggggacc atactggcag atggtacaga ctctctaagt   120
tgtgaattaa ctttcaacta tcgtaatcta catggacagt gctcagtgaa tggaaagact   180
ctccttgatt ttggtgataa aaaacatgag gaaaatgcta ctaagatgtg tgctgatttg   240
```

-continued

| | | | | |
|---|---|---|---|---|
| tcccaaaacc | tgagagagat | ttcagaagag | atgtggaagt | tacaatcagg | taatgatacc | 300 |
| ttgaatgtca | caacacaatc | tcagtataat | caaggaaaat | tcattgatgg | attctgggcc | 360 |
| atcaacactg | atgaacagca | tagcatctac | ttttatccac | ttaatatgac | ctggagagaa | 420 |
| agtcattctg | ataacagcag | tgccatggag | cagtggaaga | acaagaacct | agagaaagat | 480 |
| atgaggaatt | tcctcatcac | atatttcagt | cactgcctca | acaaatcgtc | atcacacttt | 540 |
| agagaaatgc | caaatcaac | attaaaggtg | ccggatacca | cccaacgtac | aaatgccact | 600 |
| cagattcatc | ctacagtgaa | taacttccga | cataattctg | caaccaggg | tctgagtgtc | 660 |
| acctggattg | tgattatatg | tataggagga | ttagtgtctt | tcatggcatt | catggtattc | 720 |
| gcttggtgta | tgctgaagaa | aaaaaa | | | | 746 |

<210> SEQ ID NO 10
<211> LENGTH: 244
<212> TYPE: PRT
<213> ORGANISM: MUS MUSCULUS

<400> SEQUENCE: 10

Met Ala Lys Gly Ala Thr Ser Lys Ser Asn His Cys Leu Ile Leu Ser
1               5                   10                  15

Leu Phe Ile Leu Leu Ser Tyr Leu Gly Thr Ile Leu Ala Asp Gly Thr
            20                  25                  30

Asp Ser Leu Ser Cys Glu Leu Thr Phe Asn Tyr Arg Asn Leu His Gly
        35                  40                  45

Gln Cys Ser Val Asn Gly Lys Thr Leu Leu Asp Phe Gly Asp Lys Lys
    50                  55                  60

His Glu Glu Asn Ala Thr Lys Met Cys Ala Asp Leu Ser Gln Asn Leu
65                  70                  75                  80

Arg Glu Ile Ser Glu Met Trp Lys Leu Gln Ser Gly Asn Asp Thr
                85                  90                  95

Leu Asn Val Thr Thr Gln Ser Gln Tyr Asn Gln Gly Lys Phe Ile Asp
            100                 105                 110

Gly Phe Trp Ala Ile Asn Thr Asp Glu Gln His Ser Ile Tyr Phe Tyr
        115                 120                 125

Pro Leu Asn Met Thr Trp Arg Glu Ser His Ser Asp Asn Ser Ser Ala
    130                 135                 140

Met Glu Gln Trp Lys Asn Lys Asn Leu Glu Lys Asp Met Arg Asn Phe
145                 150                 155                 160

Leu Ile Thr Tyr Phe Ser His Cys Leu Asn Lys Ser Ser Ser His Phe
                165                 170                 175

Arg Glu Met Pro Lys Ser Thr Leu Lys Val Pro Asp Thr Thr Gln Arg
            180                 185                 190

Thr Asn Ala Thr Gln Ile His Pro Thr Val Asn Asn Phe Arg His Asn
        195                 200                 205

Ser Asp Asn Gln Gly Leu Ser Val Thr Trp Ile Val Ile Ile Cys Ile
    210                 215                 220

Gly Gly Leu Val Ser Phe Met Ala Phe Met Val Phe Ala Trp Cys Met
225                 230                 235                 240

Leu Lys Lys Lys

<210> SEQ ID NO 11
<211> LENGTH: 878
<212> TYPE: DNA
<213> ORGANISM: MUS MUSCULUS

-continued

<400> SEQUENCE: 11

```
atcccagccc acgcacagac ccccaacttg cagctgccca cctcaccctc agctctggcc      60
tcttactcac cctctaccac agacatggct cagtcactgg ctctgagcct ccttatcctg     120
gttctggcct ttggcatccc caggacccaa ggcagtgatg gaggggctca ggactgttgc     180
ctcaagtaca gccaaaggaa gattcccgcc aaggttgtcc gcagctaccg gaagcaggaa     240
ccaagcttag gctgctccat cccagctatc ctgttcttgc cccgcaagcg ctctcaggca     300
gagctatgtg cagacccaaa ggagctctgg gtgcagcagc tgatgcagca tctggacaag     360
acaccatccc cacagaaacc agcccagggc tgcaggaagg acagggggc ctccaagact      420
ggcaagaaag gaaagggctc caaggctgc aagaggactg agcggtcaca gaccoctaaa      480
gggccatagc ccagtgagca gcctggagcc ctggagaccc caccagcctc accagcgctt     540
gaagcctgaa cccaagatgc aagaaggagg ctatgctcag gggccctgga gcagccaccc     600
catgctggcc ttgccacact ctttctcctg ctttaaccac cccatctgca ttcccagctc     660
taccctgcat ggctgagctg cccacagcag gccaggtcca gagagaccga ggagggagag     720
tctcccaggg agcatgagag gaggcagcag gactgtcccc ttgaaggaga atcatcagga     780
ccctggacct gatacggctc cccagtacac cccacctctt ccttgtaaat atgatttata     840
cctaactgaa taaaaagctg ttctgtcttc ccacccaa                              878
```

<210> SEQ ID NO 12
<211> LENGTH: 134
<212> TYPE: PRT
<213> ORGANISM: MUS MUSCULUS

<400> SEQUENCE: 12

```
Met Ala Gln Ser Leu Ala Leu Ser Leu Leu Ile Leu Val Leu Ala Phe
  1               5                  10                  15

Gly Ile Pro Arg Thr Gln Gly Ser Asp Gly Ala Gln Asp Cys Cys
             20                  25                  30

Leu Lys Tyr Ser Gln Arg Lys Ile Pro Ala Lys Val Val Arg Ser Tyr
         35                  40                  45

Arg Lys Gln Glu Pro Ser Leu Gly Cys Ser Ile Pro Ala Ile Leu Phe
     50                  55                  60

Leu Pro Arg Lys Arg Ser Gln Ala Glu Leu Cys Ala Asp Pro Lys Glu
 65                  70                  75                  80

Leu Trp Val Gln Gln Leu Met Gln His Leu Asp Lys Thr Pro Ser Pro
                 85                  90                  95

Gln Lys Pro Ala Gln Gly Cys Arg Lys Asp Arg Gly Ala Ser Lys Thr
            100                 105                 110

Gly Lys Lys Gly Lys Gly Ser Lys Gly Cys Lys Arg Thr Glu Arg Ser
        115                 120                 125

Gln Thr Pro Lys Gly Pro
    130
```

<210> SEQ ID NO 13
<211> LENGTH: 1155
<212> TYPE: DNA
<213> ORGANISM: HOMO SAPIENS

<400> SEQUENCE: 13

```
atggggctgg gccggtctt cctgcttctg gctggcatct tccctttgc acctccggga       60
gctgctgctg agccccacag tcttcgttat aacctcacgg tgctgtcctg ggatggatct     120
```

```
gtgcagtcag ggtttctcac tgaggtacat ctggatggtc agcccttcct gcgctgtgac    180
aggcagaaat gcagggcaaa gccccaggga cagtgggcag aagatgtcct gggaaataag    240
acatgggaca gagagaccag agacttgaca gggaacggaa aggacctcag gatgaccctg    300
gctcatatca aggaccagaa agaaggcttg cattccctcc aggagattag ggtctgtgag    360
atccatgaag acaacagcac caggagctcc cagcatttct actacgatgg ggagctcttc    420
ctctcccaaa acctggagac taaggaatgg acaatgcccc agtcctccag agctcagacc    480
ttggccatga acgtcaggaa tttcttgaag gaagatgcca tgaagaccaa gacacactat    540
cacgctatgc atgcagactg cctgcaggaa ctacggcgat atctaaaatc cggcgtagtc    600
ctgaggagaa cagtgccccc catggtgaat gtcacccgca gcgaggcctc agagggcaac    660
attaccgtga catgcagggc ttctggcttc tatccctgga atatcacact gagctggcgt    720
caggatgggg tatctttgag ccacgacacc cagcagtggg gggatgtcct gcctgatggg    780
aatggaacct accagacctg ggtggccacc aggatttgcc aaggagagga gcagaggttc    840
acctgctaca tggaacacag cgggaatcac agcactcacc ctgtgccctc tgggaaagtg    900
ctggtgcttc agagtcattg gcagacattc catgtttctg ctgttgctgc tgctgctgct    960
atttttgtta ttattatttt ctatgtccgt tgttgtaaga agaaaacatc agctgcagag    1020
ggtccagagc tcgtgagcct gcaggtcctg gatcaacacc cagttgggac gagtgaccac    1080
agggatgcca cacagctcgg atttcagcct ctgatgtcag atcttgggtc cactggctcc    1140
actgagggcg cctag                                                      1155
```

<210> SEQ ID NO 14
<211> LENGTH: 384
<212> TYPE: PRT
<213> ORGANISM: HOMO SAPIENS

<400> SEQUENCE: 14

Met Gly Leu Gly Pro Val Phe Leu Leu Ala Gly Ile Phe Pro Phe
 1               5                  10                  15

Ala Pro Pro Gly Ala Ala Ala Glu Pro His Ser Leu Arg Tyr Asn Leu
                20                  25                  30

Thr Val Leu Ser Trp Asp Gly Ser Val Gln Ser Gly Phe Leu Thr Glu
            35                  40                  45

Val His Leu Asp Gly Gln Pro Phe Leu Arg Cys Asp Arg Gln Lys Cys
        50                  55                  60

Arg Ala Lys Pro Gln Gly Gln Trp Ala Glu Asp Val Leu Gly Asn Lys
65                  70                  75                  80

Thr Trp Asp Arg Glu Thr Arg Asp Leu Thr Gly Asn Gly Lys Asp Leu
                85                  90                  95

Arg Met Thr Leu Ala His Ile Lys Asp Gln Lys Glu Gly Leu His Ser
            100                 105                 110

Leu Gln Glu Ile Arg Val Cys Glu Ile His Glu Asp Asn Ser Thr Arg
        115                 120                 125

Ser Ser Gln His Phe Tyr Tyr Asp Gly Glu Leu Phe Leu Ser Gln Asn
    130                 135                 140

Leu Glu Thr Lys Glu Trp Thr Met Pro Gln Ser Ser Arg Ala Gln Thr
145                 150                 155                 160

Leu Ala Met Asn Val Arg Asn Phe Leu Lys Glu Asp Ala Met Lys Thr
                165                 170                 175

Lys Thr His Tyr His Ala Met His Ala Asp Cys Leu Gln Glu Leu Arg
            180                 185                 190

```
Arg Tyr Leu Lys Ser Gly Val Val Leu Arg Arg Thr Val Pro Pro Met
        195                 200                 205

Val Asn Val Thr Arg Ser Glu Ala Ser Glu Gly Asn Ile Thr Val Thr
210                 215                 220

Cys Arg Ala Ser Gly Phe Tyr Pro Trp Asn Ile Thr Leu Ser Trp Arg
225                 230                 235                 240

Gln Asp Gly Val Ser Leu Ser His Asp Thr Gln Gln Trp Gly Asp Val
                245                 250                 255

Leu Pro Asp Gly Asn Gly Thr Tyr Gln Thr Trp Val Ala Thr Arg Ile
            260                 265                 270

Cys Gln Gly Glu Glu Gln Arg Phe Thr Cys Tyr Met Glu His Ser Gly
        275                 280                 285

Asn His Ser Thr His Pro Val Pro Ser Gly Lys Val Leu Val Leu Gln
    290                 295                 300

Ser His Trp Gln Thr Phe His Val Ser Ala Val Ala Ala Ala Ala Ala
305                 310                 315                 320

Ile Phe Val Ile Ile Ile Phe Tyr Val Arg Cys Cys Lys Lys Lys Thr
                325                 330                 335

Ser Ala Ala Glu Gly Pro Glu Leu Val Ser Leu Gln Val Leu Asp Gln
            340                 345                 350

His Pro Val Gly Thr Ser Asp His Arg Asp Ala Thr Gln Leu Gly Phe
        355                 360                 365

Gln Pro Leu Met Ser Asp Leu Gly Ser Thr Gly Ser Thr Glu Gly Ala
    370                 375                 380

<210> SEQ ID NO 15
<211> LENGTH: 2385
<212> TYPE: DNA
<213> ORGANISM: HOMO SAPIENS

<400> SEQUENCE: 15
gggccatggg gctgggccgg gtcctgctgt tctggccgt cgccttccct tttgcacccc      60
cggcagccgc cgctgagccc cacagtcttc gttacaacct catggtgctg tcccaggatg    120
gatctgtgca gtcagggttt ctcgctgagg acatctgga tggtcagccc ttcctgcgct    180
atgacaggca gaaacgcagg gcaaagcccc agggacagtg ggcagaagat gtcctgggag    240
ctgagacctg gacacagag accgaggact tgacagaaga tgggcaagac tcaggagga    300 ccctgactca tatcaaggac cagaaggag gcttgcattc cctccaggag attagggtct    360
gtgagatcca tgaagacagc agcaccaggg gctcccggca tttctactac aatggggagc    420
tcttcctctc ccaaaacctg gagactcaag aatcgacagt gccccagtcc tccagagctc    480
agaccttggc tatgaacgtc acaaatttct ggaaggaaga tgccatgaag accaagacac    540
actatcgcgc tatgcaggca gactgcctgc agaaactaca gcgatatctg aaatccgggg    600
tggccatcag gaacagtg ccccccatgg tgaatgtcac ctgcagcgag gtctcagagg    660
gcaacatcac cgtgacatgc agggcttcca gcttctatcc ccggaatatc acactgacct    720
ggcgtcagga tggggtatct ttgagccaca cacccagca gtgggggggat gtcctgcctg    780 atgggaatgg aaacctaccag acctgggtgg ccaccaggat tcgccaagga gaggagcaga    840
ggttcacctg ctacatggaa cacagcggga atcacggcac tcaccctgtg ccctctggga    900
aggcgctggt gctccagagt caacggacag acttttccata tgtttctgct gctatgccat    960
gttttgttat tattattatt ctctgtgtcc cttgttgcaa gaagaaaaca tcagcggcag   1020
```

```
aggagtccaga gcttgtgagc ctgcaggtcc tggatcaaca cccagttggg acaggagacc      1080
acagggatgc agcacagctg ggatttcagc ctctgatgtc agctactggg tccactggtt      1140
ccactgaggg cgcctagact ctacagccag gcggccagga ttcaactccc tgcctggatc      1200
tcaccagcac tttccctctg tttcctgacc tatgaaacag aaaataacat cacttattta      1260
ttgttgttgg atgctgcaaa gtgttagtag gtatgaggtg tttgctgctc tgccacgtag      1320
agagccagca aagggatcat gaccaactca acattccatt ggaggctata tgatcaaaca      1380
gcaaattgtt tatcatgaat gcaggatgtg ggcaaactca cgactgctcc tgccaacaga      1440
aggtttgctg agggcattca ctccatggtg ctcattggag ttatctactg ggtcatctag      1500
agcctattgt ttgaggaatg cagtcttaca agcctactct ggacccagca gctgactcct      1560
tcttccaccc ctcttcttgc tatctcctat accaataaat acgaagggct gtggaagatc      1620
agagcccttg ttcacgagaa gcaagaagcc cctgacccc ttgttccaaa tatactcttt       1680
tgtctttctc tttattccca cgttcgcccct tgttcagtc caatacaggg ttgtggggcc      1740
cttaacagtg ccatattaat tggtatcatt atttctgttg ttttttgtttt tgttttttgtt   1800 tttgttttg agacagagtc tcactctgtc acccaggctg cagttcactg gtgtgatctc       1860
agctcactgc aacctctgcc tcccaggttc aagcacttct cgtacctcag actcccgaat      1920
agctgggatt acagacaggc accaccacac ccagctaatt tttgtatttt ttgtagagac      1980 ggggttcgc caagttgacc agcccagttt caaactcctg acctcaggtg atctgcctgc       2040
cttggcatcc caaagtgctg ggattacaag aatgagccac cgtgcctggc ctatttttatt    2100 atattgtaat atatttttatt atattagcca ccatgcctgt cctatttttct tatgttttaa    2160 tatatttaa tatattacat gtgcagtaat tagattatca tgggtgaact ttatgagtga      2220
gtatcttggt gatgactcct cctgaccagc ccaggaccag cttcttgtc accttgaggt       2280 ccctcgccc cgtcacaccg ttatgcatta ctctgtgtct actattatgt gtgcataatt       2340
tataccgtaa atgtttactc tttaaataga aaaaaaaaaa aaaaa                      2385

<210> SEQ ID NO 16
<211> LENGTH: 383
<212> TYPE: PRT
<213> ORGANISM: HOMO SAPIENS

<400> SEQUENCE: 16

Met Gly Leu Gly Arg Val Leu Leu Phe Leu Ala Val Ala Phe Pro Phe
 1               5                  10                  15

Ala Pro Pro Ala Ala Ala Glu Pro His Ser Leu Arg Tyr Asn Leu
            20                  25                  30

Met Val Leu Ser Gln Asp Gly Ser Val Gln Ser Gly Phe Leu Ala Glu
        35                  40                  45

Gly His Leu Asp Gly Gln Pro Phe Leu Arg Tyr Asp Arg Gln Lys Arg
    50                  55                  60

Arg Ala Lys Pro Gln Gly Gln Trp Ala Glu Asp Val Leu Gly Ala Glu
65                  70                  75                  80

Thr Trp Asp Thr Glu Thr Glu Asp Leu Thr Glu Asn Gly Gln Asp Leu
                85                  90                  95

Arg Arg Thr Leu Thr His Ile Lys Asp Gln Lys Gly Gly Leu His Ser
            100                 105                 110

Leu Gln Glu Ile Arg Val Cys Glu Ile His Glu Asp Ser Ser Thr Arg
        115                 120                 125

Gly Ser Arg His Phe Tyr Tyr Asn Gly Glu Leu Phe Leu Ser Gln Asn
```

```
                    130                 135                 140
Leu Glu Thr Gln Glu Ser Thr Val Pro Gln Ser Ser Arg Ala Gln Thr
145                 150                 155                 160

Leu Ala Met Asn Val Thr Asn Phe Trp Lys Glu Asp Ala Met Lys Thr
                165                 170                 175

Lys Thr His Tyr Arg Ala Met Gln Ala Asp Cys Leu Gln Lys Leu Gln
            180                 185                 190

Arg Tyr Leu Lys Ser Gly Val Ala Ile Arg Arg Thr Val Pro Pro Met
        195                 200                 205

Val Asn Val Thr Cys Ser Glu Val Ser Glu Gly Asn Ile Thr Val Thr
    210                 215                 220

Cys Arg Ala Ser Ser Phe Tyr Pro Arg Asn Ile Thr Leu Thr Trp Arg
225                 230                 235                 240

Gln Asp Gly Val Ser Leu Ser His Asn Thr Gln Trp Gly Asp Val
                245                 250                 255

Leu Pro Asp Gly Asn Gly Thr Tyr Gln Thr Trp Val Ala Thr Arg Ile
                260                 265                 270

Arg Gln Gly Glu Glu Gln Arg Phe Thr Cys Tyr Met Glu His Ser Gly
            275                 280                 285

Asn His Gly Thr His Pro Val Pro Ser Gly Lys Ala Leu Val Leu Gln
        290                 295                 300

Ser Gln Arg Thr Asp Phe Pro Tyr Val Ser Ala Met Pro Cys Phe
305                 310                 315                 320

Val Ile Ile Ile Leu Cys Val Pro Cys Cys Lys Lys Lys Thr Ser
                325                 330                 335

Ala Ala Glu Gly Pro Glu Leu Val Ser Leu Gln Val Leu Asp Gln His
            340                 345                 350

Pro Val Gly Thr Gly Asp His Arg Asp Ala Ala Gln Leu Gly Phe Gln
        355                 360                 365

Pro Leu Met Ser Ala Thr Gly Ser Thr Gly Ser Thr Glu Gly Ala
    370                 375                 380

<210> SEQ ID NO 17
<211> LENGTH: 735
<212> TYPE: DNA
<213> ORGANISM: HOMO SAPIENS

<400> SEQUENCE: 17
atggcagcgg ccgccagccc cgccttcctt ctgtgcctcc cgcttctgca cctgctgtct      60
ggctggtccc gggcaggatg ggtcgacaca cactgtcttt gctatgactt catcatcact     120
cctaagtcca gacctgaacc acagtggtgt gaagttcaag gcctggtgga tgaaaggcct     180
tttcttcact atgactgtgt taaccacaag gccaaagcct tgcttctctc tggggaagaa     240
gtcaatgtca caaaaaccctg ggaagaacaa actgaaacac taagagacgt ggtggatttc     300
cttaaagggc aactgcttga cattcaagtg gagaatttaa tacccattga gccccctcacc     360 ctgcaggcca ggatgtcttg tgagcatgaa gcccatggac acggcagagg atcttggcag     420
ttcctcttca tggacagaa gttcctcctc tttgactcaa acaacagaaa gtggacagca     480
cttcatcctg gagccaagaa gatgacagag aagtgggaga gaacaggga tgtgaccatg     540 ttccttccaga agatttcact gggggattgt aagatgtggc ttgaagaatt tttgatgtac     600
tgggaacaaa tgctggatcc aacaaaacca ccctctctgg ccccaggcac aacccaaccc     660
aaggccatgg ccaccaccct cagtccctgg agccttctca tcatcttcct ctgcttcatt     720
```

```
ctagctggca gatga                                                       735
```

<210> SEQ ID NO 18
<211> LENGTH: 244
<212> TYPE: PRT
<213> ORGANISM: HOMO SAPIENS

<400> SEQUENCE: 18

```
Met Ala Ala Ala Ala Ser Pro Ala Phe Leu Leu Cys Leu Pro Leu Leu
 1               5                  10                  15

His Leu Leu Ser Gly Trp Ser Arg Ala Gly Trp Val Asp Thr His Cys
            20                  25                  30

Leu Cys Tyr Asp Phe Ile Ile Thr Pro Lys Ser Arg Pro Glu Pro Gln
        35                  40                  45

Trp Cys Glu Val Gln Gly Leu Val Asp Glu Arg Pro Phe Leu His Tyr
    50                  55                  60

Asp Cys Val Asn His Lys Ala Lys Ala Phe Ala Ser Leu Gly Lys Lys
65                  70                  75                  80

Val Asn Val Thr Lys Thr Trp Glu Glu Gln Thr Glu Thr Leu Arg Asp
                85                  90                  95

Val Val Asp Phe Leu Lys Gly Gln Leu Leu Asp Ile Gln Val Glu Asn
            100                 105                 110

Leu Ile Pro Ile Glu Pro Leu Thr Leu Gln Ala Arg Met Ser Cys Glu
        115                 120                 125

His Glu Ala His Gly His Gly Arg Gly Ser Trp Gln Phe Leu Phe Asn
    130                 135                 140

Gly Gln Lys Phe Leu Leu Phe Asp Ser Asn Asn Arg Lys Trp Thr Ala
145                 150                 155                 160

Leu His Pro Gly Ala Lys Lys Met Thr Glu Lys Trp Glu Lys Asn Arg
                165                 170                 175

Asp Val Thr Met Phe Phe Gln Lys Ile Ser Leu Gly Asp Cys Lys Met
            180                 185                 190

Trp Leu Glu Glu Phe Leu Met Tyr Trp Glu Gln Met Leu Asp Pro Thr
        195                 200                 205

Lys Pro Pro Ser Leu Ala Pro Gly Thr Thr Gln Pro Lys Ala Met Ala
    210                 215                 220

Thr Thr Leu Ser Pro Trp Ser Leu Leu Ile Ile Phe Leu Cys Phe Ile
225                 230                 235                 240

Leu Ala Gly Arg
```

<210> SEQ ID NO 19
<211> LENGTH: 741
<212> TYPE: DNA
<213> ORGANISM: HOMO SAPIENS

<400> SEQUENCE: 19

```
atggcagcag ccgccgctac caagatcctt ctgtgcctcc cgcttctgct cctgctgtcc     60
ggctggtccc gggctgggcg agccgaccct cactctcttt gctatgacat caccgtcatc    120
cctaagttca gacctggacc acggtggtgt gcggttcaag gccaggtgga tgaaaagact    180
tttcttcact atgactgtgg caacaagaca gtcacacctg tcagtcccct ggggaagaaa    240
ctaaatgtca aacggcctg gaaagcacag aacccagtac tgagagaggt ggtggacata    300
cttacagagc aactgcgtga cattcagctg gagaattaca cacccaagga accccctcacc   360 ctgcaggcaa ggatgtcttg tgagcagaaa gctgaaggac acagcagtgg atcttggcag    420
```

-continued

```
ttcagtttcg atgggcagat cttcctcctc tttgactcag agaagagaat gtggacaacg    480
gttcatcctg gagccagaaa gatgaaagaa aagtgggaga tgacaaggt tgtggccatg     540 tccttccatt acttctcaat gggagactgt ataggatggc ttgaggactt cttgatgggc    600
atggacagca ccctggagcc aagtgcagga gcaccactcg ccatgtcctc aggcacaacc    660
caactcaggg ccacagccac caccctcatc ctttgctgcc tcctcatcat cctcccctgc    720
ttcatcctcc ctggcatctg a                                              741
```

<210> SEQ ID NO 20
<211> LENGTH: 246
<212> TYPE: PRT
<213> ORGANISM: HOMO SAPIENS

<400> SEQUENCE: 20

```
Met Ala Ala Ala Ala Thr Lys Ile Leu Leu Cys Leu Pro Leu Leu
 1               5                   10                  15

Leu Leu Leu Ser Gly Trp Ser Arg Ala Gly Arg Ala Asp Pro His Ser
            20                  25                  30

Leu Cys Tyr Asp Ile Thr Val Ile Pro Lys Phe Arg Pro Gly Pro Arg
        35                  40                  45

Trp Cys Ala Val Gln Gly Gln Val Asp Glu Lys Thr Phe Leu His Tyr
    50                  55                  60

Asp Cys Gly Asn Lys Thr Val Thr Pro Val Ser Pro Leu Gly Lys Lys
65                  70                  75                  80

Leu Asn Val Thr Thr Ala Trp Lys Ala Gln Asn Pro Val Leu Arg Glu
                85                  90                  95

Val Val Asp Ile Leu Thr Glu Gln Leu Arg Asp Ile Gln Leu Glu Asn
            100                 105                 110

Tyr Thr Pro Lys Glu Pro Leu Thr Leu Gln Ala Arg Met Ser Cys Glu
        115                 120                 125

Gln Lys Ala Glu Gly His Ser Ser Gly Ser Trp Gln Phe Ser Phe Asp
    130                 135                 140

Gly Gln Ile Phe Leu Leu Phe Asp Ser Glu Lys Arg Met Trp Thr Thr
145                 150                 155                 160

Val His Pro Gly Ala Arg Lys Met Lys Glu Lys Trp Glu Asn Asp Lys
                165                 170                 175

Val Val Ala Met Ser Phe His Tyr Phe Ser Met Gly Asp Cys Ile Gly
            180                 185                 190

Trp Leu Glu Asp Phe Leu Met Gly Met Asp Ser Thr Leu Glu Pro Ser
        195                 200                 205

Ala Gly Ala Pro Leu Ala Met Ser Ser Gly Thr Thr Gln Leu Arg Ala
    210                 215                 220

Thr Ala Thr Thr Leu Ile Leu Cys Cys Leu Leu Ile Ile Leu Pro Cys
225                 230                 235                 240

Phe Ile Leu Pro Gly Ile
                245
```

<210> SEQ ID NO 21
<211> LENGTH: 735
<212> TYPE: DNA
<213> ORGANISM: HOMO SAPIENS

<400> SEQUENCE: 21

```
atggcagcgg ccgccagccc cgcgatcctt ccgcgcctcg cgattcttcc gtacctgcta    60
ttcgactggt ccgggacggg gcgggccgac gctcactctc tctggtataa cttcaccatc   120
```

```
attcatttgc ccagacatgg gcaacagtgg tgtgaggtcc agagccaggt ggatcagaag    180
aattttctct cctatgactg tggcagtgac aaggtcttat ctatgggtca cctagaagag    240
cagctgtatg ccacagatgc ctggggaaaa caactggaaa tgctgagaga ggtggggcag    300
aggctcagac tggaactggc tgacactgag ctggaggatt tcacacccag tggacccctc    360
acgctgcagg tcaggatgtc ttgtgagtgt gaagccgatg gatacatccg tggatcttgg    420
cagttcagct tcgatggacg gaagttcctc ctctttgact caaacaacag aaagtggaca    480
gtggttcacg ctggagccag gcggatgaaa gagaagtggg agaaggatag cggactgacc    540
accttcttca gatggtctc aatgagagac tgcaagagct ggcttaggga cttcctgatg    600
cacaggaaga agaggctgga acccacagca ccacccacca tggccccagg cttagctcaa    660
cccaaagcca tagccaccac cctcagtccc tggagcttcc tcatcatcct ctgcttcatc    720
ctccctggca tctga                                                   735
```

<210> SEQ ID NO 22
<211> LENGTH: 244
<212> TYPE: PRT
<213> ORGANISM: HOMO SAPIENS

<400> SEQUENCE: 22

```
Met Ala Ala Ala Ser Pro Ala Ile Leu Pro Arg Leu Ala Ile Leu
 1               5                  10                  15

Pro Tyr Leu Leu Phe Asp Trp Ser Gly Thr Gly Arg Ala Asp Ala His
                20                  25                  30

Ser Leu Trp Tyr Asn Phe Thr Ile Ile His Leu Pro Arg His Gly Gln
            35                  40                  45

Gln Trp Cys Glu Val Gln Ser Gln Val Asp Gln Lys Asn Phe Leu Ser
        50                  55                  60

Tyr Asp Cys Gly Ser Asp Lys Val Leu Ser Met Gly His Leu Glu Glu
65                  70                  75                  80

Gln Leu Tyr Ala Thr Asp Ala Trp Gly Lys Gln Leu Glu Met Leu Arg
                85                  90                  95

Glu Val Gly Gln Arg Leu Arg Leu Glu Leu Ala Asp Thr Glu Leu Glu
            100                 105                 110

Asp Phe Thr Pro Ser Gly Pro Leu Thr Leu Gln Val Arg Met Ser Cys
        115                 120                 125

Glu Cys Glu Ala Asp Gly Tyr Ile Arg Gly Ser Trp Gln Phe Ser Phe
    130                 135                 140

Asp Gly Arg Lys Phe Leu Leu Phe Asp Ser Asn Asn Arg Lys Trp Thr
145                 150                 155                 160

Val Val His Ala Gly Ala Arg Arg Met Lys Glu Lys Trp Glu Lys Asp
                165                 170                 175

Ser Gly Leu Thr Thr Phe Phe Lys Met Val Ser Met Arg Asp Cys Lys
            180                 185                 190

Ser Trp Leu Arg Asp Phe Leu Met His Arg Lys Lys Arg Leu Glu Pro
        195                 200                 205

Thr Ala Pro Pro Thr Met Ala Pro Gly Leu Ala Gln Pro Lys Ala Ile
    210                 215                 220

Ala Thr Thr Leu Ser Pro Trp Ser Phe Leu Ile Ile Leu Cys Phe Ile
225                 230                 235                 240

Leu Pro Gly Ile
```

<210> SEQ ID NO 23
<211> LENGTH: 165
<212> TYPE: PRT
<213> ORGANISM: HOMO SAPIENS

<400> SEQUENCE: 23

```
Met Gly Ala Pro Thr Leu Pro Pro Ala Trp Gln Pro Phe Leu Lys Asp
  1               5                  10                  15

His Arg Ile Ser Thr Phe Lys Asn Trp Pro Phe Leu Glu Gly Cys Ala
             20                  25                  30

Cys Thr Pro Glu Arg Met Ala Glu Ala Gly Phe Ile His Cys Pro Thr
         35                  40                  45

Glu Asn Glu Pro Asp Leu Ala Gln Cys Phe Phe Cys Phe Lys Glu Leu
     50                  55                  60

Glu Gly Trp Glu Pro Asp Asp Asp Pro Ile Gly Pro Gly Thr Val Ala
 65                  70                  75                  80

Tyr Ala Cys Asn Thr Ser Thr Leu Gly Gly Arg Gly Gly Arg Ile Thr
                 85                  90                  95

Arg Glu Glu His Lys Lys His Ser Ser Gly Cys Ala Phe Leu Ser Val
            100                 105                 110

Lys Lys Gln Phe Glu Glu Leu Thr Leu Gly Glu Phe Leu Lys Leu Asp
        115                 120                 125

Arg Glu Arg Ala Lys Asn Lys Ile Ala Lys Glu Thr Asn Asn Lys Lys
    130                 135                 140

Lys Glu Phe Glu Glu Thr Ala Lys Lys Val Arg Arg Ala Ile Glu Gln
145                 150                 155                 160

Leu Ala Ala Met Asp
                165
```

<210> SEQ ID NO 24
<211> LENGTH: 137
<212> TYPE: PRT
<213> ORGANISM: HOMO SAPIENS

<400> SEQUENCE: 24

```
Met Gly Ala Pro Thr Leu Pro Pro Ala Trp Gln Pro Phe Leu Lys Asp
  1               5                  10                  15

His Arg Ile Ser Thr Phe Lys Asn Trp Pro Phe Leu Glu Gly Cys Ala
             20                  25                  30

Cys Thr Pro Glu Arg Met Ala Glu Ala Gly Phe Ile His Cys Pro Thr
         35                  40                  45

Glu Asn Glu Pro Asp Leu Ala Gln Cys Phe Phe Cys Phe Lys Glu Leu
     50                  55                  60

Glu Gly Trp Glu Pro Asp Asp Asp Pro Met Gln Arg Lys Pro Thr Ile
 65                  70                  75                  80

Arg Arg Lys Asn Leu Arg Lys Leu Arg Arg Lys Cys Ala Val Pro Ser
                 85                  90                  95

Ser Ser Trp Leu Pro Trp Ile Glu Ala Ser Gly Arg Ser Cys Leu Val
            100                 105                 110

Pro Glu Trp Leu His His Phe Gln Gly Leu Phe Pro Gly Ala Thr Ser
        115                 120                 125

Leu Pro Val Gly Pro Leu Ala Met Ser
    130                 135
```

<210> SEQ ID NO 25
<211> LENGTH: 9
<212> TYPE: PRT

-continued

<213> ORGANISM: HOMO SAPIENS

<400> SEQUENCE: 25

Ala Tyr Ala Cys Asn Thr Ser Thr Leu
1               5

<210> SEQ ID NO 26
<211> LENGTH: 1322
<212> TYPE: DNA
<213> ORGANISM: homo sapiens
<220> FEATURE:
<221> NAME/KEY: CDS
<222> LOCATION: (174)...(1070)

<400> SEQUENCE: 26

```
ccctgggata ctcccctccc agggtgtctg gtggcaggcc tgtgcctatc cctgctgtcc      60
ccagggtggg ccccgggggt caggagctcc agaagggcca gctgggcata ttctgagatt     120
ggccatcagc ccccatttct gctgcaaacc tggtcagagc cagtgttccc tcc atg        176
                                                           Met
                                                           1 gga cct aaa gac agt gcc aag tgc ctg cac cgt gga cca cag ccg agc      224
Gly Pro Lys Asp Ser Ala Lys Cys Leu His Arg Gly Pro Gln Pro Ser
        5                  10                  15 cac tgg gca gcc ggt gat ggt ccc acg cag gag cgc tgt gga ccc cgc      272
His Trp Ala Ala Gly Asp Gly Pro Thr Gln Glu Arg Cys Gly Pro Arg
         20                  25                  30 tct ctg ggc agc cct gtc cta ggc ctg gac acc tgc aga gcc tgg gac      320
Ser Leu Gly Ser Pro Val Leu Gly Leu Asp Thr Cys Arg Ala Trp Asp
 35                  40                  45 cac gtg gat ggg cag atc ctg ggc cag ctg cgg ccc ctg aca gag gag      368
His Val Asp Gly Gln Ile Leu Gly Gln Leu Arg Pro Leu Thr Glu Glu
 50                  55                  60                  65 gaa gag gag gag ggc gcc ggg gcc acc ttg tcc agg ggg cct gcc ttc      416
Glu Glu Glu Glu Gly Ala Gly Ala Thr Leu Ser Arg Gly Pro Ala Phe
                 70                  75                  80 ccc ggc atg ggc tct gag gag ttg cgt ctg gcc tcc ttc tat gac tgg      464
Pro Gly Met Gly Ser Glu Glu Leu Arg Leu Ala Ser Phe Tyr Asp Trp
             85                  90                  95 ccg ctg act gct gag gtg cca ccc gag ctg ctg gct gct gcc ggc ttc      512
Pro Leu Thr Ala Glu Val Pro Pro Glu Leu Leu Ala Ala Ala Gly Phe
         100                 105                 110 ttc cac aca ggc cat cag gac aag gtg agg tgc ttc ttc tgc tat ggg      560
Phe His Thr Gly His Gln Asp Lys Val Arg Cys Phe Phe Cys Tyr Gly
 115                 120                 125 ggc ctg cag agc tgg aag cgc ggg gac gac ccc tgg acg gag cat gcc      608
Gly Leu Gln Ser Trp Lys Arg Gly Asp Asp Pro Trp Thr Glu His Ala
130                 135                 140                 145 aag tgg ttc ccc agc tgt cag ttc ctg ctc cgg tca aaa gga aga gac      656
Lys Trp Phe Pro Ser Cys Gln Phe Leu Leu Arg Ser Lys Gly Arg Asp
                 150                 155                 160 ttt gtc cac agt gtg cag gag act cac tcc cag ctg ctg ggc tcc tgg      704
Phe Val His Ser Val Gln Glu Thr His Ser Gln Leu Leu Gly Ser Trp
             165                 170                 175 gac ccg tgg gaa gaa ccg gaa gac gca gcc cct gtg gcc ccc tcc gtc      752
Asp Pro Trp Glu Glu Pro Glu Asp Ala Ala Pro Val Ala Pro Ser Val
         180                 185                 190 cct gcc tct ggg tac cct gag ctg ccc aca ccc agg aga gag gtc cag      800
Pro Ala Ser Gly Tyr Pro Glu Leu Pro Thr Pro Arg Arg Glu Val Gln
 195                 200                 205 tct gaa agt gcc cag gag cca gga ggg gtc agt cca gcc gag gcc cag      848
```

-continued

```
Ser Glu Ser Ala Gln Glu Pro Gly Gly Val Ser Pro Ala Glu Ala Gln
210                 215                 220                 225 agg gcg tgg tgg gtt ctt gag ccc cca gga gcc agg gat gtg gag gcg        896
Arg Ala Trp Trp Val Leu Glu Pro Pro Gly Ala Arg Asp Val Glu Ala
                    230                 235                 240 cag ctg cgg cgg ctg cag gag gag agg acg tgc aag gtg tgc ctg gac        944
Gln Leu Arg Arg Leu Gln Glu Glu Arg Thr Cys Lys Val Cys Leu Asp
                245                 250                 255 cgc gcc gtg tcc atc gtc ttt gtg ccg tgc ggc cac ctg gtc tgt gct        992
Arg Ala Val Ser Ile Val Phe Val Pro Cys Gly His Leu Val Cys Ala
            260                 265                 270 gag tgt gcc ccc ggc ctg cag ctg tgc ccc atc tgc aga gcc ccc gtc       1040
Glu Cys Ala Pro Gly Leu Gln Leu Cys Pro Ile Cys Arg Ala Pro Val
        275                 280                 285 cgc agc cgc gtg cgc acc ttc ctg tcc tag gccaggtgcc atggccggcc         1090
Arg Ser Arg Val Arg Thr Phe Leu Ser  *
290                 295 aggtgggctg cagagtgggc tccctgcccc tctctgcctg ttctggactg tgttctgggc    1150
ctgctgagga tggcagagct ggtgtccatc cagcactgac cagccctgat tccccgacca    1210
ccgcccaggg tggagaagga ggcccttgct tggcgtgggg gatggcttaa ctgtacctgt    1270
ttggatgctt ctgaatagaa ataaagtggg ttttccctgg aggtacccag ca            1322

<210> SEQ ID NO 27
<211> LENGTH: 298
<212> TYPE: PRT
<213> ORGANISM: homo sapiens

<400> SEQUENCE: 27

Met Gly Pro Lys Asp Ser Ala Lys Cys Leu His Arg Gly Pro Gln Pro
1               5                   10                  15

Ser His Trp Ala Ala Gly Asp Gly Pro Thr Gln Glu Arg Cys Gly Pro
            20                  25                  30

Arg Ser Leu Gly Ser Pro Val Leu Gly Leu Asp Thr Cys Arg Ala Trp
        35                  40                  45

Asp His Val Asp Gly Gln Ile Leu Gly Gln Leu Arg Pro Leu Thr Glu
    50                  55                  60

Glu Glu Glu Glu Glu Gly Ala Gly Ala Thr Leu Ser Arg Gly Pro Ala
65                  70                  75                  80

Phe Pro Gly Met Gly Ser Glu Glu Leu Arg Leu Ala Ser Phe Tyr Asp
                85                  90                  95

Trp Pro Leu Thr Ala Glu Val Pro Pro Glu Leu Leu Ala Ala Ala Gly
            100                 105                 110

Phe Phe His Thr Gly His Gln Asp Lys Val Arg Cys Phe Phe Cys Tyr
        115                 120                 125

Gly Gly Leu Gln Ser Trp Lys Arg Gly Asp Asp Pro Trp Thr Glu His
    130                 135                 140

Ala Lys Trp Phe Pro Ser Cys Gln Phe Leu Leu Arg Ser Lys Gly Arg
145                 150                 155                 160

Asp Phe Val His Ser Val Gln Glu Thr His Ser Gln Leu Leu Gly Ser
                165                 170                 175

Trp Asp Pro Trp Glu Glu Pro Glu Asp Ala Ala Pro Val Ala Pro Ser
            180                 185                 190

Val Pro Ala Ser Gly Tyr Pro Glu Leu Pro Thr Pro Arg Arg Glu Val
        195                 200                 205

Gln Ser Glu Ser Ala Gln Glu Pro Gly Gly Val Ser Pro Ala Glu Ala
```

```
                210                 215                 220
Gln Arg Ala Trp Trp Val Leu Glu Pro Pro Gly Ala Arg Asp Val Glu
225                 230                 235                 240

Ala Gln Leu Arg Arg Leu Gln Glu Glu Arg Thr Cys Lys Val Cys Leu
                245                 250                 255

Asp Arg Ala Val Ser Ile Val Phe Val Pro Cys Gly His Leu Val Cys
            260                 265                 270

Ala Glu Cys Ala Pro Gly Leu Gln Leu Cys Pro Ile Cys Arg Ala Pro
        275                 280                 285

Val Arg Ser Arg Val Arg Thr Phe Leu Ser
    290                 295

<210> SEQ ID NO 28
<211> LENGTH: 1268
<212> TYPE: DNA
<213> ORGANISM: homo sapiens
<220> FEATURE:
<221> NAME/KEY: CDS
<222> LOCATION: (174)...(1016)

<400> SEQUENCE: 28
ccctgggata ctcccctccc agggtgtctg gtggcaggcc tgtgcctatc cctgctgtcc      60
ccagggtggg ccccgggggt caggagctcc agaagggcca gctgggcata ttctgagatt    120
ggccatcagc ccccatttct gctgcaaacc tggtcagagc cagtgttccc tcc atg       176
                                                            Met
                                                              1 gga cct aaa gac agt gcc aag tgc ctg cac cgt gga cca cag ccg agc      224
Gly Pro Lys Asp Ser Ala Lys Cys Leu His Arg Gly Pro Gln Pro Ser
          5                  10                  15 cac tgg gca gcc ggt gat ggt ccc acg cag gag cgc tgt gga ccc cgc      272
His Trp Ala Ala Gly Asp Gly Pro Thr Gln Glu Arg Cys Gly Pro Arg
        20                  25                  30 tct ctg ggc agc cct gtc cta ggc ctg gac acc tgc aga gcc tgg gac      320
Ser Leu Gly Ser Pro Val Leu Gly Leu Asp Thr Cys Arg Ala Trp Asp
 35                  40                  45 cac gtg gat ggg cag atc ctg ggc cag ctg cgg ccc ctg aca gag gag      368
His Val Asp Gly Gln Ile Leu Gly Gln Leu Arg Pro Leu Thr Glu Glu
 50                  55                  60                  65 gaa gag gag gag ggc gcc ggg gcc acc ttg tcc agg ggg cct gcc ttc      416
Glu Glu Glu Glu Gly Ala Gly Ala Thr Leu Ser Arg Gly Pro Ala Phe
                 70                  75                  80 ccc ggc atg ggc tct gag gag ttg cgt ctg gcc tcc ttc tat gac tgg      464
Pro Gly Met Gly Ser Glu Glu Leu Arg Leu Ala Ser Phe Tyr Asp Trp
             85                  90                  95 ccg ctg act gct gag gtg cca ccc gag ctg ctg gct gct gcc ggc ttc      512
Pro Leu Thr Ala Glu Val Pro Pro Glu Leu Leu Ala Ala Ala Gly Phe
        100                 105                 110 ttc cac aca ggc cat cag gac aag gtg agg tgc ttc ttc tgc tat ggg      560
Phe His Thr Gly His Gln Asp Lys Val Arg Cys Phe Phe Cys Tyr Gly
    115                 120                 125 ggc ctg cag agc tgg aag cgc ggg gac gac ccc tgg acg gag cat gcc      608
Gly Leu Gln Ser Trp Lys Arg Gly Asp Asp Pro Trp Thr Glu His Ala
130                 135                 140                 145 aag tgg ttc ccc agc tgt cag ttc ctg ctc cgg tca aaa gga aga gac      656
Lys Trp Phe Pro Ser Cys Gln Phe Leu Leu Arg Ser Lys Gly Arg Asp
                150                 155                 160 ttt gtc cac agt gtg cag gag act cac tcc cag ctg ctg ggc tcc tgg      704
Phe Val His Ser Val Gln Glu Thr His Ser Gln Leu Leu Gly Ser Trp
            165                 170                 175
```

```
gac ccg tgg gaa gaa ccg gaa gac gca gcc cct gtg gcc ccc tcc gtc      752
Asp Pro Trp Glu Glu Pro Glu Asp Ala Ala Pro Val Ala Pro Ser Val
        180                 185                 190 cct gcc tct ggg tac cct gag ctg ccc aca ccc agg aga gag gtc cag      800
Pro Ala Ser Gly Tyr Pro Glu Leu Pro Thr Pro Arg Arg Glu Val Gln
    195                 200                 205 tct gaa agt gcc cag gag cca gga gcc agg gat gtg gag gcg cag ctg      848
Ser Glu Ser Ala Gln Glu Pro Gly Ala Arg Asp Val Glu Ala Gln Leu
210                 215                 220                 225 cgg cgg ctg cag gag gag agg acg tgc aag gtg tgc ctg gac cgc gcc      896
Arg Arg Leu Gln Glu Glu Arg Thr Cys Lys Val Cys Leu Asp Arg Ala
            230                 235                 240 gtg tcc atc gtc ttt gtg ccg tgc ggc cac ctg gtc tgt gct gag tgt      944
Val Ser Ile Val Phe Val Pro Cys Gly His Leu Val Cys Ala Glu Cys
        245                 250                 255 gcc ccc ggc ctg cag ctg tgc ccc atc tgc aga gcc ccc gtc cgc agc      992
Ala Pro Gly Leu Gln Leu Cys Pro Ile Cys Arg Ala Pro Val Arg Ser
    260                 265                 270 cgc gtg cgc acc ttc ctg tcc tag gccaggtgcc atggccggcc aggtgggctg     1046
Arg Val Arg Thr Phe Leu Ser  *
275                 280 cagagtgggc tccctgcccc tctctgcctg ttctggactg tgttctgggc ctgctgagga    1106
tggcagagct ggtgtccatc cagcactgac cagccctgat tccccgacca ccgcccaggg    1166
tggagaagga ggcccttgct tggcgtgggg gatggcttaa ctgtacctgt ttggatgctt    1226
ctgaatagaa ataaagtggg ttttccctgg aggtacccag ca                        1268
```

<210> SEQ ID NO 29
<211> LENGTH: 280
<212> TYPE: PRT
<213> ORGANISM: homo sapiens

<400> SEQUENCE: 29

```
Met Gly Pro Lys Asp Ser Ala Lys Cys Leu His Arg Gly Pro Gln Pro
1               5                   10                  15

Ser His Trp Ala Ala Gly Asp Gly Pro Thr Gln Glu Arg Cys Gly Pro
            20                  25                  30

Arg Ser Leu Gly Ser Pro Val Leu Gly Leu Asp Thr Cys Arg Ala Trp
        35                  40                  45

Asp His Val Asp Gly Gln Ile Leu Gly Gln Leu Arg Pro Leu Thr Glu
    50                  55                  60

Glu Glu Glu Glu Gly Ala Gly Ala Thr Leu Ser Arg Gly Pro Ala
65                  70                  75                  80

Phe Pro Gly Met Gly Ser Glu Glu Leu Arg Leu Ala Ser Phe Tyr Asp
                85                  90                  95

Trp Pro Leu Thr Ala Glu Val Pro Pro Glu Leu Leu Ala Ala Ala Gly
            100                 105                 110

Phe Phe His Thr Gly His Gln Asp Lys Val Arg Cys Phe Phe Cys Tyr
        115                 120                 125

Gly Gly Leu Gln Ser Trp Lys Arg Gly Asp Asp Pro Trp Thr Glu His
    130                 135                 140

Ala Lys Trp Phe Pro Ser Cys Gln Phe Leu Arg Ser Lys Gly Arg
145                 150                 155                 160

Asp Phe Val His Ser Val Gln Glu Thr His Ser Gln Leu Leu Gly Ser
                165                 170                 175

Trp Asp Pro Trp Glu Glu Pro Glu Asp Ala Ala Pro Val Ala Pro Ser
```

-continued

```
                180                     185                     190
Val Pro Ala Ser Gly Tyr Pro Glu Leu Pro Thr Pro Arg Arg Glu Val
            195                     200                 205

Gln Ser Glu Ser Ala Gln Glu Pro Gly Ala Arg Asp Val Glu Ala Gln
        210                     215                 220

Leu Arg Arg Leu Gln Glu Glu Arg Thr Cys Lys Val Cys Leu Asp Arg
225                     230                 235                     240

Ala Val Ser Ile Val Phe Val Pro Cys Gly His Leu Val Cys Ala Glu
                245                     250                 255

Cys Ala Pro Gly Leu Gln Leu Cys Pro Ile Cys Arg Ala Pro Val Arg
            260                     265                 270

Ser Arg Val Arg Thr Phe Leu Ser
        275                 280
```

DNA VACCINES AGAINST TUMOR GROWTH AND METHODS OF USE THEREOF

CROSS-REFERENCE TO RELATED APPLICATIONS

This application is a division of U.S. patent application Ser. No. 10/807,897, filed on Mar. 24, 2004, which claims the benefit of U.S. Provisional Patent Application No. 60/457,009, filed on Mar. 24, 2003, each of which is incorporated herein by reference.

GOVERNMENTAL RIGHTS

A portion of the work described herein was supported by grant number CA83856 from the National Institutes of Health, and grant numbers BC031079, DAMD 17-02-1-0137 and DAMD 17-02-1-0562 from the Department of Defense. The United States Government has certain rights in this invention.

INCORPORATION OF SEQUENCE LISTING

This application includes biological sequence information, which is set forth in an ASCII text file having the file name "TSRI8741SEQ.TXT", created on Mar. 24, 2004, and having a file size of 51,968 bytes, which is incorporated herein by reference.

FIELD OF THE INVENTION

This invention relates to deoxyribonucleic acid (DNA) vaccines encoding suitable molecules effective for eliciting an immune response against tumor cells. More particularly this invention relates to DNA vaccines encoding for a cancer-associated Inhibitor of Apoptosis-family (IAP) protein, and an immunoactive gene product. This invention also relates to methods of using the DNA vaccines to inhibit tumor growth.

BACKGROUND OF THE INVENTION

Vaccines have been utilized to provide a long term protection against a number of disease conditions by very limited administration of a prophylactic agent that stimulates an organism's immune system to destroy disease pathogens before they can proliferate and cause a pathological effect. Various approaches to vaccines and vaccinations are described in Bernard R. Glick and Jack J. Pasternak, *Molecular Biotechnology, Principles and Applications of Recombinant DNA*, Second Edition, ASM Press pp. 253-276 (1998).

Vaccination is a means of inducing the body's own immune system to seek out and destroy an infecting agent before it causes a pathological response. Typically, vaccines are either live, but attenuated, infectious agents (virus or bacteria), or a killed form of the agent. A vaccine consisting of a live bacteria or virus must be non-pathogenic. Typically, a bacterial or viral culture is attenuated (weakened) by physical or chemical treatment. Although the agent is non-virulent, it can still elicit an immune response in a subject treated with the vaccine.

An immune response is elicited by antigens, which can be either specific macromolecules or an infectious agent. These antigens are generally either proteins, polysaccharides, lipids, or glycolipids, which are recognized as "foreign" by lymphocytes known as B cells and T cells. Exposure of both types of lymphocytes to an antigen elicits a rapid cell division and differentiation response, resulting in the formation of clones of the exposed lymphocytes. B cells produce plasma cells, which in turn, produce proteins called antibodies (Ab), which selectively bind to the antigens present on the infectious agent, thus neutralizing or inactivating the pathogen (humoral immunity). In some cases, B cell response requires the assistance of CD4 helper T cells.

The specialized T cell clone that forms in response to the antigen exposure is a cytotoxic T lymphocyte (CTL), which is capable of binding to and eliminating pathogens and tissues that present the antigen (cell-mediated or cellular immunity). In some cases, an antigen presenting cell (APC) such as a dendritic cell, will envelop a pathogen or other foreign cell by endocytosis. The APC then processes the antigens from the cells and presents these antigens in the form of a histocompatibility molecule:peptide complex to the T cell receptor (TCR) on CTLs, thus stimulating an immune response.

Humoral immunity characterized by the formation of specific antibodies is generally most effective against acute bacterial infections and repeat infections from viruses, whereas cell-mediated immunity is most effective against viral infection, chronic intracellular bacterial infection, and fungal infection. Cellular immunity is also known to protect against cancers and is responsible for rejection of organ transplants.

Antibodies to antigens from prior infections remain detectable in the blood for very long periods of time, thus affording a means of determining prior exposure to a pathogen. Upon re-exposure to the same pathogen, the immune system effectively prevents reinfection by eliminating the pathogenic agent before it can proliferate and produce a pathogenic response.

The same immune response that would be elicited by a pathogen can also sometimes be produced by a non-pathogenic agent that presents the same antigen as the pathogen. In this manner, the subject can be protected against subsequent exposure to the pathogen without having previously fought off an infection.

Not all infectious agents can be readily cultured and inactivated, as is required for vaccine formation, however. Modern recombinant DNA techniques have allowed the engineering of new vaccines to seek to overcome this limitation. Infectious agents can be created that lack the pathogenic genes, thus allowing a live, nonvirulent form of the organism to be used as a vaccine. It is also possible to engineer a relatively nonpathogenic organism such as *E. coli* to present the cell surface antigens of a pathogenic carrier. The immune system of a subject vaccinated with such a transformed carrier is "tricked" into forming antibodies to the pathogen. The antigenic proteins of a pathogenic agent can be engineered and expressed in a nonpathogenic species and the antigenic proteins can be isolated and purified to produce a "subunit vaccine." Subunit vaccines have the advantage of being stable, safe, and chemically well defined; however, their production can be cost prohibitive.

A new approach to vaccines has emerged in recent years, broadly termed genetic immunization. In this approach, a gene encoding an antigen of a pathogenic agent is operably inserted into cells in the subject to be immunized. The treated cells, preferably antigen presenting cells (APCs) such as the dendritic cells, are transformed and produce the antigenic proteins of the pathogen. These in vivo-produced antigens then trigger the desired immune response in the host. The genetic material utilized in such genetic vaccines can be either a DNA or RNA construct. Often the polynucleotide encoding the antigen is introduced in combination with other promoter polynucleotide sequences to enhance insertion, replication, or expression of the gene.

DNA vaccines encoding antigen genes can be introduced into the host cells of the subject by a variety of delivery systems. These delivery systems include prokaryotic and viral delivery systems. For example, one approach is to utilize a viral vector, such as vaccinia virus incorporating the new genetic material, to innoculate the host cells. Alternatively, the genetic material can be incorporated in a plasmid vector or can be delivered directly to the host cells as a "naked" polynucleotide, i.e. simply as purified DNA. In addition, the DNA can be stably transfected into attenuated bacteria such as *Salmonella typhimurium*. When a patient is orally vaccinated with the transformed *Salmonella*, the bacteria are transported to Peyer's patches in the gut (i.e., secondary lymphoid tissues), which then stimulate an immune response.

DNA vaccines provide an opportunity to immunize against disease states that are not caused by traditional pathogens, such as genetic diseases and cancer. Typically, a genetic cancer vaccine introduces into APCs a gene that encodes an antigen, and the so transformed APCs produce antigens to a specific type of tumor cell. An effective general vaccine against a number of cancer types can thus entail numerous individual vaccines for each type of cancer cell to be immunized against.

Inhibitor of Apoptosis Proteins (i.e., IAP-family proteins) are a class of natural antigens expressed in many different tumor cells. As the name suggests, these proteins, in their natural form, inhibit apoptosis (i.e., programmed cell death), which in turn, may lead to resistance of cancer cells to apoptosis inducing chemotherapeutic agents, such as etoposide. Examples of IAP-family proteins include X chromosome-associated IAP (XIAP), NAIP, cIAP1 (also known as BIRC2), cIAP2 (also known as BIRC3), bruce (also known as BIRC6), survivin (also known as BIRC5), and livin (also known as BIRC7, KIAP, and ML-IAP). The mammalian IAP family of proteins includes proteins with three BIR domains (e.g., XIAP, cIAP1, cIAP2, and NAIP), as well as proteins with a single BIR domain (e.g., survivin and livin).

Tamm et al. *Cancer Res.* 1998; 58(23):5315-20, have reported expression of the human survivin in 60 human tumor cell lines. Tamm et al. have also reported that survivin and XIAP were both effective at inhibiting programmed cell death (apoptosis) induced by treatment of tumor cells with apoptosis inducing agents such as Bax or Fas (CD95). Survivin and other IAP-family proteins reportedly inhibit apoptosis by binding to effector cell death proteases, e.g., caspase-3 and caspase-7. Mutations in IAP-family proteins can lead to reduced apoptosis inhibition activity or even to apoptosis inducing activity relative to the activity of the wild-type IAP-family protein. The anti-apoptotic activity of the IAP-family proteins is believed to be associated with the BIR domain.

Survivin reportedly is present in most common human cancer cells, including cancers of the lung, prostate, breast, and pancreas. Survivin has also been identified in high-grade, non-Hodgkin's lymphomas, but not in low-grade non-Hodgkin's lymphomas. Reportedly, survivin is present in normal cells during fetal development, but unlike most other IAP-family proteins, survivin is virtually undetectable in normal adult human tissues. See Ambrosini et al. *Nat. Med.* 1997; 3(8):917-21.

Livin has been detected in some adult tissues and in embryonic tissues. Elevated levels of livin expression have been reported in melanomas, colon cancer cells, bladder cancer cells, and lung cancer cells. Two splice variants of livin have been reported, both of which contain a single BIR domain. The full length alpha variant has 298 amino acid residues, whereas the beta variant has 280 amino acid residues.

IAP-family proteins also have been identified in a number of species in addition to humans, including mammals such as the mouse, amphibians such as *Xenopus* species (African clawed toads), insects such as *Drosophila* species, and baculoviruses.

The ubiquitous and highly selective nature of survivin expression in cancer cells makes it a potentially useful diagnostic marker for cancer. For example, Rohayem et al. *Cancer Res.* 2000; 60:1815-17, have reportedly identified auto-antibodies to survivin in human lung and colorectal cancer patients.

Survivin has also been identified as a target for cancer therapy. The inhibiting effect of survivin on caspase-3 and caspase-7 has been implicated in the resistance of cancer cells to various apoptosis stimulating chemotherapeutic treatments. An antisense oligonucleotide that targets survivin expression has been reported to down-regulate survivin expression in an adenocarcinoma cell line and sensitize the cancer cells to the chemotherapeutic agent etoposide. See Olie et al. *Cancer Res.* 2000; 60:2805-9; and Mesri et al. *J. Clinical Res.*, 2001; 108:981-990.

Cytokines are proteins and polypeptides produced by cells that can affect the behavior of other cells, such as cell proliferation, cell differentiation, regulation of immune responses, hematopoiesis, and inflammatory responses. Cytokines have been classified into a number of families, including chemokines, hematopoietins, immunoglobulins, tumor necrosis factors, and a variety of unassigned molecules. See generally *Oxford Dictionary of Biochemistry and Molecular Biology*, Revised Edition, Oxford University Press, 2000; and C. A. Janeway, P. Travers, M. Walport and M. Schlomchik, *Immunobiology*, Fifth Edition, Garland Publishing, 2001 (hereinafter Janeway and Travers). A concise classification of cytokines is presented in Janeway and Travers, Appendix III, pages 677-679, the relevant disclosures of which are incorporated herein by reference.

Hematopoietins include, for example erythropoietin, interleukin-2 (IL-2, a 133 amino acid protein produced by T cells and involved in T cell proliferation), IL-3, IL-4, IL-5, IL-6, IL-7, IL-9, IL-11, IL-13, IL-15 (a 114 amino acid IL-2-like protein, which stimulates the growth of intestinal epithelium, T cells, and NK cells), granulocyte colony-stimulating factor (G-CSF), granulocyte-macrophage colony-stimulating factor (GM-CSF), oncostatin M (OSM), and leukemia inhibitory factor (LIF).

Interferons include, for example, IFN-$\alpha$, IFN-$\beta$, and IFN-$\gamma$ (a 143 amino acid homodimeric protein produced by T cells and NK cells, which is involved in macrophage activation, increased expression of MHC molecules and antigen processing components, IG class switching, and suppression of $T_H2$).

Immunoglobulins include, for example, B7.1 (CD80), and B7.2 (CD86), both of which co-stimulate T cell responses.

The tumor necrosis factor (TNF) family includes, for example, TNF-$\alpha$, TNF-$\beta$ (lymphotoxin), lymphotoxin-$\beta$ (LT-$\beta$), CD40 ligand, Fas ligand, CD27 ligand, CD30 ligand, 4-1BB ligand, Trail, and OPG ligand.

Various cytokines that are not assigned to a particular family include, for example, tumor growth factor-$\beta$ (TGF-$\beta$), IL-1$\alpha$, IL-1$\beta$, IL-1 RA, IL-10, IL-12 (natural killer cell stimulatory factor; a heterodimer having a 197 amino acid chain and a 306 amino acid chain, which is involved in NK cell activation and induction of T cell differentiation to $T_H1$-like cells), macrophage inhibitory factor (MIF), IL-16, IL-17 (a cytokine production-inducing factor, which induces cytokine production in epithelia, endothelia, and fibroblasts), and IL-18.

Chemokines are a family of cytokines that are relatively small chemoattractant proteins and polypeptides, which stimulate the migration and activation of various cells, such as leucocyte migration (e.g., phagocytes and lymphocytes). Chemokines play a role in inflammation and other immune responses. Chemokines have been classified into a number of families, including the C chemokines, CC chemokines, CXC chemokines, and $CX_3C$ chemokines. The names refer to the number and spacing of cysteine residues in the molecules; C chemokines having one cysteine, CC chemokines having two contiguous cysteines, CXC having two cysteines separated by a single amino acid residue, and $CX_3C$ chemokines having two cysteines separated by three amino acid residues. Chemokines interact with a number of chemokine receptors present on cell surfaces. See Janeway and Travers, Appendix IV, page 680, the relevant disclosures of which are incorporated herein by reference.

In addition, chemokines can have immunomodulating activity and have been implicated in immune responses to cancer. For example, murine 6Ckine/SLC, the mouse analog of the human secondary lymphoid tissue chemokine (SLC), now commonly referred to as CCL21, has been reported to induce an antitumor response in a C-26 colon carcinoma tumor cell line. See Vicari, et al. *J. Immunol.* 2000; 165(4): 1992-2000. Human CCL21 and its murine counterpart, 6Ckine/SLC, are classified as CC chemokines, which interact with the CCR7 chemokine receptor. Murine 6Ckine/SLC (muCCL21) is also reported by Vicari et al. to be a ligand for the CXCR3 chemokine receptor. Human CCL21, murine muCCL21 and a variety of other chemokines are implicated in the regulation of various immune system cells such as dendritic cells, T-cells, and natural killer (NK) cells.

Mig and IP-10 are CXC chemokines that interact with the CXCR3 receptor, which is associated with activated T cells. Lymphotactin is a C chemokine, which intereacts with the XCR1 receptor associated with T cells and NK cells. Fractalkine is a $CX_3C$ chemokine, which interact with the $CX_3CR1$ receptor that is associated with T cells, monocytes and neutrophils.

NK cells are large granular lymphocytes that recognize and destroy cells that have been infected with a virus. NK cells can be regulated by interaction of immunomodulating polypeptide ligands with receptors on the NK cell surface. For example, ligands for the NKG2D receptor that can regulate NK cell activity, include chemokines such as muCCL21, and stress-inducible polypeptide ligands such as MHC class I chain-related antigens and UL16 binding proteins. Murine H60 minor histocompatibility antigen peptide is reported to bind to the NKG2D receptor, as well. See, e.g., Robertson et al. *Cell Immunol.* 2000; 199(1):8-14; Choi et al. *Immunity* 2002, 17(5):593-603, and Farag et al., Blood, 2002; 100(6):1935-1947.

The present invention fulfills an ongoing need for vaccines that can stimulate a general immune response against cancer cells by providing a DNA vaccine encoding a cancer-associated IAP-family protein and an immunoactive gene product in a single vector.

SUMMARY OF THE INVENTION

A DNA vaccine effective for eliciting an immune response against cancer cells comprises a DNA construct operably encoding a cancer-associated IAP-family protein and an immunoactive gene product in a pharmaceutically acceptable carrier. Preferably, the DNA construct is operably incorporated in a vector such as an attenuated bacterium (e.g., an attenuated *Salmonella typhimurium* vector). The DNA vaccine includes a polynucleotide that encodes at least one cancer-associated IAP-family protein together with a polynucleotide that encodes an immunoactive gene product. Preferably the DNA construct encodes a cancer-associated IAP-family protein that is substantially absent from adult tissues, but which is elevated in cancer tissues, such as a survivin protein (e.g., a human survivin, murine survivin, and the like), or a livin protein. Preferably the immunoreactive gene product encoded by the DNA construct is a cytokine, a ligand for a natural killer cell surface receptor, or a similar immunoreactive molecule.

In one embodiment, the DNA vaccine preferably comprises a DNA that operably encodes a survivin protein selected from the group consisting of (a) wild-type human survivin having the amino acid residue sequence of SEQ ID NO: 2, (b) an immunogenic homolog of wild-type human survivin having an amino acid residue sequence at least 80% identical to SEQ ID NO: 2, (c) a splice variant of human survivin having the amino acid residue sequence of SEQ ID NO: 23, (d) a splice variant of human survivin having the amino acid residue sequence of SEQ ID NO: 24, and (e) a fragment of a survivin protein that binds to a MHC class l molecule and is recognized by cytotoxic T cells.

In yet another embodiment, the DNA vaccine preferably comprises a DNA construct that operably encodes a livin protein selected from the group consisting of (a) full length wild-type human livin alpha splice variant having the amino acid residue sequence of SEQ ID NO: 27, (b) human livin beta splice variant having the amino acid residue sequence of SEQ ID NO: 29, (c) an immunogenic homolog of full length wild-type human livin having an amino acid residue sequence at least 80% identical to SEQ ID NO: 27, (d) an immunogenic homolog of wild-type human livin beta splice variant having an amino acid residue sequence at least 80% identical to SEQ ID NO: 29, and (e) a fragment of a livin protein that binds to a MHC class I molecule and is recognized by cytotoxic T cells.

Preferred cytokines include chemokines, such as human CCL21, murine CCL21, lymphotactin, fractalkine, IP-10, and the like, hematopoietins, such as IL-2, IL-15, and the like; interferons, such as IFN-γ and the like; as well as other cytokines associated with T cell and NK cell migration or proliferation, such as IL-12, IL-17 and the like.

Preferred natural killer cell surface receptor ligands are stress-inducible proteins such as human MICA, human MICB, human ULBP1, human ULBP2, human ULBP3, and the like, which bind to the NKG2D cell surface receptor. Particularly preferred NKG2D ligands are MICA and MICB.

Conventional adjuvants such as alum, oil-in-water emulsions, preservatives, and the like, can be present in the vaccines, as well. The DNA vaccines of the present invention stimulate an immune response against tumor cells, including stimulation of tumor cell apoptosis, thus inhibiting tumor growth and metastases.

In a method aspect of the present invention, a DNA vaccine is utilized to provide long term inhibition of tumor growth in a vaccinated patient. A DNA vaccine comprising a polynucleotide construct operably encoding a IAP-family protein and an immunoactive gene product in a pharmaceutically acceptable carrier is administered (preferably orally)

to a patient in need of inhibition of tumor growth in an amount that is sufficient to elicit an immune response against tumor cells.

The vaccines of the present invention are useful for treatment of various types of cancers. For example, a patient suffering from a lung cancer, colorectal cancer, melanoma, and the like, can benefit from immunization by the vaccines of the present invention.

BRIEF DESCRIPTION OF THE DRAWINGS

In the Drawings, FIG. 1 depicts the nucleic acid sequence encoding human survivin, SEQ ID NO: 1;

FIG. 2 depicts the amino acid residue sequence of human survivin, SEQ ID NO: 2;

FIG. 3 depicts the nucleic acid sequence encoding murine TIAP, SEQ ID NO: 3;

FIG. 4 depicts the amino acid residue sequence of murine TIAP, SEQ ID NO: 4;

FIG. 5 depicts the protein homology between human survivin and murine TIAP;

FIG. 6 depicts the nucleic acid sequence encoding human SLC (CCL21), SEQ ID NO: 5;

FIG. 7 depicts the amino acid residue sequence of human SLC (CCL21), SEQ ID NO: 6;

FIG. 8 depicts the nucleic acid sequence encoding murine6Ckine/SLC (muCCL21), SEQ ID NO: 7;

FIG. 9 depicts the amino acid residue sequence of murine 6Ckine/SLC (muCCL21), SEQ ID NO: 8;

FIG. 10 depicts the protein homology between human SLC (CCL21) and murine 6Ckine/SLC (muCCL21);

FIG. 11 depicts a partial nucleic acid sequence encoding murine minor histocompatibility antigen peptide H60, SEQ ID NO: 9;

FIG. 12 depicts a partial amino acid residue sequence of minor histocompatibility antigen peptide H60, SEQ ID NO: 10;

FIG. 25 illustrates the nucleic acid sequence encoding the CCL21b variant of 6CKine/SLC, SEQ ID NO: 11;

FIG. 26 illustrates the amino acid residue sequence of the CCL21b variant of 6CKine/SLC, SEQ ID NO: 12;

FIG. 27 illustrates the nucleic acid sequence encoding the human MICA, SEQ ID NO: 13;

FIG. 28 illustrates the amino acid residue sequence of the human MICA, SEQ ID NO: 14;

FIG. 29 illustrates the nucleic acid sequence encoding the human MICB, SEQ ID NO: 15;

FIG. 30 illustrates the amino acid residue sequence of the human MICB, SEQ ID NO: 16;

FIG. 31 illustrates the nucleic acid sequence encoding the human ULBP1, SEQ ID NO: 17;

FIG. 32 illustrates the amino acid residue sequence of the human ULBP1, SEQ ID NO: 18;

FIG. 33 illustrates the nucleic acid sequence encoding the human ULBP2, SEQ ID NO: 19;

FIG. 34 illustrates the amino acid residue sequence of the human ULBP2, SEQ ID NO: 20;

FIG. 35 illustrates the nucleic acid sequence encoding the human ULBP3, SEQ ID NO: 21;

FIG. 36 illustrates the amino acid residue sequence of the human ULBP3, SEQ ID NO: 22;

FIG. 37 illustrates the amino acid residue sequence of the human survivin splice variant survivin-2B (SEQ ID NO: 23) and splice variant survivin-ΔEx3 (SEQ ID NO:24);

FIG. 38 is reproduction of GENBANK record for Accession No. NP 005922, describing allelic variants of MICB;

FIG. 39 depicts the nucleic acid sequence encoding full length human livin alpha splice variant, SEQ ID NO: 26;

FIG. 40 depicts the amino acid residue sequence of human livin alpha splice variant, SEQ ID NO: 27;

FIG. 41 depicts the nucleic acid sequence encoding human livin beta splice variant, SEQ ID NO: 28; and FIG. 42 depicts the amino acid residue sequence of human livin beta splice variant, SEQ ID NO: 29.

DETAILED DESCRIPTION OF PREFERRED EMBODIMENTS

Figure 13:
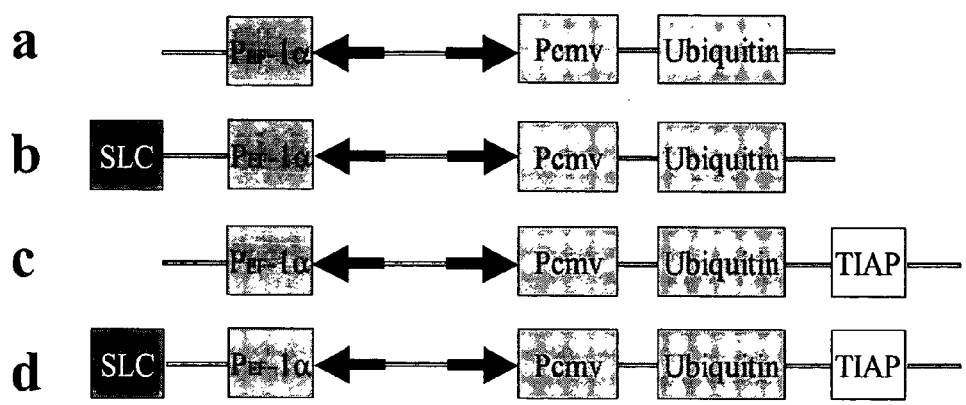
FIG. 13 is a schematic representation of DNA constructs encoding a survivin protein (murine survivin, also known as TIAP) and an immunomodulating chemokine (CCL21, also known as SLC) in a pBudCE4.1 vector.

A DNA vaccine effective for eliciting an immune response against tumor cells comprises a DNA construct that operably encodes an IAP-family protein and an immunoactive gene product. The term "DNA construct" as used herein and in the appended claims means a synthetic DNA structure that can be transcribed in target cells. The construct can comprise a linear nucleic acid such as a purified DNA, a DNA incorporated in a plasmid vector, or a DNA incorporated into any other vector suitable for introducing DNA into a host cell. Preferably, the DNA is incorporated in a viral or bacterial vector, more preferably an attenuated viral or bacterial vector that is non-pathogenic, most preferably in an attenuated bacterial vector.

As used herein, the term "immunity" refers to long term immunological protection against the virulent form of the infectious agent or tumor antigen. The term "immunization" refers to prophylactic exposure to an antigen of a pathogenic agent derived from a non-virulent source, which results in immunity to the pathogen in the treated subject.

The term "antibody", as used herein, refers to a molecule that is a glycosylated protein, an immunoglobulin, which specifically binds to an antigen.

The term "antigen", as used herein, denotes an entity that, when introduced into an immunocompetent animal, stimulates production of specific antibody or antibodies that can combine with the antigen. The term "immunogen", as used herein, denotes an entity that is not by itself able to stimulate antibody production but may do so if combined with a carrier.

The term "conservative substitution", as used herein, denotes replacement of one amino acid residue by another, biologically similar residue. Examples of conservative substitutions include the substitution of one hydrophobic residue such as isoleucine, valine, leucine or methionine for another, or the substitution of one hydrophilic residue such as arginine for lysine and vice versa, glutamic acid for aspartic acid vice versa, or glutamine for asparagine and vice versa, and the like.

The term "substantially corresponds" in its various grammatical forms as used herein relating to peptide sequences means a peptide sequence as described plus or minus up to three amino acid residues at either or both of the amino- and carboxy-termini and containing only conservative substitutions along the polypeptide sequence.

The term "immunoactive gene product" and grammatical variations thereof, as used herein and in the appended claims, includes proteins and polypeptides having an immunomodulating activity, such as proteins and polypeptides that interact with, and modulate the activity of T cells and NK cells.

The term "IAP-family protein" as used herein and in the appended claims includes any of the class of natural antigens expressed in tumor cells, which inhibit apoptosis in their natural form. IAP-family proteins include, for example, human survivin, human X chromosome-linked IAP (XIAP), murine TIAP (the murine analog of survivin), human livin, human c-IAP-1, human c-IAP-2, human NAIP, any other protein that includes at least one baculoviral inhibitor of apoptosis repeat (BIR) domain, or a homolog thereof. The BIR domain is present in all wild-type IAP-family proteins. It includes four relatively short alpha-helices and a region of three stranded anti-parallel beta sheet structure. The domain binds Zn using three cysteine residues and a histidine residue, which are conserved across IAP-family proteins. The term "IAP-family protein" as used herein and in the appended claims also includes variants of wild-type IAP proteins such as splice variants and substitution variants, and the like, as well as fragments and immunogenic homologs thereof that bind to a major histocompatibility (MHC) class I molecule and are recognized by cytotoxic T-cells (i.e., survivin protein epitopes).

The term "cancer-associated" as used herein and in the appended claims, in reference to IAP-family proteins means an IAP-family protein that is expressed at elevated levels in cancer cells than it is in normal, non-cancerous cells.

Examples of cancer-associated IAP-family proteins include, without limitation, human survivin and human livin.

The term "survivin protein" as used herein and in the appended claims includes the full length human survivin molecule (SEQ ID NO: 2), the full length murine analog thereof (i.e., TIAP, as described herein), variants of human survivin or murine survivin, such as splice variants and substitution variants, as well as fragments (e.g., epitopes) of human survivin and immunogenic homologs of human survivin that bind to a major histocompatibility (MHC) class I molecule and are recognized by cytotoxic T cells. Known substitution variants of human survivin include a protein having the substitution T34A in the amino acid residue sequence of SEQ ID NO:2, a protein having the substitution D53A in the amino acid residue sequence of SEQ ID NO:2, and a protein having the substitution C84A in the amino acid residue sequence of SEQ ID NO:2 (see Song et al., *Mol. Biol. Cell,* 2004; 15(3):1287-1296, E-publication Dec. 29, 2003). Each of these known variants has apoptotic activity, in contrast to wild-type survivin which has anti-apototic activity.

In a preferred embodiment, the DNA vaccine of the present invention comprises a DNA construct that operably encodes a survivin protein such as wild-type human survivin having the amino acid residue sequence of SEQ ID NO: 2, an immunogenic homolog of wild-type human survivin having an amino acid residue sequence at least 80% identical to SEQ ID NO: 2, a splice variant of human survivin having the amino acid residue sequence of SEQ ID NO: 23, a splice variant of human survivin having the amino acid residue sequence of SEQ ID NO: 24, and a fragment of a survivin protein that binds to a MHC class I molecule and is recognized by cytotoxic T cells.

The term "livin protein" as used herein and in the appended claims includes the full length human livin alpha splice variant (SEQ ID NO: 27), the beta splice variant of human livin (SEQ ID NO: 29), substitution variants of human livin alpha and beta splice variants, as well as fragments and immunogenic homologs thereof that bind to a MHC Class I molecule and are recognized by cytotoxic T-cells.

In another preferred embodiment, the DNA vaccine of the present invention comprises a DNA construct that operably encodes a livin protein such as full length wild-type human livin alpha splice variant having the amino acid residue sequence of SEQ ID NO: 27, human livin beta splice variant having the amino acid residue sequence of SEQ ID NO: 29, an immunogenic homolog of full length wild-type human livin having an amino acid residue sequence at least 80% identical to SEQ ID NO: 27, an immunogenic homolog of wild-type human livin beta splice variant having an amino acid residue sequence at least 80% identical to SEQ ID NO: 29, and a fragment of a livin protein that binds to a MHC class I molecule and is recognized by cytotoxic T cells.

As used herein and in the appended claims, the term "immunogenic homolog" and grammatical variations thereof, when used in reference to cancer-associated IAP-family proteins such as survivin and livin, means a protein having a high degree of homology to a wild-type cancer-associated IAP-family protein and which can bind to a MHC Class I molecule and can be recognized by cytotoxic T-cells that are active against the corresponding wild-type IAP family protein. Preferably the immunogenic homologs have an amino acid residue sequence that is at least about 80% identical to the amino acid sequence of the wild-type cancer-associated IAP-family protein, more preferably at least about 90% identical, most preferably at least about 95% identical.

Without being bound by theory, it is believed that vaccination of a patient, such as a human patient, with a vaccine of the invention leads to selective presentation of antigens derived from cancer-associated IAP-family protein on the surface of immune cells, such as antigen presenting cells, and in addition to the selective expression of the immunoactive gene product in these cells. Increased presentation of the cancer-associated IAP-family protein, such as a survivin protein or livin protein on the cell surface of the antigen presenting cell, in combination with expression of an immunoactive gene product, such as a cytokine or a ligand for a NK cell surface receptor, leads to an enhanced immune response against cancer cells that express cancer-associated IAP-family proteins, such as a survivin protein or livin protein. In adult humans, survivin is expressed almost exclusively in cancer cells. Similarly, livin expression is reportedly elevated in some cancer cell lines, particularly melanoma cell lines.

In a preferred embodiment, the DNA vaccine comprises a polynucleotide sequence that operably encodes a survivin protein and a cytokine Preferably, the survivin protein is human survivin, a murine survivin, or an epitope thereof. Preferably the cytokine modulates T cell or NK cell activity. Preferred cytokines include chemokines, hematopoietins, and interferons. Other preferred cytokines include NK cell activating cytokines such as IL-12 and cytokine production-stimulating factors such as IL-17.

In another preferred embodiment the DNA vaccine comprises a polynucleotide sequence that operably encodes a livin protein and a cytokine. Preferably the livin protein is wild-type human livin or an epitope thereof. Preferably the cytokine modulates T-cell or NK cell activity. Preferred cytokines include, chemokines, hematopoietins and interferons. Other preferred cytokines include NK cell activating cytokines such as IL-12 and cytokine production-stimulating factors such as IL-17.

Preferred chemokines include CC chemokines, particularly those which are ligands for the CCR7 chemokine receptor, such as CCL21 (SLC) and the like; C chemokines that are ligands for the CR1 receptor, such as lymphotactin, and the like; $CX_3C$ chemokines that are ligands for the $CX_3CR1$ receptor, such as fractalkine, and the like; CXC chemokines, particularly those which are ligands for the CXCR3 receptor, such as IP-10 and the like. Most preferably the chemokine is human CCL21 or the murine analog thereof (murine CCL21).

Preferred hematopoietins include T cell growth factors such as IL-2, IL-15, and the like. Preferred interferons include those produced by T cells and NK cells such as IFN-γ, and the like. Other preferred cytokines include NK cell activating cytokines such as IL-12, and the like, and cytokines that induce cytokine production in cells such as epithelia, endothelia, and fibrolasts, including IL-17, and the like.

In another preferred embodiment, the DNA vaccine comprises a polynucleotide sequence that operably encodes a survivin protein and a ligand for a natural killer cell surface receptor. Preferably, the survivin protein is human survivin, murine survivin or an epitope of human survivin. Preferably the ligand for a natural killer cell surface receptor is a ligand for the NKG2D cell surface receptor. Preferably the ligand for the NKG2D cell surface receptor is a MHC class I chain-related (MIC) antigen such as MICA and MICB, a UL16 binding protein (ULBP) such as ULBP1, ULBP2, and ULBP3, and the like. Murine NKG2D ligands include, for example, Rae1 and minor histocompatibility antigen peptide H60. Most preferably, the ligand for the NKG2D cell surface receptor is MICA or MICB In yet another preferred embodiment the DNA vaccine comprises a polynucleotide sequence that operably encloses a livin protein and a ligand for a NK cell receptor. The livin protein can be wild-type human livin or an epitope of human livin or a livin variant.

Preferably, a DNA construct of the present invention, which operably encodes a cancer-associated IAP-family protein and an immunoactive gene product, is also operably linked to regulatory elements needed for gene expression, which are well known in the art.

Preferably the DNA construct is operably incorporated in an expression vector such as the BUDCE4.1 expression vector available from Invitrogen, Inc., Carlsbad, Calif. Other suitable expression vectors are commercially available, for example, from BD Biosciences Clonetech, Palo Alto, Calif. Once incorporated in the expression vector, the DNA construct can be introduced into a host vector such as a live, attenuated bacterial vector by transfecting the host cell with the expression vector to provide a vaccine of the present invention.

DNA constructs preferably include regulatory elements necessary for expression of nucleotides. Such elements include, for example, a promoter, an initiation codon, a stop codon, and a polyadenylation signal. In addition, enhancers are often required for expression of a sequence that encodes an immunogenic target protein. As is known in the art, these elements are preferably operably linked to the sequence that encodes the desired protein. Regulatory elements are preferably selected that are compatible with the species to which they are to be administered.

Initiation codons and stop codons are preferably included as part of a nucleotide sequence that encodes the survivin protein and the immunomodulating polypeptide in a genetic vaccine of the present invention. The initiation and termination codons must, of course, be in frame with the coding sequences for the survivin protein and the immunomodulating polypeptide.

Promoters and polyadenylation signals included in a vaccine of the present invention are preferably selected to be functional within the cells of the subject to be immunized.

Examples of promoters useful in the vaccines of the present invention, especially in the production of a genetic vaccine for humans, include but are not limited to promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, Cytomegalovirus (CMV) such as the CMV immediate early promoter, Epstein Barr Virus (EBV), Rous Sarcoma Virus (RSV) as well as promoters from human genes such as human actin, human myosin, human hemoglobin, human muscle creatine, and human metalothionein.

Examples of polyadenylation signals useful in the vaccines of the present invention, especially in the production of a genetic vaccine for humans, include but are not limited to SV40 polyadenylation signals and LTR polyadenylation signals.

In addition to the regulatory elements required for DNA expression, other elements can also be included in the DNA molecule. Such additional elements include enhancers. The enhancer can be, for example, human actin, human myosin, human hemoglobin, human muscle creatine and viral enhancers such as those from CMV, RSV and EBV.

Regulatory sequences and codons are generally species dependent. In order to maximize protein production, the regulatory sequences and codons are selected to be effective in the species to be immunized. One having ordinary skill in the art can readily produce DNA constructs that are functional in a given subject species.

The DNA constructs of the present vaccines can be "naked" DNA as defined in Restifo et al. *Gene Therapy* 2000; 7:89-92, the pertinent disclosure of which is incorporated by reference. Preferably, the DNA is operably incorporated in a vector. Useful delivery vectors include biodegradable microcapsules, immuno-stimulating complexes (ISCOMs) or liposomes, and genetically engineered attenuated live vectors such as viruses or bacteria.

Examples of suitable attenuated live bacterial vectors include *Salmonella typhimurium, Salmonella typhi, Shigella* species, *Bacillus* species, *Lactobacillus* species, Bacille Calmette-Guerin (BCG), *Escherichia coli, Vibrio cholerae, Campylobacter* species, *Listeria* species, or any other suitable bacterial vector, as is known in the art. Preferably the vector is an attenuated live *Salmonella typhimurium* vector. Preferred attenuated live *Salmonella typhimurium* include AroA⁻ strains such as SL7207, or doubly attenuated AroA⁻, dam⁻ strains, such as RE88. The doubly attenuated AroA⁻, dam⁻ *Salmonella typhimurium* is a particularly preferred vector.

Methods of transforming live bacterial vectors with an exogenous DNA construct are well described in the art. See, for example, Joseph Sambrook and David W. Russell, *Molecular Cloning, A Laboratory Manual*, 3rd Ed., Cold Spring Harbor Laboratory Press, Cold Spring Harbor, N.Y. (2001) (Sambrook and Russell).

Preferred viral vectors include Bacteriophages, Herpes virus, Adenovirus, Polio virus, Vaccinia virus, and Avipox. Methods of transforming viral vector with an exogenous DNA construct are also well described in the art. See Sambrook and Russell, above.

Useful liposome vectors are unilamellar or multilamellar vesicles, having a membrane portion formed of lipophilic material and an interior aqueous portion. The aqueous portion is used in the present invention to contain the polynucleotide material to be delivered to the target cell. It is generally preferred that the liposome forming materials have a cationic group, such as a quaternary ammonium group, and one or more lipophilic groups, such as saturated or unsaturated alkyl groups having about 6 to about 30 carbon atoms. One group of suitable materials is described in European Patent Publication No. 0187702, and further discussed in U.S. Pat. No. 6,228,844 to Wolff et al., the pertinent disclosures of which are incorporated by reference. Many other suitable liposome-forming cationic lipid compounds are described in the literature. See, e.g., L. Stamatatos, et al., *Biochemistry* 1988; 27:3917-3925; and H. Eibl, et al., *Biophysical Chemistry* 1979; 10:261-271. Alternatively, a microsphere such as a polylactide-coglycolide biodegradable microsphere can be utilized. A nucleic acid construct is encapsulated or otherwise complexed with the liposome or microsphere for delivery of the nucleic acid to a tissue, as is known in the art.

Other useful vectors include polymeric microspheres comprising biodegradable poly(ortho ester) materials, as described by Wang et al., *Nat. Mater.*, 2004; 3(3):190-6. Epub 2004 Feb. 15, the relevant disclosures of which are incorporated herein by reference.

A method aspect of the present invention involves administering DNA vaccine operably encoding a cancer-associated IAP-family protein and an immunoreactive gene product to the tissue of a mammal, such as a human. In some preferred embodiments, the DNA vaccines are administered orally, intramuscularly, intranasally, intraperitoneally, subcutaneously, intradermally, or topically. Preferably the DNA vaccine is administered orally.

In a preferred method, a DNA vaccine of the present invention can be utilized to provide long term inhibition of tumor growth in a patient treated with the vaccine. The DNA vaccine comprises a DNA polynucleotide construct operably encoding a cancer-associated IAP-family protein such as a survivin protein, an immunoactive gene product such as a cytokine or a ligand for a NK cell surface receptor, and a pharmaceutically acceptable carrier therefor. The vaccine is administered to a mammal in need of inhibition tumor growth in an amount that is sufficient to elicit an immune response against tumor cells.

Preferably, the mammal treated with a vaccine of the invention is a human. A patient suffering from cancer, such as lung or colon carcinoma, breast tumors, or prostate tumors, and the like cancers, can benefit from immunization by the vaccines of the present invention.

Vaccines of the present invention preferably are formulated with pharmaceutically acceptable carriers or excipients such as water, saline, dextrose, glycerol, and the like, as well as combinations thereof. The vaccines can also contain auxiliary substances such as wetting agents, emulsifying agents, buffers, preservatives, adjuvants, and the like.

The vaccines of the present invention are preferably administered orally to a mammal, such as a human, as a solution or suspension in a pharmaceutically acceptable carrier, at a DNA concentration in the range of about 1 to about 10 micrograms per milliliter. The appropriate dosage will depend upon the subject to be vaccinated, and in part upon the judgment of the medical practitioner administering or requesting administration of the vaccine.

The vaccines of the present invention can be packaged in suitably sterilized containers such as ampules, bottles, or vials, either in multi-dose or in unit dosage forms. The containers are preferably hermetically sealed after being filled with a vaccine preparation. Preferably, the vaccines are packaged in a container having a label affixed thereto, which label identifies the vaccine, and bears a notice in a form prescribed by a government agency such as the United States Food and Drug Administration reflecting approval of the vaccine under appropriate laws, dosage information, and the like. The label preferably contains information about the vaccine that is useful to an health care professional administering the vaccine to a patient. The package also preferably contains printed informational materials relating to the administration of the vaccine, instructions, indications, and any necessary required warnings.

The human survivin DNA sequence and its corresponding protein sequence have been reported by Strausberg in the EMBL database of the European Bioinformatics Institute, Wellcome Trust Genome Campus, Hinxton, Cambridge CB10 1SD, UK, DNA Accession No. BC034148, the disclosures of which are incorporated herein by reference. The DNA sequence and corresponding protein sequence of murine TIAP have been reported by Kobayashi et al. *Proc. Natl. Acad. Sci.* 1999; 96:1457-62; DNA Accession No. AB01389 in the EMBL database of the European Bioinformatics Institute, Wellcome Trust Genome Campus, Hinxton, Cambridge CB10 1SD, UK, the disclosures of which are incorporated herein by reference.

The nucleic acid sequence encoding human survivin is presented in FIG. 1 (SEQ ID NO: 1), and its corresponding amino acid residue sequence (SEQ ID NO: 2) is provided in FIG. 2. The nucleic acid sequence encoding murine survivin (i.e., TIAP) is presented in FIG. 3 (SEQ ID NO: 3), and its corresponding amino acid residue sequence (SEQ ID NO: 4) is provided in FIG. 4.

The protein homology between human survivin and its murine counterpart, TIAP, is illustrated in FIG. 5. There is about 83% amino acid residue sequence identity between human survivin (SEQ ID NO: 2) and murine TIAP (SEQ ID NO: 4) as shown in FIG. 5.

Mahotka et al. have identified two splice variants of human survivin, designated survivin-ΔEx3 and survivin-2B, which are also suitable for use in the present invention. Mahotka et al. *Cancer Res.*, 1999; 59:6097-6102, the relevant disclosures of which are incorporated herein by reference. The amino acid residue sequences of survivin-2B (SEQ ID NO: 23) and survivin-ΔEx3 (SEQ ID NO:24) are shown in FIG. 37. Hirohashi et al. have identified a potent T cell epitope from survivin-2B, having the amino acid residue sequence AYACNTSTL (SEQ ID NO: 25), designated survivin-2B80-88, which elicits a cytotoxic T lymphocyte response against survivin-2B. Hirohashi et al. *Clinical Cancer Res.*, 2002; 8:1731-39, the relevant disclosures of which is incorporated herein by reference. This epitope is a fragment of survivin which is capable of binding with a MHC class I molecule and is recognized by cytotoxic T cells, and is suitable for use as the IAP-family protein component of a vaccine of the present invention.

Another splice variant of human survivin is the survivin-3B variant described by Badran et al., *Biochem. Biophys. Res. Commun.*, 2004; 314(3):902-907. The polynucleotide sequence encoding survivin-3B and its corresponding amino acid residue sequence are reported in the EMBL database of the European Bioinformatics Institute, Wellcome Trust Genome Campus, Hinxton, Cambridge CB10 1SD, UK, DNA Accession No. AB154416, the disclosures of which are incorporated herein by reference.

Full length human livin (known as the alpha variant) is an IAP-family protein having a single BIR domain and consisting of 298 amino acid residues. The DNA sequence and corresponding protein sequence of human livin alpha variant have been reported by Clark et al. in the EMBL database of the European Bioinformatics Institute, Wellcome Trust Genome Campus, Hinxton, Cambridge CB10 1SD, UK, DNA Accession No. NM 139317, the disclosures of which are incorporated herein by reference. The DNA sequence and corresponding protein sequence of the beta variant of human livin have been reported by; Accession No. NM 022161 in the EMBL database of the European Bioinformatics Institute, Wellcome Trust Genome Campus, Hinxton, Cambridge CB10 1SD, UK, the disclosures of which are incorporated herein by reference.

The nucleic acid sequence encoding full length human livin (alpha variant) is presented in FIG. 39 (SEQ ID NO: 26), and its corresponding amino acid residue sequence (SEQ ID NO: 27) is provided in FIG. 40. The nucleic acid sequence encoding the beta variant of human livin is presented in FIG. 41 (SEQ ID NO: 28), and its corresponding amino acid residue sequence (SEQ ID NO: 29) is provided in FIG. 42. The beta variant of human livin lacks amino acid residues 216 through 233 of the full length human livin alpha splice variant (SEQ ID NO: 27). The beta variant is identical to the alpha variant of human livin in all other respects. The BIR domain of both the alpha and beta variants of human livin is in the region from amino acid residue R90 to amino acid residue L155 of SEQ ID NO: 27 and SEQ ID NO: 29).

In a preferred embodiment, the vaccines for the present invention comprise DNA constructs that encode one or more survivin proteins, such as human survivin, TIAP (murine survivin), and immunogenic homologs thereof. The immunogenic homologs preferably share at least about 80% amino acid residue sequence identity with human survivin, more preferably at least about 90% amino acid residue sequence identity, most preferably at least about 95% amino acid residue sequence identity with SEQ ID NO: 2. Alternatively, the vaccine can comprise a DNA construct that encodes one or more T-cell epitopes of human survivin protein.

In another preferred embodiment, the vaccines for the present invention comprise DNA constructs that encode one or more livin proteins, such as human livin alpha and beta splice variants (SEQ ID NO: 27 and 29, respectively), immunogenic homologs thereof. The immunogenic homologs preferably share at least about 80% amino acid residue sequence identity with the alpha or beta spice variant of human livin, more preferably at least about 90% amino acid residue sequence identity, most preferably at least about 95% amino acid residue sequence identity with SEQ ID NO: 27 or SEQ ID NO: 29. Alternatively, the vaccine can comprise a DNA construct that encodes one or more T-cell epitopes of a human livin protein.

Due to the inherent degeneracy of the genetic code, DNA sequences that encode substantially the same or a functionally equivalent amino acid residue sequence to native (i.e., naturally occurring) cancer-associated IAP-family proteins, such as human survivin, murine survivin, and human livin splice variants, can be used in the vaccines of the invention. Such DNA sequences include those which are capable of hybridizing to the native survivin or livin DNA sequences, as well as allelic variants, and the like. Preferably the DNA of the functionally equivalent homologs share at least about 70% nucleotide sequence identity with the DNA encoding the aforementioned native survivin or livin proteins, more preferably at least about 80% nucleotide sequence identity.

Immunoactive gene products encoded by the DNA constructs of the present vaccines are preferably cytokines or ligands of natural killer cell surface receptors. Particularly preferred cytokines are CC chemokines Particularly useful CC chemokines are ligands for the CCR7 chemokine receptor. Selective CCR7 ligands include CCL19 (also known as exodus-3, ELC, MIP-3β and CKβ11) and CCL21 (also known as exodus-2, SLC, 6Ckine, TCA4 and CKβ9). Particularly preferred chemokines are human CCL21 and its murine counterpart 6Ckine/SLC (muCCL21), and chemokines substantially corresponding thereto.

DNA and protein sequences for human SLC have been reported by Nishimura et al., in the EMBL database of the European Bioinformatics Institute, Wellcome Trust Genome Campus, Hinxton, Cambridge CB10 1SD, UK, DNA Accession No. AB002409, the disclosures of which are incorporated herein by reference. The murine CCL21a variant of 6Ckine/SLC DNA and protein sequences have been reported by Hromas et al. *J. Immunol.* 1997; 159(6):2554-2558, DNA Accession No. NM011335 in the EMBL database of the European Bioinformatics Institute, Wellcome Trust Genome Campus, Hinxton, Cambridge CB10 1SD, UK, the disclosures of which is incorporated herein by reference. The murine CCL21b variant of 6Ckine/SLC DNA and protein sequences have been reported by Hedrick et al., *J. Immunol.* 1997; 159(4):1589-1593, DNA Accession No. NM011124 in the EMBL database of the European Bioinformatics Institute, Wellcome Trust Genome Campus, Hinxton, Cambridge CB10 1SD, UK, the disclosures of which is incorporated herein by reference.

The nucleic acid sequence encoding human CCL21 (SLC) is presented in FIG. 6 (SEQ ID NO: 5), and its corresponding amino acid residue sequence (SEQ ID NO: 6) is provided in FIG. 7. The nucleic acid sequence encoding murine CCL21 (CCL21b variant) is presented in FIG. 8 (SEQ ID NO: 7), and its corresponding amino sequence (SEQ ID NO: 8) is provided in FIG. 9.

The protein homology between human CCL21 (SLC) and its murine counterpart (murine 6Ckine/SLC, CCL21b) is illustrated in FIG. 10. There is about 73% amino acid residue sequence identity between human CCL21 (SEQ ID NO: 6) and murine CCL21 (SEQ ID NO: 8) as shown in FIG. 10.

The nucleic acid sequence encoding the CCL21a variant of murine SLC is presented in FIG. 25 (SEQ ID NO: 11), and its corresponding amino sequence (SEQ ID NO: 12) is provided in FIG. 26.

Preferred ligands for natural killer cell surface receptors are ligands for the murine NKG2D surface receptor. Preferred ligands for the NKG2D surface receptor are MICA, MICB, ULBP1, ULBP2, and ULBP3, and the like. Most preferably MICA and MICB. Other known ligands for NKG2D surface receptors include murine Rea-1β and murine minor histocompatibility antigen peptide H60.

The murine H60 minor histocompatibility antigen peptide DNA and protein sequences have been reported by Malarkannan et al., *J. Immunol.* 1998; 161(7):3501-3509, DNA Accession No. AF084643 in the EMBL database of the European Bioinformatics Institute, Wellcome Trust Genome Campus, Hinxton, Cambridge CB10 1SD, UK, the disclosures of which are incorporated herein by reference. A partial nucleic acid sequence encoding murine H60 minor histocompatibility antigen peptide is presented in FIG. 11 (SEQ ID NO: 9), and its corresponding partial amino acid residue sequence (SEQ ID NO: 10) is provided in FIG. 12.

DNA and protein sequences for human MICA have been reported by Zwirner et al., DNA Accession No. AY204547 in the EMBL database of the European Bioinformatics Institute, Wellcome Trust Genome Campus, Hinxton, Cambridge CB10 1SD, UK, the disclosures of which are incorporated herein by reference. The nucleic acid sequence encoding human MICA is presented in FIG. 27 (SEQ ID NO: 13), and its corresponding amino acid residue sequence (SEQ ID NO: 14) is provided in FIG. 28.

DNA and protein sequences for human MICB have been reported by Bahram et al. *Immunogenetics* 1996; 45(2):161-162, DNA Accession No. U65416 in the EMBL database of the European Bioinformatics Institute, Wellcome Trust Genome Campus, Hinxton, Cambridge CB10 1SD, UK, the disclosures of which are incorporated herein by reference. The nucleic acid sequence encoding human MICB is presented in FIG. 29 (SEQ ID NO: 15), and its corresponding amino acid residue sequence (SEQ ID NO: 16) is provided in FIG. 30. Allelic variants of MICB are described in GENBANK Accession No. NP 005922, incorporated herein by reference. FIG. 38 is a reproduction of the GENBANK entry for Accession No. NP 005922.

DNA and protein sequences for human ULBPI have been reported by Cosman et al., *Immunity* 2001; 14(2):123-133, DNA Accession No. AF304377 in the EMBL database of the European Bioinformatics Institute, Wellcome Trust Genome Campus, Hinxton, Cambridge CB10 1SD, UK, the disclosures of which are incorporated herein by reference. The nucleic acid sequence encoding human ULBP1 is presented in FIG. 31 (SEQ ID NO: 17), and its corresponding amino acid residue sequence (SEQ ID NO: 18) is provided in FIG. 32.

DNA and protein sequences for human ULBP2 have been reported by Cosman et al., *Immunity* 2001; 14(2):123-133, DNA Accession No. AF304378 in the EMBL database of the European Bioinformatics Institute, Wellcome Trust Genome Campus, Hinxton, Cambridge CB10 1SD, UK, the disclosures of which are incorporated herein by reference. The nucleic acid sequence encoding human ULBP2 is presented in FIG. 33 (SEQ ID NO: 19), and its corresponding amino acid residue sequence (SEQ ID NO: 20) is provided in FIG. 34.

DNA and protein sequences for ULBP3 have been reported by Cosman et al., *Immunity* 2001; 14(2):123-133, DNA Accession No. AF304379 in the EMBL database of the European Bioinformatics Institute, Wellcome Trust Genome Campus, Hinxton, Cambridge CB10 1SD, UK, the disclosures of which are incorporated herein by reference. The nucleic acid sequence encoding human ULBP3 is presented in FIG. 35 (SEQ ID NO: 21), and its corresponding amino acid residue sequence (SEQ ID NO: 22) is provided in FIG. 36.

Particularly preferred natural killer cell surface receptor ligands include ligands for the NKG2D receptor such as MICA, MICB, ULBP1, ULBP2, ULBP3, and functional equivalents thereof. The functional equivalents preferably share at least about 80% amino acid residue sequence identity with the aforementioned immunomodulating polypeptides, more preferably at least about 90% amino acid residue sequence identity, most preferably at least about 95% amino acid residue sequence identity.

Due to the inherent degeneracy of the genetic code, DNA sequences that encode substantially the same or a functionally equivalent amino acid residue sequence to the useful native immunoactive gene products such as human CCL21, murine CCL21, MICA, MICB, ULBP1, ULBP2, ULBP3, and like materials substantially corresponding thereto can be used in the vaccines of the invention. Such DNA sequences include those which are capable of hybridizing to the immunomodulating polypeptide DNA sequences, as well as allelic variants, and the like. Preferably the DNA of functionally equivalent homologs share at least about 70% nucleotide sequence identity with the DNA encoding the aforementioned native immunomodulating polypeptides.

Altered DNA sequences that can be used in accordance with the invention include deletions, additions or substitutions of different nucleotide residues in the native polynucleotide sequence encoding a wild-type cancer-associated IAP-family protein resulting in a sequence that encodes the wild-type protein or an immunogenic homolog thereof. The altered DNA sequences that can be used in accordance with the invention can also include deletions, additions or substitutions of different nucleotide residues in the native polynucleotide encoding a wild type immunogenic gene product resulting in a sequence that encodes the wild-type immunoactive gene product or a functional equivalent thereof. Functionally equivalent immunoactive gene product may contain deletions, additions or substitutions of amino acid residues within a wild-type cytokine, or NK cell surface receptor ligand, which result in a silent change, thus producing a functionally equivalent molecule. Such amino acid substitutions (e.g., conservative substitutions) may be made on the basis of similarity in polarity, charge, solubility, hydrophobicity, hydrophilicity, and/or the amphipathic nature of the residues involved. For example, negatively charged amino acids include aspartic acid and glutamic acid;

positively charged amino acids include lysine and arginine; amino acids with uncharged polar head groups having similar hydrophilicity values include the following: leucine, isoleucine, valine; glycine, alanine; asparagine, glutamine; serine, threonine; phenylalanine, tyrosine.

As used herein, a functionally equivalent immunoactive gene product, such as a cytokine or NK cell surface receptor ligand refers to a polypeptide having substantially the same immunomodulating activity as its counterpart naturally occurring immunoactive gene product.

The DNA sequences operably encoding the IAP-family protein and the immunoactive gene products useful in the vaccines of the invention may be engineered to alter the coding sequences for a variety of purposes including, but not limited to, alterations that modify processing and expression of the gene product. For example, mutations may be introduced using techniques that are well known in the art, e.g. site-directed mutagenesis, to insert new restriction sites, to alter glycosylation patterns, phosphorylation, and the like.

Another aspect of the present invention is a method of vaccinating a mammal against cancer. The method comprises administering to the mammal a vaccine of the present invention, as described herein, in an amount sufficient to elicit an immune response against cancer cells. Preferably the mammal is a human.

In another aspect, the present invention also encompasses transformed host cells, which have been transfected with a vector comprising a DNA construct operably encoding an Inhibitor of Apoptosis-family protein and an immunoactive gene product, as described herein. The host cell can be a prokaryotic cell or a eukaryotic cell.

The present invention also provides isolated plasmid vectors comprising a DNA construct operably encoding an Inhibitor of Apoptosis-family protein and an immunoactive gene product. The vectors are useful for transfecting host cells, such as attenuated bacterial cells, for preparing the vaccines of the invention.

The following examples are provided to further illustrate the features and embodiments of the present invention, and are not meant to be limiting.

Materials, Methods and Examples.

Materials.

C57/BL/6J and Balb/C mice were obtained from the Scripps Research Institute breeding facility. The DNA encoding TIAP (the murine form of survivin) was cloned by PCR from MC3P cDNA. The DNA encoding murine 6Ckine (murine CCL21) was cloned from spleen cells. DNA encoding H60 minor histocompatibility antigen peptide (the murine form of MICA and MICB) was kindly provided by Dr. David H. Ranlet of the University of California (Berkley). The DNA for the vaccine encoding murine CCL21 (muCCL21, also known as 6Ckine/SLC) and murine survivin (muSurvivin, also known as TIAP) was cloned into pBudCE4.1 eucaryotic expression vectors from Invitrogen, Inc., using the restriction sites HindIII and BamHI for MuCCL21, and using XhoI for both ends of muSurvivin. The DNA for the vaccine encoding H60 and TIAP was cloned into pBudCE4.1 eucaryotic expression vectors from Invitrogen, Inc., using the restriction sites HindIII and XbaI for H60, and for muSurvivin, using the restriction sites KpnI and XhoI. An AroA$^-$ attenuated strain of *Salmonella typhimurium* (SL2707) and a doubly attenuated AroA$^-$, dam$^-$ strain of *Salmonella typhimurium* (RE88) were obtained from Remedyne, Santa Barbara, Calif. Antibodies were obtained from BD Biosciences, Bedford, Mass. Fluorescein isothiocyanate (FITC) and R-Phycoerythrin (PE) were obtained from Molecular Probes, Eugene, Oreg. FITC-labeled and PE-labeled antibodies were prepared according to the manufacturer's recommended protocols.

Part A. Vaccines from Tranformed AroA$^-$ Attenuated *Salmonella typhimurium*

EXAMPLE 1

Preparation of a DNA Vaccine Encoding muSurvivin and muCCL21

The pBudCE4.1 vector containing muSurvivin and muCCL21 DNA (about 1-10 µg of pDNA) was electroporated into freshly prepared attenuated *Salmonella typhimurium* (SL2707), utilizing a Bio-Rad Pulser at 2.5 kV, 25 µF, and 200 Ohm according to the manufacturer's recommended procedures. *Salmonella* containing the vector were selected on zeocin-containing plates. Colonies were picked the next day and cultured overnight in LB broth (EM Science, Gibbstown, N.J.) with zeocin added. The bacteria were isolated and washed in phosphate buffered saline (PBS). The washed bacteria were then suspended in PBS medium at a concentration of about $1 \times 10^9$ recombinant *Salmonella* per milliliter of PBS, to form a vaccine solution for later use.

Control vaccines consisting of *Salmonella* transformed with the vector alone, a vector incorporating only muSurvivin DNA, and a vector incorporating only muCCL21 DNA were also prepared according to the same procedure. FIG. 13 provides a schematic representation of the expression constructs.

The vaccines were stored in sealed ampules until used. The plasmid DNA was stored at about −80° C. before transforming the *Salmonella*.

EXAMPLE 2

Vaccination of Mice with DNA Vaccines of Example 1

Balb/C mice (about 8 mice per treatment group) were vaccinated with the DNA vaccines of Example 1 (about $1 \times 10^8$ recombinant *Salmonella* in about 100 µl of PBS) by oral gavage, 3 times at 2 week intervals.

EXAMPLE 3

Evaluation of Tumor Resistance of Vaccinated Mice

About 1 week after the last vaccination, Balb/C mice from Example 2 (about 8 mice per treatment group) were challenged with about $1 \times 10^5$ D121 Lewis lung carcinoma cells (subcutaneously). The subcutaneous Lewis lung tumors were surgically removed after about 2 weeks of growth to allow spontaneous dissemination to the lung. Subcutaneous tumor growth was measured in two dimensions every other day, and tumor volume was calculated according to the formula:

$$\text{volume} = (\text{width}^2)(\text{length} \div 2)$$

for each tumor. The amount of spontaneous metastasis of D121 to the lungs was evaluated about 24 to about 28 days after removal of the subcutaneous primary tumor. The mice were sacrificed and necropsied, and the tumor burdens of the lungs were evaluated according to the percentage of the lung surface that was covered by tumor and scored as "0" for no tumor, "1" for less than about 20% tumor coverage, "2" for about 20 to about 30% tumor coverage, and "3" for greater than about 50% tumor coverage.

Figure 14:
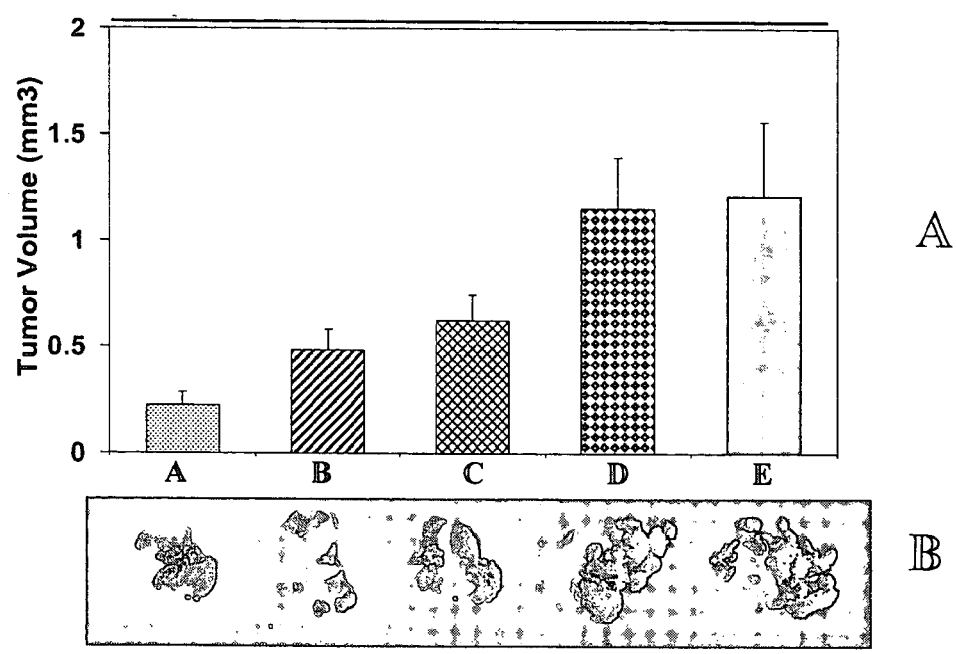
FIG. 14A graphically depicts average tumor volume for pulmonary metastases of Lewis lung carcinomas in mice treated with a control buffer (E), a control vaccine comprising an empty vector (D), a DNA vaccine comprising a chemokine (C), a vaccine comprising a survivin protein (B) and a vaccine of the invention (A)
FIG. 14B includes pictures of typical lung tumor metastases excised from the mice vaccinated as described in FIG. 14A.

The tumor burden scores for the mice vaccinated with the vaccines of Example 1 are provided in Table 1. FIG. 14 shows pictures of lungs from mice vaccinated with the vaccines of Example 1. Tumor volumes are reported in Table 1 and in FIG. 14. In FIG. 14, bar A represents the average lung tumor volume (in cubic millimeters) for mice vaccinated with the muSurvivin/muCCL21 vaccine of the invention; bar B represents the average tumor volume for mice vaccinated with the vaccine that only incorporated muSurvivin DNA; bar C represents the average tumor volume for mice vaccinated with the vaccine that only incorporated muCCL21 DNA; bar D represents the average tumor volume for mice vaccinated with the vaccine that only incorporated the empty vector; and bar E represents the average tumor volume for mice vaccinated with PBS buffer. FIG. 14 also includes pictures of representative excised lungs from each treatment group, shown below each of their respective bars from FIG. 14.

TABLE 1

Tumor Metastasis in Balb/C Mice Challenged with D121 Lewis Lung Carcinoma Cells.

| Mouse Vaccination Group | Metastatic Scores |
|---|---|
| A. muSurvivin/muCCL21 Vaccine | 0, 0, 0, 1, 1, 1, 2, 2 |
| average lung tumor volume: | (0.242 ± 0.06 mm$^3$) |
| B. Control - muSurvivin Vaccine | 1, 1, 2, 3, 3, 3, 3, 3 |
| average lung tumor volume: | (0.483 ± 0.10 mm$^3$) |
| C. Control - muCCL21 vaccine | 2, 2, 2, 3, 3, 3, 3, 3 |
| average lung tumor volume: | (0.626 ± 0.06 mm$^3$) |
| D. Control - empty vector vaccine | 2, 3, 3, 3, 3, 3, 3, 3 |
| average lung tumor volume: | (1.152 ± 0.24 mm$^3$) |
| E. Control - vaccination with PBS | 2, 3, 3, 3, 3, 3, 3, 3 |
| average lung tumor volume: | (1.212 ± 0.35 mm$^3$) |

The results provided in Table 1 and FIG. 14 (diagrams A and B) demonstrate that the DNA vaccine comprising a DNA construct encoding an IAP-family protein (i.e., muSurvivin) and an immunoactive gene product (i.e., muCCL21) can effectively immunize mice against lung tumor metastases and inhibited growth of lung tumors.

EXAMPLE 4

T Cell Mediated Cytotoxicity Against D121 Lung Cancer Cells Induced by DNA Vaccine of the Invention of the Invention C5/7BL/6J mice (about 8 mice per treatment group) were vaccinated with the DNA vaccines of Example 1 as described in Example 2. Splenocytes were isolated about 4 days after vaccination and analyzed for their lytic activity in a 4-hour $^{51}$Cr-release assay, as described in *Current Protocols in Immunology* at 3.11.4, Coligan, et al. Eds., John Wiley & Sons, Inc. (1994). D121 cells were used as target cells for the splenocytes.

Figure 15:
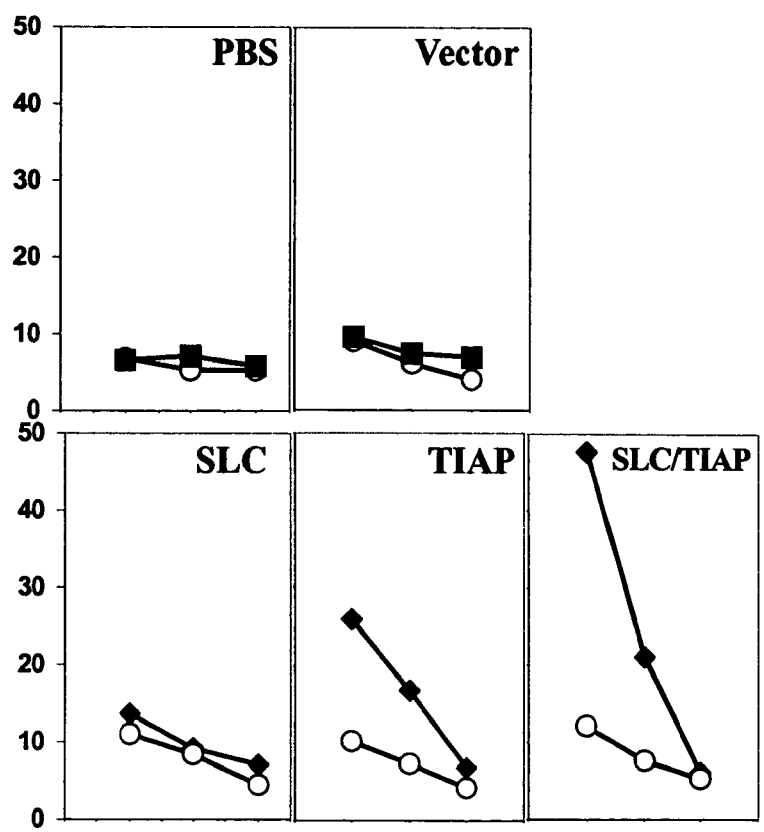
FIG. 15 depicts the T cell mediated cytotoxicity induced by the DNA vaccines described in FIG. 14A against D121 lung cancer cells; the percentage of lysis (Y-axis) is plotted for three different effector cell to target cell (E/T) ratios for each vaccination (i.e., 100:1, first data point; 50:1, second data point; and 25:1, third data point)

FIG. 15 graphically illustrates T cell mediated cytotoxicity against D121 lung cancer cells induced by the DNA vaccines of the invention. The data points represented by the open circles represent data from inhibition assays wherein the cells were treated with 50 μg/ml of antibodies to H-2K$^b$/H-2D$^b$ MHC class I antigens (clone SF1-1.1; 34-2-12 IgG2a, κ) and the solid black squares represent data in the absence of inhibiting antibodies. The percentage of lysis of tumor cells (Y-axis) is plotted for three different effector cell to target cell (E/T) ratios for each vaccination group (i.e., E/T of 100:1 for the first data point; 50:1 for the second data point; and 25:1 for the third data point). The results demonstrate that the muSurvivin/muCCL21 vaccine of the invention (labeled SLC/TIAP) induced almost a 5-fold increase in lysis at the 100:1 E/T ratio compared to control vaccines comprising PBS, empty vector, and muCCL21 DNA, and an increase of about 2-fold over the control vaccine comprising muSurvivin DNA alone.

EXAMPLE 5

Upregulation of CD25, CD69 and CD28 Activation Markers in Splenocytes (CD8+ T Cells) from Vaccinated Mice C5/7BL/6J mice (about 4 mice per treatment group) were vaccinated with the DNA vaccines of Example 1 as described in Example 2. Splenocytes were isolated from the immunized mice and the control mouse group about 1 week after the last vaccination. The cells were then stained with FITC-conjugated CD8+ antibody and PE-conjugated antibodies of CD25, CD69, and CD28. The cell suspensions were evaluated using a two color flow cytometry Becton Dickenson FAC scan to determine the percentage of CD8+ T cells positive for CD25, CD 28 and CD69 for each splenocyte. The results are presented in FIG. 16. The numerical value in the upper right hand quadrant in each FACS plot indicates the percentage of cells that presented both CD8+ antigen as well as CD25, CD28, or CD69, as the case may be. The numerical results are shown in Table 2. These results demonstrate increased T cell marker expression with the vaccine of the present invention, indicating enhanced T cell activation.

TABLE 2

Upregulation of CD25, CD69 and CD28 Activation Markers in Splenocytes From Vaccinated Mice

| Treatment | % CD25 and DC8+ | % CD69 and DC8+ | % CD28 and DC8+ |
|---|---|---|---|
| Control vaccine/PBS | 7.3 | 11.2 | 1.62 |
| Control vaccine/empty vector | 8.2 | 11.4 | 1.57 |
| Control vaccine/muCCL21 | 10.2 | 12.9 | 2.3 |
| Control vaccine/muSurvivin | 9.5 | 13.3 | 2.21 |
| muSurvivin/muCCL21 vaccine | 12.4 | 17.7 | 3.8 |

Figure 16:
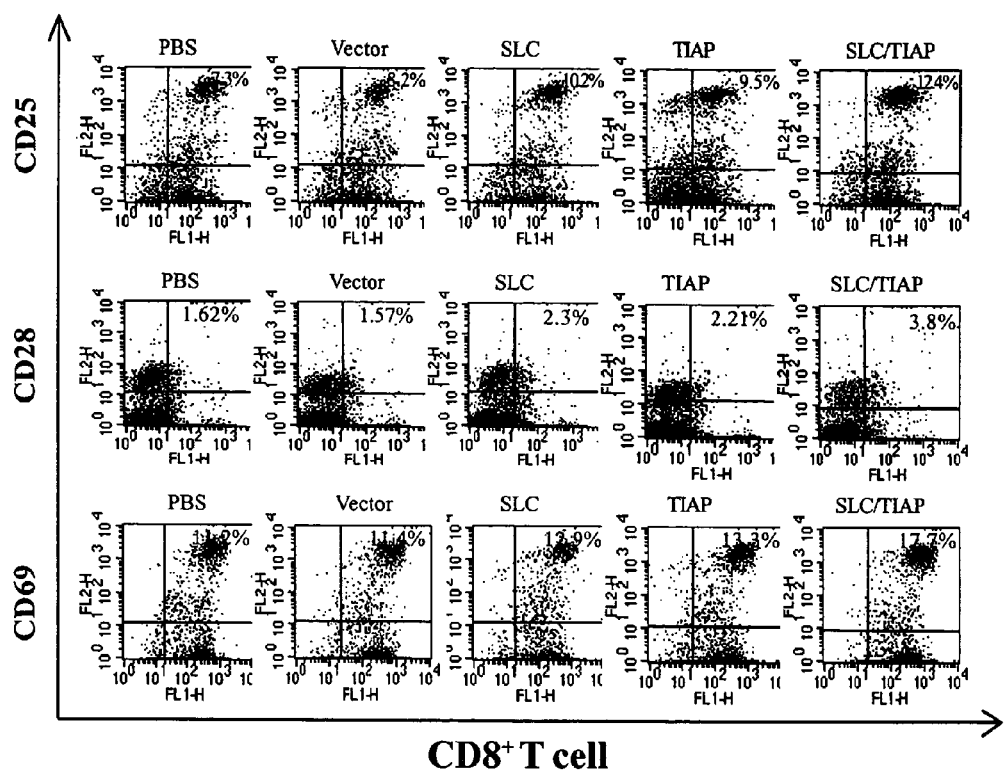
FIG. 16 graphically illustrates upregulated expression of T cell activation molecules in mice vaccinated with a vaccine of the invention as determined by flow cytometry analysis.

The data in Table 2 and FIG. 16 demonstrate that the inventive vaccine of Example 1, comprising a DNA construct encoding for muSurvivin and muCCL21 leads to upregulated expression of T cell activation molecules.

EXAMPLE 6

Figure 17:
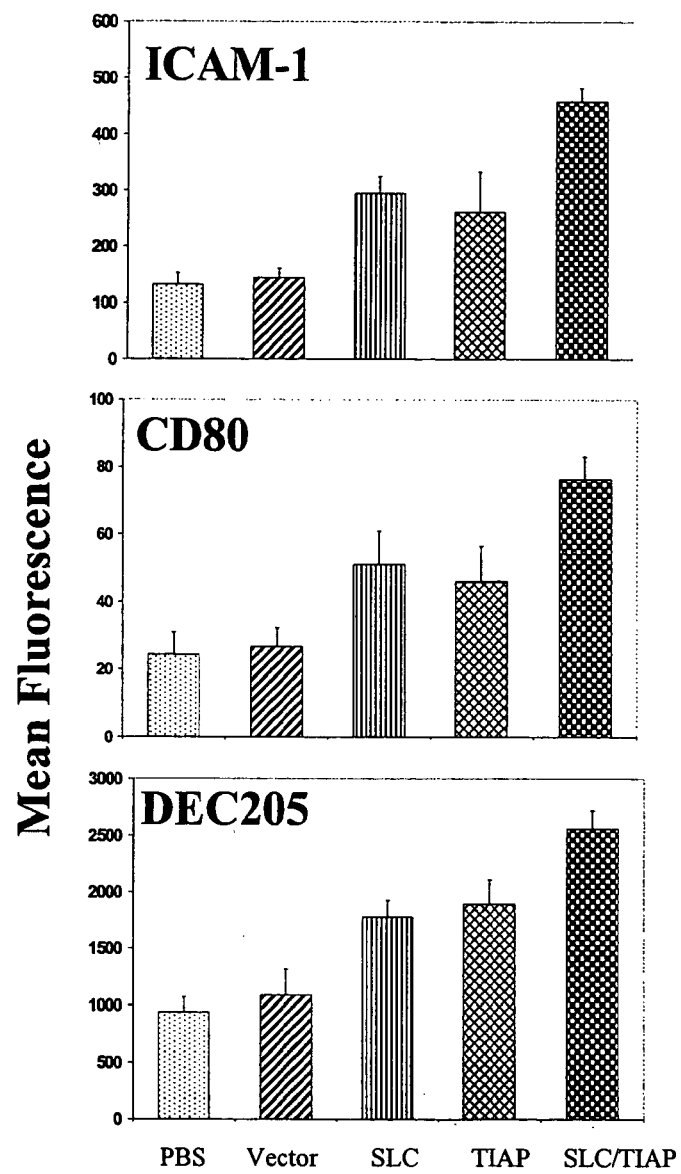
FIG. 17 graphically illustrates enhanced expression of co-stimulatory molecules by dendritic cells following vaccinations of mice with a vaccine of the invention and various control vaccines.

Enhanced Expression of Co-Stimulatory Molecules on Dendritic Cells in Vaccinated Mice C5/7BL/6J mice (about 4 mice per treatment group) were vaccinated with the DNA vaccines of Example 1 as described in Example 2. Splenocytes were isolated from the immunized mice and the control mouse group about 1 week after the last vaccination. The cells were then stained with FITC-conjugated CD11c antibody in combination with PE-conjugated antibodies of co-stimulatory molecules B7 (CD80), ICAM-1, and DEC205. The cell suspensions were evaluated using a two color flow cytometry Becton Dickenson FAC scan. FIG. 17 graphically illustrates the mean fluorescence values for the cells showing increased expression of ICAM-1 (top), CD80 (middle) and DEC205 (bottom) for splenocytes isolated from mice vaccinated with a the muSurvivin/muCCL21 vaccine of the invention, relative to the control vaccines.

EXAMPLE 7

Induction of Intracellular Cytokine Release

Figure 18:
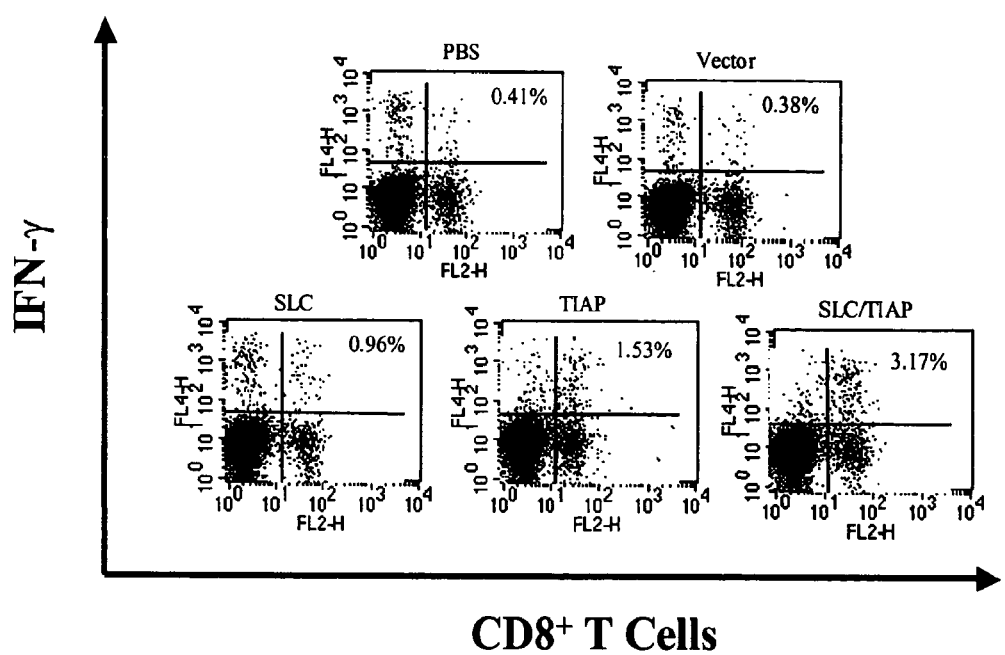
FIG. 18 illustrates induction of intracellular cytokine release following vaccinations of mice with a vaccine of the invention and various control vaccines, as determined by flow cytometry analysis.

Mice immunized as in Example 2 (8 mice per group) were challenged with D121 Lung Cancer Cells as in Example 3. Splenocytes were harvested from each mouse about one week after tumor cell challenge. The splenocytes were stained with FITC-anti-CD3 antibody and then fixed, permeabilized, and subsequently stained with PE conjugated anti IFN-γ antibody. The two-color stained cells were analyzed by FACS flow cytometry. The results are illustrated in FIG. 18. The cells were fixed using an intracellular staining starter kit from BD Pharmingen, La Jolla, Calif.

The results plotted in FIG. 18 demonstrate that the percentage of cells releasing the cytokine IFN-γ increased to about 3.17% for splenocytes isolated from mice vaccinated with a vaccine of the invention, compared to only 0.41% for mice receiving the PBS control vaccine, about 0.38% for mice receiving the empty vector control vaccine, about 0.96% for mice receiving the SLC control vaccine and about 1.53% for mice receiving the muSurvivin control vaccine.

EXAMPLE 8

Enhanced Apoptosis of Lung Cancers Cell in Vaccinated Mice

Mice immunized as in Example 2 (8 mice per group) were challenged with D121 Lung Cancer Cells as in Example 3. Splenocytes were harvested from each mouse about one week after tumor cell challenge. The splenocytes were incubated with D121 tumor cells at a temperature of about 37° C., for about 3 hours. Tumor cells were then isolated and analyzed by FACS Annexin V-FITC was used to quantitate the percentage of cells within the population that are actively undergoing apoptosis. Propidium iodide (PI) was used to distinguish viable from non-viable cells using an Apoptosis Detection Kit available from BD Pharmingen, La Jolla, Calif.

Figure 19:
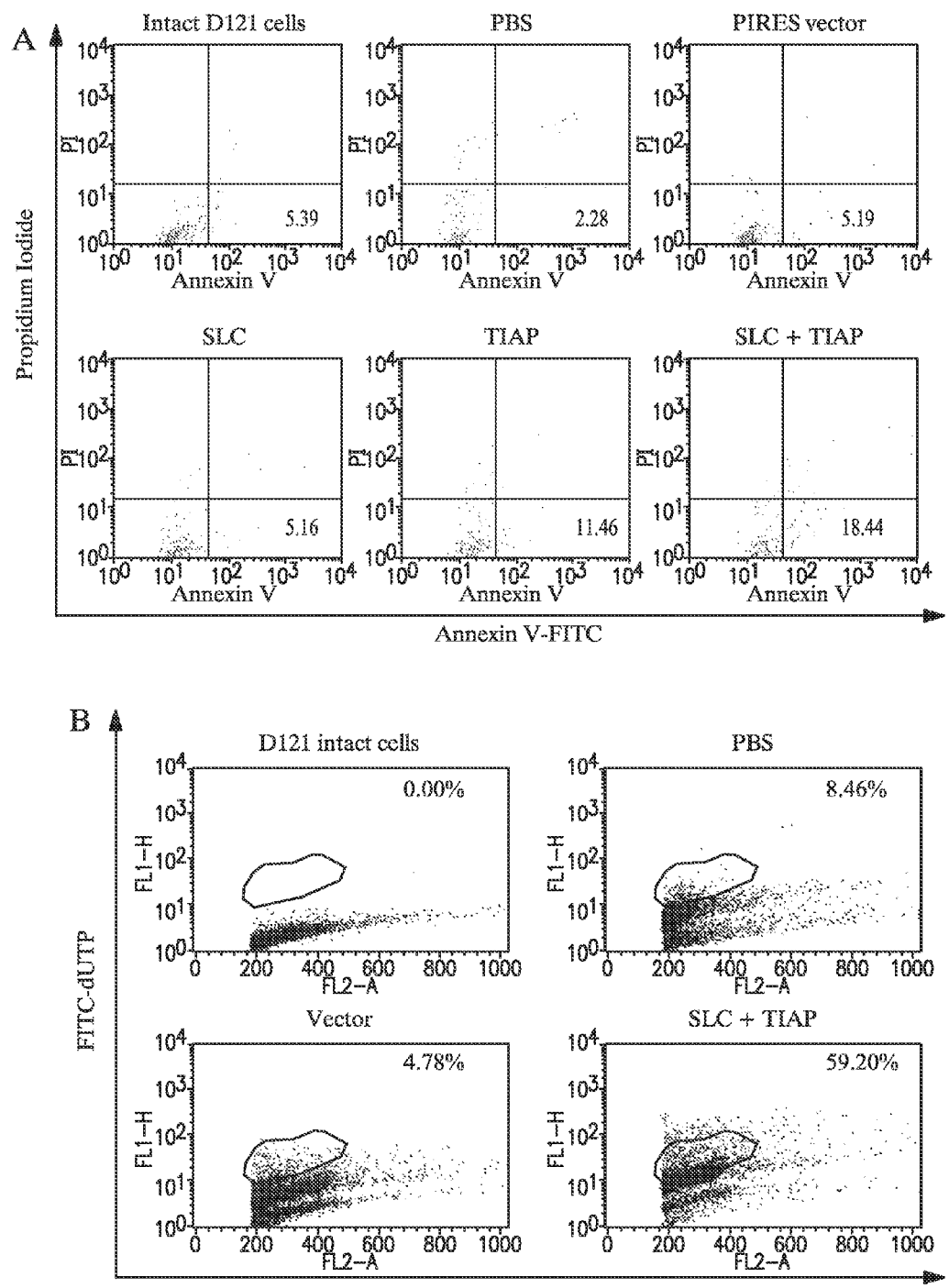
FIG. 19 illustrates FACS plots demonstrating an increase in apoptosis in D121 lung tumor cells following vaccination of mice with the vaccine of the invention and various control vaccines (A) 3 hours after vaccination; and (B) 24 hours after vaccination.

FIG. 19 graphically illustrates the FACS analysis results evaluated after about 3 hours (top set of plots) and after about 24 hours (bottom set of plots). The number in the lower right quadrant of each plot represent the percentage of cells undergoing apoptosis for each treatment group. After 3 hours, about 5.39% of the intact D121 cells (i.e., no exposure to splenocytes) had undergone apoptosis. About 2.28% of D121 cells incubated with splenocytes from mice vaccinated with a control vaccine containing only PBS buffer had undergone apoptotsis. Only about 5.19% of D121 cells incubated with splenocytes from mice vaccinated with a control vaccine comprising the empty vector DNA had undergone apoptosis. In similar fashion, about 5.15% of D121 cells underwent apoptosis when incubated with splenocytes from mice vaccinated with a control vaccine comprising the muCCL21 DNA alone; whereas about 11.46% of D121 cells underwent apoptosis when incubated with splenocytes from mice vaccinated with a control vaccine comprising the muSurvivin DNA alone. Surprisingly, after 3 hours, about 18.44% of D121 cells had undergone apoptosis when incubated with splenocytes from mice vaccinated with a vaccine of the invention comprising both muCCL21 and muSurvivin DNA.

Similarly after 24 hours, in a gated FACS analysis (gated for apoptosed cells), none of the intact D121 cells (i.e., no exposure to splenocytes) had undergone apoptosis. About 8.46% of D121 cells incubated with splenocytes from mice vaccinated with a control vaccine containing only PBS buffer had undergone apoptotsis. Only about 4.78% of D121 cells incubated with splenocytes from mice vaccinated with a control vaccine comprising the empty vector DNA had undergone apoptosis. Surprisingly, after 24 hours, about 59.2% of D121 cells had undergone apoptosis when incubated with splenocytes from mice vaccinated with a vaccine of the invention comprising both muCCL21 and muSurvivin DNA.

EXAMPLE 9

Figure 20:
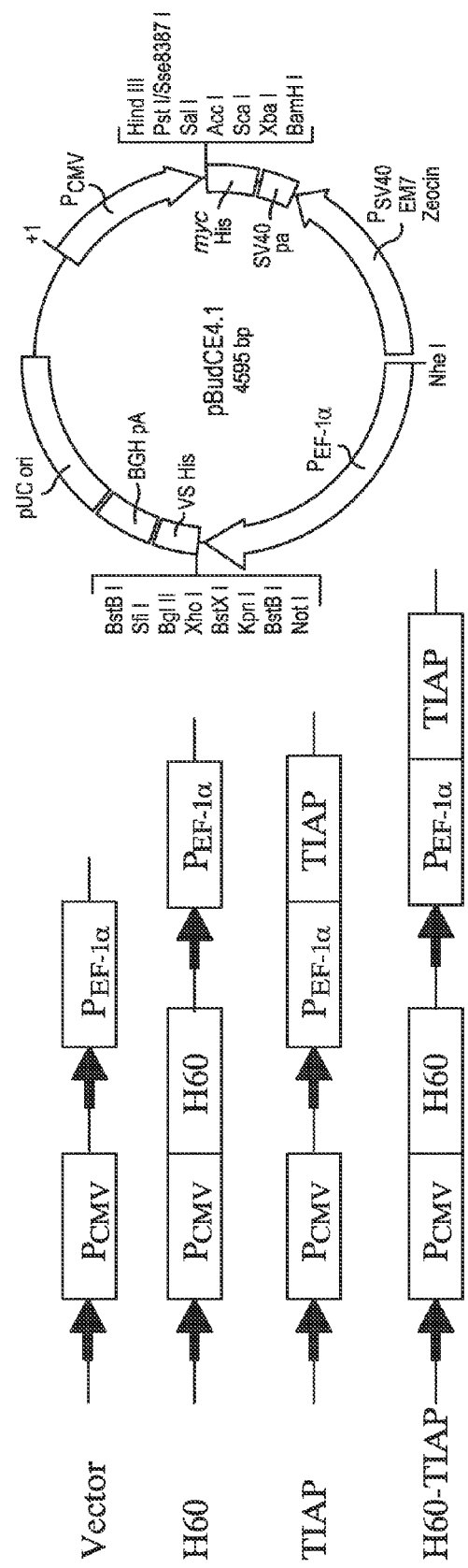
FIG. 20 depicts a schematic representation of expression constructs incorporating TIAP and minor histocompatibility antigen peptide H60.

Preparation of a DNA Vaccine Encoding TIAP and Murine H60 Minor Histocompatibility Antigen Peptide The pBudCE4.1 vector containing TIAP and murine H60 minor histocompatibility antigen DNA (about 1 μg of pDNA) was electroporated into freshly prepared attenuated *Salmonella typhimurium* (SL2707), utilizing a Bio-Rad Pulser at 2.0 kV, 25 μF, and 100 Ohm according to the manufacturer's recommended procedures. FIG. 20 provides a schematic diagram of the expression vectors for H60 and muSurvivin incorporated in the vector.

*Salmonella* containing the vector were selected on zeocin-containing plates. Colonies were picked the next day and cultured overnight in LB broth (EM Science, Gibbstown, N.J.) with zeocin added. The bacteria were isolated and washed in phosphate buffered saline (PBS). The washed bacteria were then suspended in PBS medium at a concentration of about $5 \times 10^9$ recombinant *Salmonella* per milliliter of PBS, to form a vaccine solution for later use.

Control vaccines consisting of *Salmonella* transformed with the vector alone, a vector incorporating only muSurvivin DNA, and a vector incorporating only H60 minor histocompatibility antigen (H60) DNA were also prepared according to the same procedure.

The vaccines were stored in sealed ampules until used. The plasmid DNA was stored at about −20° C. before transforming the *Salmonella*.

EXAMPLE 10

Vaccination of Mice with DNA Vaccines of Example 9

Balb/C mice (about 8 mice per treatment group) were vaccinated with the DNA vaccines of Example 9 (about $5 \times 10^8$ recombinant *Salmonella* in about 100 μl of PBS) by oral gavage, three times at two week intervals.

EXAMPLE 11

Cytotoxicity Assays of Splenocytes Isolated from Mice Vaccinated DNA Vaccines of Example 10

Figure 21:
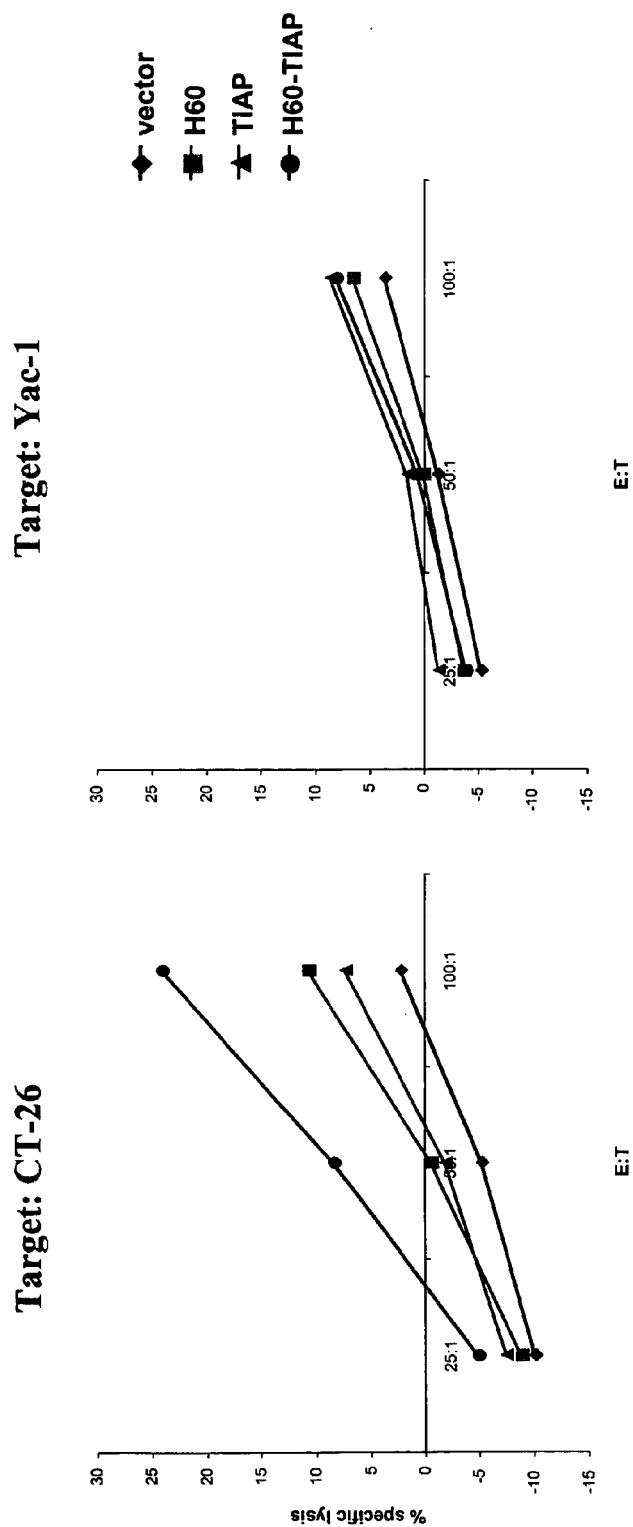
FIG. 21 graphically illustrates data from cytotoxicity assays of splenocytes isolated from mice vaccinated with a vaccine of the invention.

Splenocytes were isolated from the mice vaccinated in Example 10 and were stimulated with irradiated CT-26 cells. After 5 days, the splenocytes were harvested and cytotoxic assays were preformed against CT-26 cells and Yac-1 cells (NK-sensitive T cells) at targets. The degree of cell specific lysis was determined at E/T ratios of 25:1, 50:1 and 100:1 by a 4-hour $^{51}$Cr-release assay, as described in *Current Protocols in Immunology* at 3.11.4, Coligan, et al. Eds., John Wiley & Sons, Inc. (1994). The results are graphically illustrated in FIG. 21.

The results indicate that splenocytes from mice vaccinated with a vaccine of the present invention comprising muSurvivin and H60 DNA exhibited a two-fold or greater increases in lysis of CT-26 colorectal cancer cells compared to splenocytes isolated from mice vaccinated with the empty vector, H60 and muSurvivin control vaccines at the 100:1 E/T ratio. Very little lysis of Yac-1 was observed for all vaccines at all E/T ratios, indicating that the killing observed was likely mediated by T cells.

EXAMPLE 12

Evaluation of Tumor Resistance of Vaccinated Mice

About 2 weeks after the third vaccination, Balb/C mice from Example 10 (about 8 mice per treatment group) were challenged with about $1 \times 10^5$ murine CT-26 colorectal cancer cells (intravenously; i.v.).

Figure 22:
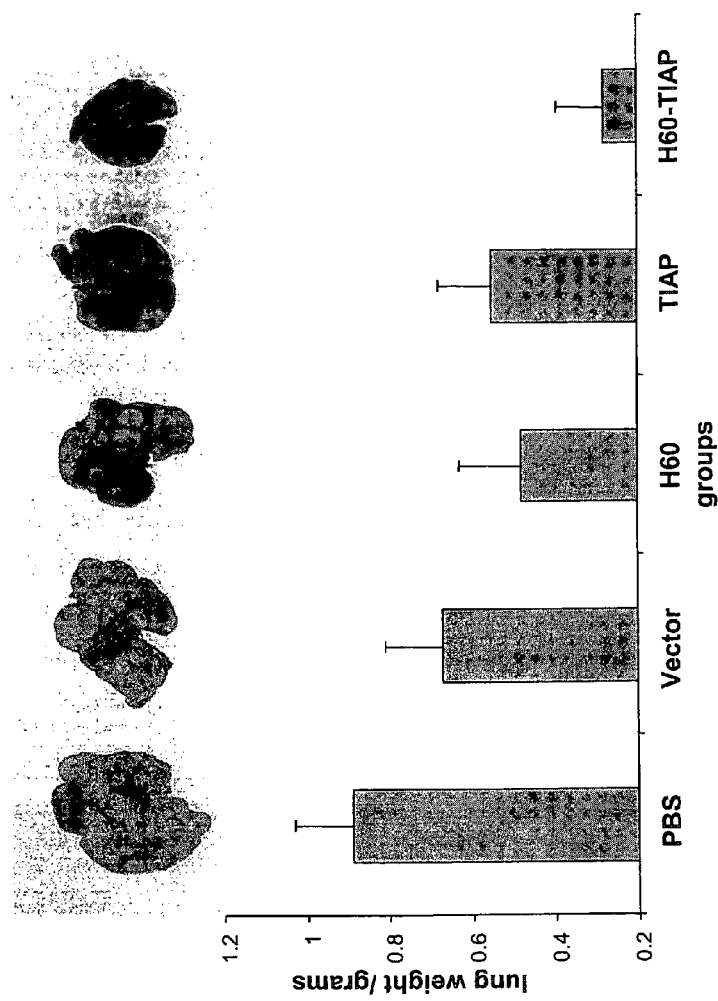
FIG. 22 depicts lungs excised from mice vaccinated as described in Example 10 (top) and a bar graph (bottom) of average lung weight of mice from the treatment groups.

The amount of spontaneous metastasis of CT-26 cells to the lungs was evaluated about 25 days after i.v. challenge with CT-26 cells. The mice were sacrificed and necropsied, and the tumor burdens of the lungs were evaluated by recording the average weight of the lungs from each group. A normal lung weight is about 0.2 grams. FIG. 22 illustrates typical lungs (top) removed from the vaccinated, CT-26 challenged mice. FIG. 22 also includes a graph (bottom) of average lung weight for each treatment group. A dramatic decrease in tumor burden was observed for mice vaccinated with the H60/muSurvivin vaccine of the invention compared to the control vaccines.

Figure 23:
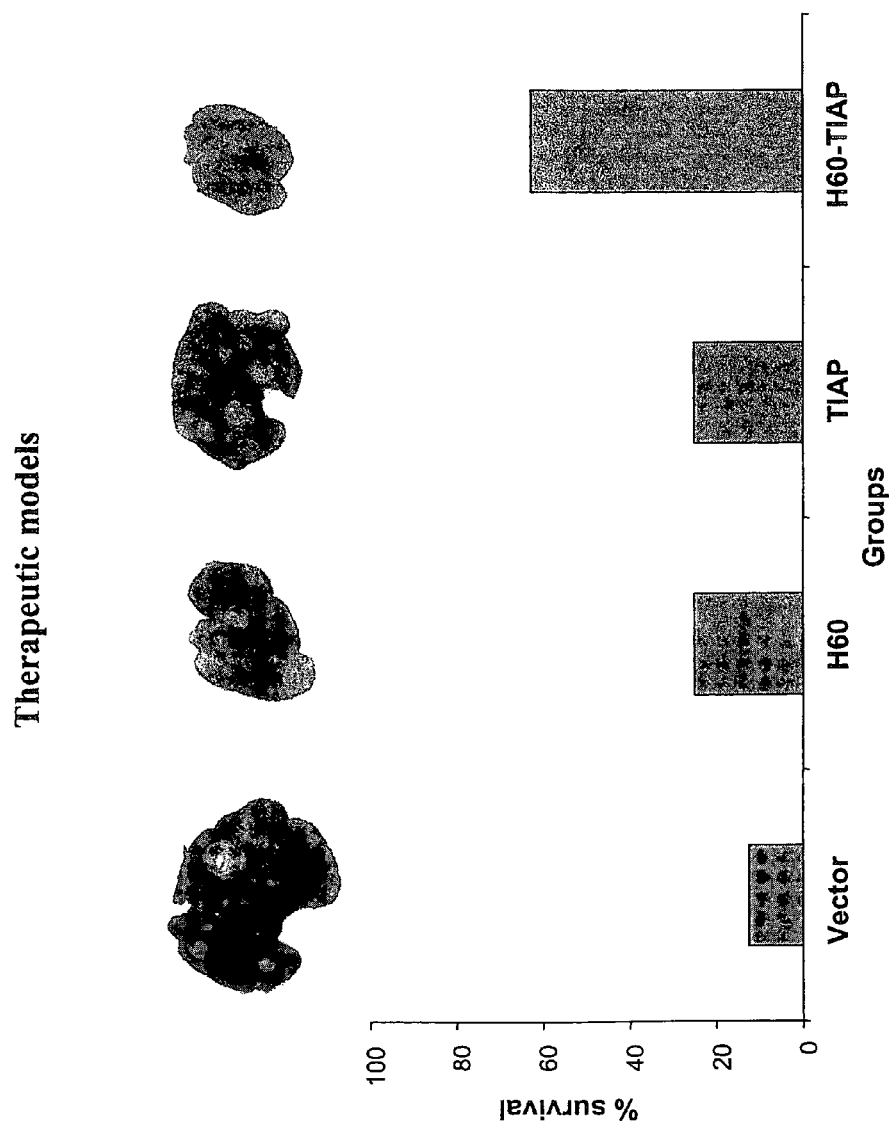
FIG. 23 is a graph of the percentage survival of mice vaccinated and challenged with CT-26 tumor cells.

FIG. 23 includes a graph of percentage of mice surviving after 26 days for each treatment group. A significant increase in survival was observed for mice vaccinated with the H60/muSurvivin vaccine of the invention compared to the control vaccines.

EXAMPLE 13

Evaluation of Expression of H60 and muSurvivin in 293T Cells

Figure 24:
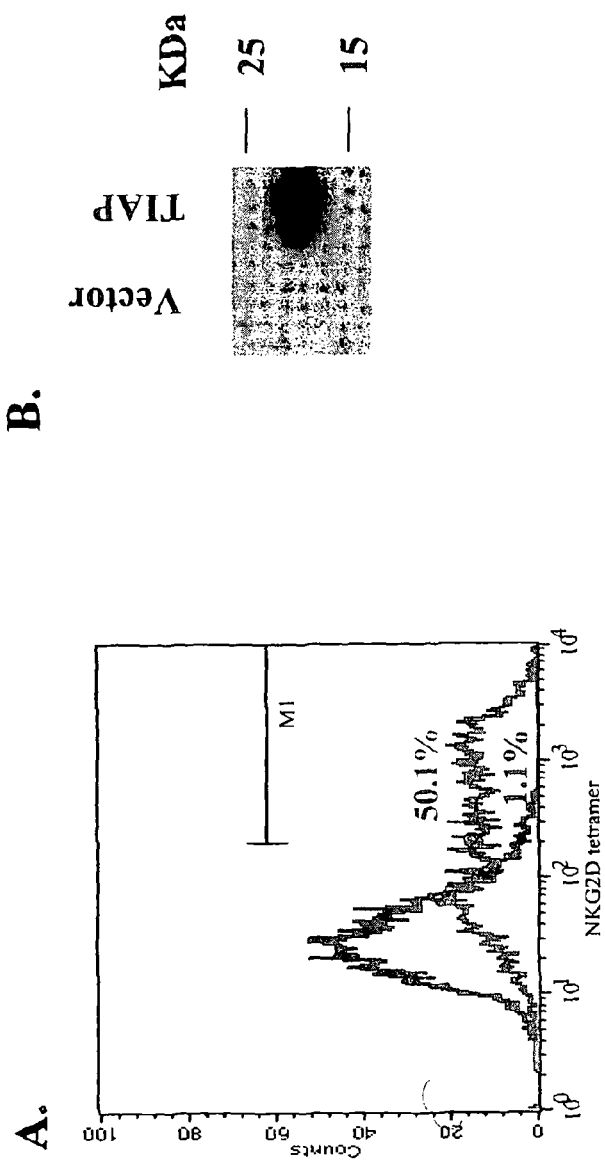
FIG. 24 illustrates expression of H60 peptide (A) and muSurvivin (B)

FIG. 24A illustrates expression of H60. 293T cells were transfected with either empty vector (V) or pH60 (H) for 24 hours, harvested and stained with NKG2D tetramer, and analyzed by flow cytometry. The transfection efficiency was about 45% as assessed by pGFP (Green Fluorescent Protein) transfection. FIG. 24B illustrates expression of muSurvivin. The 293T cells were transfected with either empty vector or pmuSurvivin for 24 hours, harvested, lysed and analyzed by western blot. The western blot indicates that muSurvivin is detectable in the transfected cells, but not in the native cells.

Part B. Vaccines from Transformed AroA⁻, dam⁻ Doubly Attenuated *Salmonella typhimurium*

EXAMPLE 14

Preparation of a DNA Vaccine Encoding muSurvivin and muCCL21

The full-length coding regions for murine survivin (muSurvivin) and murine CCL21 (muCCL21) were amplified by the reverse transcription-polymerase chain reaction using 1 µg of total RNA extracted from D121 mouse Lewis lung carcinoma cells and activated mouse splenocytes, respectively. Total RNA was extracted with the RNEASY® Mini kit (Qiagen, Valencia, Calif.) and RT-PCR was performed with a platinum quantitative RT-PCR thermoscript one-step system (Gibco/BRL) according to the manufacturer's instructions. Several constructs were made based on the pBudCE4.1 vector (Invitrogen) by using the PCR products designed for independent expression of two genes from a single plasmid in mammalian expression vectors. The first construct, muSurvivn/muCCL21 comprising full-length murine survivin and murine CCL21, was inserted into the multi-cloning site A between restriction sites HindIII and BamHI. Chemokine muCCL21 was generated by inserting the gene into the multi-cloning site B between restriction sites XhoI and NotI, respectively. The other vectors used for DNA vaccination were based on the first construction rather than on the absence of either muCCL21 or muSurvivin. The empty vector was generated as a control.

Protein expression of muSurvivin and muCCL21 was demonstrated by Western blotting of cell lysates following transfection of plasmids into COS-7 cells using anti-survivin and anti-CCL21 Abs, respectively. Expression of EGFP activity in Peyer's Patches of C57BL/6J mice was detected in mice after oral administration of $10^8$ *Salmonella typhimurium* (AroA⁻, dam⁻ strain RE88) transformed with pEGFP. Mice were sacrificed at time points of 8, 16, and 36 hours and fresh specimens of small intestine were removed for analysis after thoroughly washing with PBS. Fluorescence expression of EGFP was detected by confocal microscopy.

Possible toxicities caused in the host by the attenuated bacteria were evaluated by comparing the doubly attenuated AroA⁻, dam⁻ strain RE88 with the single attenuated AroA⁻ strain SL2707. Use of the RE88 strain resulted in the survival of all 16 mice without any obvious toxic side effects, whereas 2 of 16 mice immunized with the SL2707 strain died of toxicity and infection. Thus, the dam⁻ mutation of the RE88 strain, which controls bacterial virulence, apparently rendered this strain particularly useful as a DNA vaccine carrier.

EXAMPLE 15

Oral Vaccination and Tumor Challenge of Mice with a Vaccine of Example 14

C57BL/6J mice were divided into five groups and were immunized 3 times at 2-week intervals by gavage with about 100 µl PBS containing about $1 \times 10^8$ doubly attenuated *S. typhimurium* (RE88) harboring either of the following: empty vector pBUd; individual expression vectors of either pBud-muSurvivn/muCCL21, pBud-muSurvivin, or pBud-muCCL21 along with PBS treatment groups. All mice in prophylactic treatments were challenged by i.v. injections of about $1 \times 10^5$ D121 murine Lewis lung carcinoma cells about 1 week after the last immunization. In therapeutic settings, mice were first injected i.v. with about $1 \times 10^5$ D121 murine Lewis lung carcinoma and 1 week later were subjected to 3 vaccinations with the transformed *S. typhimurium*. Mice were examined daily, sacrificed and examined for lung metastasis about 28 days after tumor cell challenge in the prophylactic setting or 63 days after the initial tumor cell inoculation in the therapeutic model.

Tumor metastasis scores following immunization with either PBS, empty vector, CCL21, survivin or CCL21/ survivin vaccines, respectively, for prophylactic treatment with the vaccines are shown in Table 3. Results in Table 3 are shown as metastasis scores expressed as the % lung surface covered by fused metastatic foci: 0=none; 1=less than 5%; 2=5 to 50%; and 3=>50%. Differences in metastasis scores between groups of mice treated with the CCL21/survivin vaccine and all control groups were statistically significant (P=<0.001). Inhibition of tumor growth was also observed in this therapeutic model.

TABLE 3

Tumor Metastasis in Balb/C Mice Challenged with D121 Lewis Lung Carcinoma Cells Post Vaccination.

| Mouse Vaccination Group | Metastatic Scores |
| --- | --- |
| A. muSurvivin/muCCL21 Vaccine | 0, 0, 0, 0, 0, 0, 1, 1 |
| B. Control - muSurvivin Vaccine | 0, 1, 1, 2, 2, 3, 3, 3 |
| C. Control - muCCL21 vaccine | 2, 2, 2, 2, 3, 3, 3, 3 |
| D. Control - empty vector vaccine | 3, 3, 3, 3, 3, 3, 3, 3 |
| E. Control - vaccination with PBS | 3, 3, 3, 3, 3, 3, 3 |

In this prophylactic setting we observed decisive suppression of disseminated pulmonary metastases of D121 murine Lewis lung carcinoma in the mice vaccinated 3 times at 2 week intervals and then challenged 1 week later by i.v. injection of tumor cells. Indeed, 6 of 8 mice completely rejected all pulmonary tumor metastases while the remaining animals revealed a markedly increased suppression of tumor metastases (see Table 3). In contrast, the survivin-based DNA vaccine lacking muCCL21 induced complete suppression of metastases in only one of 8 animals, two exhibited less than 5% metastatic tumor growth, while all remaining mice showed extensive metastatic tumor growth. Additional animals that were treated only with control vaccinations of either PBS or empty vector showed no tumor protection at all and died within 4 weeks after tumor cell challenge due to extensive metastases. Although immunization with doubly attenuated *Salmonella* carrying only the secretory muCCL21 plasmid did not dramatically suppress tumor metastasis, it still resulted in statistically significant delays of metastases when compared to controls.

Importantly, the muSurvivin/muCCL21-based DNA vaccine was also effective in markedly suppressing the growth of already well established pulmonary metastases in all experimental animals in a therapeutic setting. In contrast, all mice receiving only the muSurvivin- or muCCL21-based vaccines per se, or empty vector and PBS controls, revealed large disseminated pulmonary metastases of D121 non-small cell lung carcinoma in this experimental setting. Lung weights of the various experimental groups from the therapeutic model are indicated in Table 4. Normal lung weight was about 0.3 g.

TABLE 4

Tumor Metastasis in Balb/C Mice Pre-Challenged with D121 Lewis Lung Carcinoma Cells - Lung Weight.

| Mouse Vaccination Group | Lung Weight (g) |
| --- | --- |
| A. muSurvivin/muCCL21 Vaccine | 0.34 ± 0.06 |
| B. Control - muSurvivin Vaccine | 0.56 ± 0.09 |
| C. Control - muCCL21 vaccine | 0.86 ± 0.11 |
| D. Control - empty vector vaccine | 1.29 ± 0.4 |
| E. Control - vaccination with PBS | 1.2 ± 0.34 |

EXAMPLE 16

Determination of Anti-Angiogenic Effects in the Vaccinated Mice of Example 15

Two weeks after the last vaccination, mice were injected subcutaneously (s.c.) in the sternal region with about 500 ml of growth factor-reduced matrigel (BD Biosciences) containing about 400 ng/ml of murine FGF-2 (PeproTech, Rocky Hill, N.J.) and D121 tumor cells ($1\times10^4$/ml) which were irradiated with 1000 Gy. In all mice, except for 2 control animals, endothelium tissue was stained 6 days later by injection into the lateral tail vein with 200 ml of 0.1 mg/ml fluorescent *Bandeiraea simplicifolia* lectin I, Isolectin B4 (Vector Laboratories, Burlingame, Calif.); about 30 minutes later, mice were sacrificed and Matrigel plugs excised and evaluated macroscopically. Lectin-FITC was then extracted from 100 ml of each plug in 500 ml of RIPA lysis and quantified by fluorimetry at 490 nm. Background fluorescence found in the two non-injected control mice was subtracted in each case.

The muSurvivin/muCCL21-based vaccine decisively suppressed angiogenesis in the tumor vasculature. A significant decrease in tumor neovascularization was observed, as indicated by Matrigel assays and quantification by relative fluorescence measured after in vivo staining of mouse endothelium with FITC-conjugated lectin. Macroscopically evident differences in tumor vascularization were observed among groups treated with the muSurvivin/muCCL212 vaccine and control groups of mice upon examination of representative Matrigel plugs removed 6 days after s.c. injection of FITC-conjugated lectin. The mice vaccinated with a vaccine of the invention exhibited significantly less tumor vascularization relative to the control groups.

EXAMPLE 17

Cytotoxicity Assay

Splenocytes were isolated from successfully vaccinated mice 5 d after tumor cell challenge. Cytotoxicity was assessed by a standard $^{51}$Cr-release assay against targets of either D121 tumor cells or murine endothelial cells overexpressing survivin. To determine specific MHC class I-restriction of cytotoxicity, the inhibition evaluations were performed with 10 μg/ml anti-mouse MHC class I H-2 Kb/Db Abs (PharMingen, San Diego, Calif.).

The $^{51}$Cr-release assay indicated marked cytotoxicity induced by specific CD8$^+$ T cells obtained from mice after vaccination and subsequent challenge with D121 Lewis lung carcinoma cells. The CD8$^+$ T cells isolated from splenocytes of mice immunized with either muSurvivin/muCCL21 or the muSurvivin vaccine per se, effectively lysed 50% and 30% of D121 tumor cells, respectively. In contrast, CD8$^+$ T cells isolated from control animals were ineffective in evoking any noticeable killing of tumor cells, as they showed only background cytotoxic activities. Characteristically, the CD8$^+$ T cell-mediated cytotoxicity observed was MHC class 1 antigen-restricted since the cytotoxicity was completely eliminated by the addition of anti-H2Kb/H2 Db Abs.

EXAMPLE 18

Flow Cytometric Analysis and Cytokine Release Assay

Activation markers of T cells and expression of costimulatory molecules on CD11c and MHC class II Ag-positive DCs were determined by 2 or 3-color flow cytometric analyses with a BD Biosciences FACScan. T cell activation was determined by staining freshly isolated splenocytes from successfully vaccinated mice with FITC-labeled anti-CD3e Ab in combination with PE-conjugated anti-CD25, CD28 or CD69 Abs. Activation of costimulatory molecules on APCs was measured with FITC-labeled anti-CD11c Ab and biotinylated anti-IAb Ab, followed by streptavidin-allophycocyanin, and in combination with PE-conjugated anti-ICAM-1, CD80 or DEC205 Abs. All cytometric flow experiments were performed in the presence of 0.1 μg/ml propidium iodide to exclude dead cells. All reagents for these assays were obtained from BD Pharmingen (La Jolla, Calif.).

Flow cytometry was used for detection of intracellular cytokines. To this end, splenocytes were collected from B57BL/6J mice about 2 weeks after D121 tumor cell challenge and cultured for about 24 hours in complete T cell medium together with irradiated D121 cells as described previously. Preincubated cells were suspended with about 1 mg purified 2.4G2 Ab (BD Pharmingen) to block nonspecific staining. The cells were washed and then stained with 0.5 mg FITC conjugated anti-CD3+ Ab. After washing 2 times, cells were fixed and stained with 1 mg/ml PE conjugated with either anti-IL2 or anti-IFN-g Abs for flow cytometric analysis. All Abs were obtained from BD Pharmingen (La Jolla, Calif.).

Only the muSurvivin/muCCL21 vaccine per se was optimally effective in markedly upregulating the expression of CD25, CD28 and CD69 T-cell activation markers. The upregulation of CD28 is of particular importance since its interactions with B7 costimulatory molecules on DCs is known to be essential to achieve critical and multiple interactions between naïve T-cells and antigen-presenting DCs. In contrast, the DNA vaccines encoding only muSurvivin or muCCL21 per se increased the expression of the T-cell activation markers only 1-fold. Activation of both $CD4^+$ and $CD8^+$ T-cells by the muSurvivin/muCCL21 vaccine was also indicated by their decisive increase in intracellular pro-inflammatory cytokines IFN-g and IL-2. In comparison, PBS and empty vector controls as well as DNA vaccines encoding solely muSurvivin or muCCL21 were found to be considerably less effective in inducing these cytokines.

Upregulated expression of ICAM-1, CD80 and DEC205 on DCs, achieved by the muSurvivin/muCCL21-based DNA vaccine is particularly important since it is well known that the activation of T-cells critically depends on strong cell-cell interactions with these costimulatory molecules expressed on DCs in order to achieve optimal ligation with T-cell receptors. Again, immunization with doubly attenuated *Salmonella typhimurium* carrying eukaryotic plasmids encoding muSurvivin/muCCL21 induced the most effective up-regulation of these activation markers, which was up to 2-3 fold higher than those of controls.

EXAMPLE 19

Analysis of Tumor Cell Apoptosis

Apoptosis in D121 tumor cells induced by vaccination was measured at about 3 hours and about 24 hours after vaccination, respectively. Both control and experimental animals were challenged i.v. with about $1 \times 10^5$ D121 cells 1 week after the last of 3 immunizations. Splenocytes were harvested from each individual mouse 1 week after tumor cell challenge, and thereafter about $2.5 \times 10^7$ splenocytes were co-cultured for 4 hours with about $5 \times 10^5$ D121 cells in 6-well plates. The ANNEXIN®V-FITC apoptosis detection kit II (BD Biosciences Pharmingen, San Diego, Calif.) was used for confirmation of early stage of apoptosis. To confirm later stage tumor cell apoptosis, about $5 \times 10^5$ D121 cells and about $2.5 \times 10^7$ splenocytes were co-cultured for about 24 hours and then analyzed by FACS for apoptosis by the TUNEL assay with the APO-DIRECT™ Kit (BD Biosciences Pharmingen, San Diego, Calif.) according to the manufacturer's instructions.

Apoptosis was observed as early as 3 hours and with a considerable further increase after 24 hours as indicated by flow cytometric analysis of data obtained by either Annexin V or TUNEL assays. Thus, early stage apoptosis was up to 3 to 4 fold higher in groups of mice immunized with the muSurvivin/muCCL21 vaccine than in controls after splenocytes harvested from such mice were co-incubated with tumor cells. The vaccine encoding muSurvivin alone triggered apoptosis somewhat, but only one fold higher than controls. However, a dramatic 85% increase in apoptosis was observed at 24 hours only in mice immunized with the muSurvivin/muCCL21 vaccine, suggesting that a robust tumor cell immunity induced by CTLs triggered this event.

EXAMPLE 20

Preparation of a DNA Vaccine Encoding muSurvivin and H60

A plasmid containing the full-length murine NKG2D ligand-H60 was a generous gift from Drs. A. Diefenbach and D. H. Raulet (University of California, Berkeley, Calif.). Expression vectors were constructed on a pBudCE4.1 (Invitrogen) backbone as described above.

Doubly attenuated *S. typhimurium* (AroA⁻, dam⁻) were transformed with DNA vaccine plasmids by electroporation as previously described hereinabove. Briefly, freshly prepared bacteria (about $1 \times 10^8$), at midlog growth phase, were mixed with plasmid DNA (1-2 μg) on ice in a 0.1-cm cuvette and electroporated at about 2.0 KV, 25 μF, and 100Ω. Resistant colonies harboring the DNA vaccine vectors were cultured and stored at −80° C. after confirmation of the coding sequences.

EXAMPLE 21

Oral Vaccination and Tumor Challenge of Mice with a Vaccine of Example 20

Groups of BALB/c A2Kb mice (n=4-12) were immunized twice at a 2-week intervals by gavage with 100 μl PBS containing approximately $5 \times 10^8$ doubly attenuated *S. typhimurium* harboring the expression vectors. In prophylactic models, BALB/c mice were challenged i.v. with about $1 \times 10^5$ CT-26 cells 2 weeks after the last vaccination, and in therapeutic settings 5 days before the first vaccination. Mice were sacrificed 25 d or 28 days after tumor challenge, and lung metastasis or tumor weights, respectively were determined and compared with those of controls. The statistical significance of differential findings between experimental groups and controls was determined by Student's t test. Findings were regarded as significant, if two-tailed P values were <0.05.

Expression of H60 and muSurvivin were confirmed by transfecting 293T cells and checked by flow cytometry or Western blot analysis. The expression of H60 was confirmed by the positive staining of NKG2D tetramer. Cells transfected with Survivin tested positive as indicated by a single band at the expected molecular weight of approximately 16.5 KDa. The level of NKG2D ligand expressed by CT-26 is relatively low when compared to the positive control, Yac-1 cells. Tumor cells with low levels of NKG2D ligand expression were previously reported to fail in inducing tumor rejection. In the prophylactic setting, lung weights and metastasis scores (as described hereinabove) were assessed after sacrifice of the mice 25 days after tumor challenge. The results are shown in Table 5 and Table 6. The data show that the H60 and muSurvivin vaccines individually protected the mice to some extent, whereas the combination of H60 and muSurvivin (muSurvivin/H60 vaccine) greatly enhanced protection against tumor challenges as demonstrated by significantly lower metastasis scores and decreased tumor loads in the lungs. These findings were statistically significant when compared to PBS, pBud, pH60 and pmuSurvivin control groups (p<0.0001, 0.002, 0.01, and 0.005, respectively).

In a therapeutic settings i.e. against established colon carcinoma metastases, lung tumor burden was assessed after sacrifice at day 28. Significantly, 8 of 12 mice treated with H60/muSurvivin vaccine survived and, more importantly, 2 of these surviving animals were completely free of metastases, while 2 others had less than 5% of their lung surface covered by fused tumor metastases. By comparison, only 2 mice survived in the empty pBud vector-treated control group, and more than 50% of the lung surface of all surviving mice was covered by fused tumor metastases. Vaccination with muSurvivin vaccine alone did not result in any significant protection in the therapeutic model, and treatment with H60 vaccine alone had only marginal therapeutic effect. The latter was suggested by a slightly improved survival rate and by one of the surviving mice having only <5% of its lung surface covered by fused tumor metastases.

TABLE 5

Tumor Metastasis in Balb/C Mice Challenged with CT-26 Cells After Immunization.

| Mouse Vaccination Group | Metastatic Scores | No. of Mice Surviving |
| --- | --- | --- |
| A. muSurvivin/H60 Vaccine | 0, 0, 1, 1, 1, 2 | 6 |
| B. Control - muSurvivin Vaccine | 1, 1, 1, 1, 2, 2 | 6 |
| C. Control - H60 vaccine | 0, 1, 1, 1, 3, 3 | 6 |
| D. Control - empty vector vaccine | 3, 3, 3, 3 | 4 |
| E. Control - vaccination with PBS | 2, 3, 3, 3 | 4 |

TABLE 6

Tumor Metastasis in Balb/C Mice Challenged with CT-26 Cells Before Immunization.

| Mouse Vaccination Group | Metastatic Scores | No. of Mice Surviving |
| --- | --- | --- |
| A. muSurvivin/H60 Vaccine | 0, 1, 1, 2, 3, 3, 3 | 8 |
| B. Control - muSurvivin Vaccine | 3, 3 | 2 |
| C. Control - H60 vaccine | 1, 3, 3 | 3 |
| D. Control - empty vector vaccine | 2, 3 | 2 |

EXAMPLE 22

Cytotoxicity Assay

Cytotoxicity was measured by a standard $^{51}$Cr-release assay as previously described hereinabove. Briefly, splenocytes were harvested 2 weeks after the last immunization, and stimulated in vitro by irradiated (1,000 Gy) CT-26 cells at 37° C. for 5 days in RPMI 1640 supplemented with 10% FBS, L-Glutamine, 15 mM HEPES, non-essential amino acids, sodium pyruvate, 2-ME and recombinant IL-2 at 20 U/ml (PeproTech, Rocky Hill, N.J.). Splenocytes were harvested and separated with Lympholyte-M cell separation media (Cedarlane Laboratories Limited, Hornby, Ontario, Canada). Target cells were labeled with $^{51}$Cr for about 1.5 hours at room temperature, and incubated with effector cells at various effector-to-target cell ratios at about 37° C. for about 4 hours. The percentage of specific target cell lysis was calculated by the formula $[(E-S)/(T-S)] \times 100$, where E is the average experimental release, S the average spontaneous release, and T the average total release.

NK activity was found to be significantly enhanced in mice immunized with H60 vaccine, and even greater NK killing was observed in mice immunized with the muSurvivin/H60 vaccine. Splenocytes from mice immunized with the muSurvivin/H60 vaccine showed the highest cytotoxicity against CT-26 target cells. In contrast, such splenocytes isolated from pBud immunized controls revealed minimal cytotoxic killing, while those splenocytes from H60 vaccine or muSurvivin vaccinated mice per se showed somewhat higher cytotoxic killing. After 5 days of cell culture, NK cells did not appear to play a major roll in this cytotoxicity assay as no significant difference was seen when Yac-1 NK target cells were used, suggesting the cytotoxicity detected was mainly mediated by CTLs.

Numerous variations and modifications of the embodiments described above can be effected without departing from the spirit and scope of the novel features of the invention. No limitations with respect to the specific embodiments illustrated herein are intended or should be inferred.

We claim:

1. An article of manufacture comprising a DNA vaccine suitable for eliciting an immune response against cancer cells comprising a DNA construct operably encoding at least one survivin protein and at least one CCL 21 cytokine in a pharmaceutically acceptable carrier, wherein the DNA construct is incorporated in an attenuated *Salmonella typhimurium* vector that targets Peyer's patches in the gut, wherein the DNA vaccine induces a cytotoxic T-lymphocyte immune response against tumor cells when orally administered to the patient, and the attenuated *Salmonella typhimurium* vector comprises an aroA⁻, dam⁻ *Salmonella typhimurium* strain packaged in a hermetically sealed, sterile container, the container having a label affixed thereto, the label bearing printed material identifying the vaccine and providing information useful to an individual administering the vaccine to a patient.

2. A transformed host cell transfected with a plasmid vector comprising a DNA construct operably encoding a survivin protein and a CCL 21 cytokine wherein the DNA construct is incorporated in an attenuated *Salmonella typhimurium* vector that targets Peyer's patches in the gut, wherein the DNA vaccine induces a cytotoxic T-lymphocyte immune response against tumor cells when orally administered to the patient, and the attenuated *Salmonella typhimurium* vector comprises an aroA⁻, dam⁻ *Salmonella typhimurium* strain.

* * * * *